(12) United States Patent
Mammen et al.

(10) Patent No.: US 7,285,564 B2
(45) Date of Patent: Oct. 23, 2007

(54) SUBSTITUTED 4-AMINO-1-(PYRIDYLMETHYL)PIPERIDINE AND RELATED COMPOUNDS

(75) Inventors: Mathai Mammen, Redwood Shores, CA (US); Richard Wilson, El Sobrante, CA (US); Yan Chen, Burlingame, CA (US); Sarah Dunham, San Rafael, CA (US); Adam Hughes, San Francisco, CA (US); Craig Husfeld, Redwood City, CA (US); Yu-Hua Ji, Redwood City, CA (US); Li Li, Sunnyvale, CA (US); Trevor Mischki, Burlingame, CA (US); Ioanna Stergiades, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 490 days.

(21) Appl. No.: 10/696,464

(22) Filed: Oct. 29, 2003

(65) Prior Publication Data

US 2004/0122014 A1    Jun. 24, 2004

Related U.S. Application Data

(60) Provisional application No. 60/486,483, filed on Jul. 11, 2003, provisional application No. 60/422,229, filed on Oct. 30, 2002.

(51) Int. Cl.
*A61K 31/445* (2006.01)
*C07D 401/14* (2006.01)

(52) U.S. Cl. .................. 514/318; 514/256; 546/193; 544/333

(58) Field of Classification Search ............ 514/318, 514/256; 546/193; 544/333
See application file for complete search history.

(56) References Cited

U.S. PATENT DOCUMENTS

| | | |
|---|---|---|
| 3,192,206 A | 6/1965 | Lunsford et al. |
| 3,192,210 A | 6/1965 | Lunsford et al. |
| 3,192,221 A | 6/1965 | Lunsford et al. |
| 3,984,557 A | 10/1976 | Welstead, Jr. |
| 4,002,766 A | 1/1977 | Welstead, Jr. |
| 4,594,343 A | 6/1986 | Shanklin, Jr. et al. |
| 4,810,713 A | 3/1989 | Yanni et al. |
| 4,950,674 A | 8/1990 | Yanni et al. |
| 5,026,858 A | 6/1991 | Vega-Noverola et al. |
| 5,028,616 A | 7/1991 | Desai et al. |
| 5,070,087 A | 12/1991 | Teng et al. |
| 5,096,890 A | 3/1992 | Cross et al. |
| 5,233,053 A | 8/1993 | Cross et al. |
| 5,281,601 A | 1/1994 | Cross et al. |
| 5,340,831 A | 8/1994 | Cross et al. |
| 5,344,835 A | 9/1994 | Alker et al. |
| 5,486,527 A | 1/1996 | Alker et al. |
| 5,607,950 A | 3/1997 | Alker et al. |
| 5,750,540 A | 5/1998 | Tsuchiya et al. |
| 5,932,594 A | 8/1999 | Cross et al. |
| 6,130,232 A | 10/2000 | Mase et al. |
| 6,319,920 B1 | 11/2001 | Caroon et al. |
| 6,635,764 B2 | 10/2003 | Mammen et al. |
| 6,693,202 B1 | 2/2004 | Aggen et al. |
| 2002/0049195 A1 | 4/2002 | Mammen et al. |
| 2003/0055080 A1 | 3/2003 | Forner et al. |
| 2004/0029919 A1 | 2/2004 | Mammen et al. |
| 2004/0054187 A1 | 3/2004 | Mammen et al. |
| 2004/0110229 A1 | 6/2004 | Aggen et al. |
| 2004/0116706 A1 | 6/2004 | Mammen et al. |
| 2005/0026954 A1 | 2/2005 | Mammen et al. |

FOREIGN PATENT DOCUMENTS

| | | |
|---|---|---|
| CH | 628 885 A5 | 3/1982 |
| EP | 0 178 946 A2 | 4/1986 |
| EP | 0 178 947 A2 | 4/1986 |
| EP | 0 235 463 A2 | 9/1987 |
| EP | 0 388 054 B1 | 9/1990 |
| EP | 0 863 141 A1 | 9/1998 |
| EP | 0 930 298 A1 | 7/1999 |
| EP | 0 999 205 A1 | 5/2000 |
| EP | 1 020 449 A1 | 7/2000 |
| GB | 1 507 462 | 4/1978 |
| GB | 1 575 310 | 9/1980 |
| GB | 1 593 851 | 7/1981 |
| WO | WO91/09013 A1 | 6/1991 |
| WO | WO99/43657 A1 | 9/1999 |
| WO | WO99/64043 A1 | 12/1999 |
| WO | WO 01/04118 A2 | 1/2001 |
| WO | WO 02/051841 A1 | 7/2002 |

(Continued)

OTHER PUBLICATIONS

Bohme et al., 2002, J. Med. Chem., 45, 4800.*

(Continued)

*Primary Examiner*—Celia Chang
(74) *Attorney, Agent, or Firm*—Jeffrey A. Hagenah

(57) ABSTRACT

This invention provides 4-amino-1-(pyridylmethyl)piperidine and related compounds and pharmaceutically acceptable salts thereof which are useful as muscarinic receptor antagonists. This invention also provides pharmaceutical compositions containing such compounds; processes and intermediates useful for preparing such compounds; and methods for treating disease conditions mediated by muscarinic receptors, such as overactive bladder, irritable bowel syndrome and chronic obstructive pulmonary disease, using such compounds.

36 Claims, No Drawings

FOREIGN PATENT DOCUMENTS

| | | |
|---|---|---|
| WO | WO 02/053564 A2 | 7/2002 |
| WO | WO 03/048124 A1 | 6/2003 |

OTHER PUBLICATIONS

Bohme et al., 2002, J. Med. Chem., 45, 3094-3102.*
Walsh et al., J. Med. Chem., 1989, 32, pp. 105-118.*
Boselli et al., Journal of Autonomic Pharmacology, 2001, 21, p. 219-229.*
Beringue, et al., 1997, CA 126: 324757, Abstract.*
Tomlinson et al., 1997, CA 127: 174580, Abstract.*
Berge et al. "Pharmaceutical salts" J. Pharm. sciences, vl. 66, p. 1-2 (1977).*
Pratesi et al. "Affinity and intrinsic . . . " CA 70:37081 (1969).*
CA 60:74793 (1964), see marked entry.*
Laeckmann et al. "Synthesis and biological . . . " Bioorg. med. Chem. v. 10 (2002) p. 1793-1804.*
Wermuth "The practice of medicinal chemistry" (1996) p. 203-213.*

Broadley et al., "Muscarinic Receptor Agonists and Antagonists", Molecules 2001, 6, pp. 142-193 (2001).
Eglen et al., "Muscarinic Receptor Subtypes: Pharmacology and Therapeutic Potential", DN&P, 10(8), pp. 462-469 (1997).
Eglen et al., "Selective modulation of muscarinic receptor subtypes: therapeutic potential", Emerging Drugs:The Prospect for Improved Medicines/Annual Executive Briefing 1998; pp. 67-79 (1998).
Graul et al., "Darifenacin", Drugs of the Future 1996, 21 (11); pp. 1105-1108 (1996).
Moragues et al., "Dopaminergic Activity in a Series of N-Substituted 2-Aminopyrimidines", II Farmaco -Ed. Sc. -vol. 35—Fasc. 11; pp. 951-964 (1980).
Shum et al., "The Design and Synthesis of Purine Inhibitors of CDK2.III", Nucleosides, Nucleotides & Nucleic Acids, 20(4-7), pp. 1067-1078 (2001).
Zlotos et al., "Muscarinic receptor agonists and antagonists", Exp. Opin. on Ther. Patents, 9(8), pp. 1029-1053 (1999).

* cited by examiner

SUBSTITUTED 4-AMINO-1-(PYRIDYLMETHYL)PIPERIDINE AND RELATED COMPOUNDS

CROSS-REFERENCE TO RELATED APPLICATIONS

This application claims the benefit of U.S. Provisional Application No. 60/422,229, filed on Oct. 30, 2002, and U.S. Provisional Application No. 60/486,483, filed on Jul. 11, 2003; the entire disclosures of which are incorporated herein by reference in their entirety.

BACKGROUND OF THE INVENTION

1. Field of the Invention

This invention is directed to substituted 4-amino-1-(pyridylmethyl)-piperidine and related compounds which are useful as muscarinic receptor antagonists. This invention is also directed to pharmaceutical compositions comprising such compounds; methods of using such compounds for treating medical conditions mediated by muscarinic receptors; and processes and intermediates for preparing such compounds.

2. State of the Art

The muscarinic receptor family comprises five known receptor subtypes, i.e., $M_1$, $M_2$, $M_3$, $M_4$ and $M_5$ receptors, with each receptor subtype having a distinct distribution and function. For example, smooth muscle tissues typically express both $M_2$ and $M_3$ receptor subtypes and these receptors serve to mediate the contraction of these tissues.

As a result, compounds that act as muscarinic receptor antagonists are known to be useful for treating various medical conditions associated with improper smooth muscle function, such as overactive bladder (OAB), irritable bowel syndrome (IBS) and chronic obstructive pulmonary disease (COPD). These smooth muscle function disorders are highly prevalent in society resulting in enormous economic costs. For example, in the United States alone, an estimated 30 million people, primarily women and the elderly, suffer from overactive bladder and approximately $10 billion are spent annually treating this condition. More importantly, the quality of life and self-esteem of patients afflicted with these disorders is often significantly impaired.

Until recently, most compounds which act as muscarinic receptor antagonists were relatively non-selective for the various muscarinic receptor subtypes. As a result, such compounds often produced unpleasant side-effects, such as dry-mouth, constipation, blurred vision, or cognitive side effects. The most common of these side-effects is dry-mouth which results from inhibition of $M_3$ receptors in the salivary gland. This dry-mouth side effect is often so severe that an estimated 80 to 85 percent of patients being treated for overactive bladder discontinue their medication within six months and, as a result, their condition goes untreated.

Accordingly, a need exists for new muscarinic receptor antagonists. In particular, a need exists for new muscarinic receptor antagonists which selectively inhibit $M_2$ receptors relative to $M_3$ receptors. Such compounds are expected to be particularly effective for treating smooth muscle disorders mediated by $M_2$ and $M_3$ receptor subtypes, such as overactive bladder, while reducing or eliminating the dry-mouth, constipation and blurred vision side-effects mediated predominately by the $M_3$ receptor subtype.

SUMMARY OF THE INVENTION

The present invention provides novel substituted 4-amino-1-(pyridylmethyl)piperidine and related compounds which are useful as muscarinic receptor antagonists. Among other properties, compounds of this invention have been found to be potent inhibitors of $M_2$ receptor activity. Additionally, compounds of this invention have been found to possess surprising and unexpected selectivity for the $M_2$ receptor subtype relative to the $M_3$ receptor subtype.

Accordingly, in one of its composition aspects, this invention provides a compound of formula I:

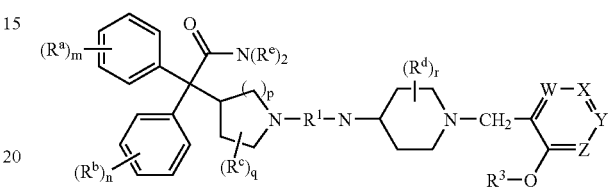

wherein

W, X, Y and Z are independently selected from the group consisting of CH, $CR^4$, N and N→O; provided that at least one and no more than two of W, X, Y and Z are N or N→O;

$R^1$ is a group of formula (a):

$$-(CH_2)_a-(O)_b-(CH_2)_c-  \quad \text{(a)}$$

wherein each $-CH_2-$ group in formula (a) and the $-CH_2-$ group between the piperidine nitrogen atom and the ring containing W, X, Y and Z in formula I is optionally substituted with 1 or 2 substituents independently selected from the group consisting of $C_{1-2}$ alkyl and fluoro; wherein each alkyl group is optionally substituted with 1 to 3 fluoro substituents;

$R^2$ is selected from the group consisting of hydrogen, $C_{1-6}$ alkyl, $C_{2-6}$ alkenyl, $C_{2-4}$ alkynyl, $C_{3-6}$ cycloalkyl, $-CH_2-R^5$ and $-(CH_2)_x-R^6$; wherein each alkyl, alkenyl, alkynyl and cycloalkyl group is optionally substituted with 1 to 5 fluoro substituents;

each $R^3$ is independently selected from the group consisting of hydrogen, $C_{1-6}$ alkyl, $C_{2-6}$ alkenyl, $C_{2-6}$ alkynyl, $C_{3-6}$ cycloalkyl, $-CH_2-R^7$ and $-(CH_2)_y-R^8$; wherein each alkyl, alkenyl, alkynyl and cycloalkyl group is optionally substituted with 1 to 5 fluoro substitutents;

each $R^4$ is independently selected from the group consisting of $C_{1-6}$ alkyl, $C_{2-4}$ alkenyl, $C_{2-6}$ alkynyl, $C_{3-6}$ cycloalkyl, $-OR^3$ and halo; or two adjacent $R^4$ groups are joined to form $C_{3-6}$ alkylene, $-O-(C_{2-4}$ alkylene)$-$, $-O-(C_{1-4}$ alkylene)$-O-$, $-(O)C-CH=CH-$ or $-CH=CH-C(O)-$; or when Z is $CR^4$, $-OR^3$ and $R^4$ are joined to form $-O-(C_{2-5}$ alkylene)- or $-O-(C_{1-5}$ alkylene)-$O-$; wherein each alkyl, alkylene, alkenyl, alkynyl and cycloalkyl group is optionally substituted with 1 to 5 fluoro substitutents;

each $R^5$ and $R^7$ is independently selected from the group consisting of $C_{3-5}$ cycloalkyl, $C_{6-10}$ aryl, $-C(O)(C_{6-10}$ aryl), $C_{2-9}$ heteroaryl, $-C(O)(C_{2-9}$ heteroaryl) and $C_{3-6}$ heterocyclic; wherein the cycloalkyl group is optionally substituted with 1 to 5 fluoro substituents; and the aryl, heteroaryl and heterocyclic groups are optionally substituted with 1 to 3 substituents independently selected from $R^k$ and the aryl and heteroaryl groups are optionally further substituted with a phenyl group, where the phenyl group is optionally substituted with 1 to 3 substituents independently selected from $R^k$;

each $R^6$ and $R^8$ is independently selected from the group consisting of —OH, —OR$^9$, —SR$^9$, —S(O)R$^9$, —S(O)$_2$R$^9$, —C(O)R$^9$, C$_{3-5}$ cycloalkyl, C$_{6-10}$ aryl, C$_{2-9}$ heteroaryl and C$_{3-6}$ heterocyclic; wherein the cycloalkyl group is optionally substituted with 1 to 5 fluoro substituents; and the aryl, heteroaryl and heterocyclic groups are optionally substituted with 1 to 3 substituents independently selected from R$^k$;

each $R^9$ is independently selected from the group consisting of C$_{1-4}$ alkyl, C$_{3-5}$ cycloalkyl, C$_{6-10}$ aryl and C$_{2-9}$ heteroaryl; wherein the alkyl and cycloalkyl groups are optionally substituted with 1 to 5 fluoro substituents; and the aryl and heteroaryl groups are optionally substituted with 1 to 3 substituents independently selected from R$^k$;

each $R^a$ and $R^b$ is independently selected from the group consisting of C$_{1-4}$ alkyl, C$_{2-4}$ alkenyl, C$_{2-4}$ alkynyl, C$_{3-4}$ cycloalkyl, cyano, halo, —OR$^f$, —SR$^f$, —S(O)R$^f$, —S(O)$_2$R$^f$ and —NR$^g$R$^h$; or two adjacent R$^a$ groups or two adjacent R$^b$ groups are joined to form C$_{3-6}$ alkylene, —(C$_{2-4}$ alkylene)-O— or —O—(C$_{1-4}$ alkylene)-O—; wherein each alkyl, alkylene, alkenyl, alkynyl and cycloalkyl group is optionally substituted with 1 to 5 fluoro substitutents;

each $R^c$ and $R^d$ is independently selected from the group consisting of C$_{1-4}$ alkyl and fluoro; wherein each alkyl group is optionally substituted with 1 to 5 fluoro substituents;

each $R^e$ is independently selected from the group consisting of hydrogen, C$_{1-6}$ alkyl, C$_{2-6}$ alkenyl, C$_{2-6}$ alkynyl, C$_{3-6}$ cycloalkyl, C$_{6-10}$ aryl, C$_{2-9}$ heteroaryl, C$_{3-6}$ heterocyclic, —CH$_2$—R$^i$ and —CH$_2$CH$_2$—R$^j$; or both R$^e$ groups are joined together with the nitrogen atom to which they are attached to form C$_{3-6}$ heterocyclic; wherein each alkyl, alkenyl, alkynyl and cycloalkyl group is optionally substituted with 1 to 5 fluoro substitutents; and each aryl, heteroaryl and heterocyclic group is optionally substituted with 1 to 3 substituents independently selected from R$^k$;

each $R^f$ is independently selected from the group consisting hydrogen, C$_{1-4}$ alkyl, C$_{2-4}$ alkenyl, C$_{2-4}$ alkynyl and C$_{3-6}$ cycloalkyl; wherein each alkyl, alkenyl, alkynyl and cycloalkyl group is optionally substituted with 1 to 5 fluoro substitutents;

each $R^g$ and $R^h$ is independently selected from the group consisting of hydrogen, C$_{1-4}$ alkyl, C$_{2-4}$ alkenyl, C$_{2-4}$ alkynyl and C$_{3-6}$ cycloalkyl; or R$^g$ and R$^h$ are joined together with the nitrogen atom to which they are attached to form C$_{3-6}$ heterocyclic; wherein each alkyl, alkenyl, alkynyl and cycloalkyl group is optionally substituted with 1 to 5 fluoro substitutents, and the heterocyclic group is optionally substituted with 1 to 3 substituents independently selected from C$_{1-4}$ alkyl and fluoro;

each $R^i$ is independently selected from the group consisting of C$_{3-6}$ cycloalkyl, C$_{6-10}$ aryl, C$_{2-9}$ heteroaryl and C$_{3-6}$ heterocyclic; wherein aryl, cycloalkyl, heteroaryl and heterocyclic group is optionally substituted with 1 to 3 substituents independently selected from R$^k$;

each $R^j$ is independently selected from the group consisting of C$_{3-6}$ cycloalkyl, C$^{6-10}$ aryl, C$_{2-9}$ heteroaryl, C$_{3-6}$ heterocyclic, —OH, —O(C$_{1-6}$ alkyl), —O(C$_{3-6}$ cycloalkyl), —O(C$_{6-10}$ aryl), —O(C$_{2-9}$ heteroaryl), —S(C$_{1-6}$ alkyl), —S(O)(C$_{1-6}$ alkyl), —S(O)$_2$(C$_{1-6}$ alkyl), —S(C$_{3-6}$ cycloalkyl), —S(O)(C$_{3-6}$ cycloalkyl), —S(O)$_2$(C$_{3-6}$ cycloalkyl), —S(C$_{6-10}$ aryl), —S(O)(C$_{6-10}$ aryl), —S(O)$_2$(C$_{6-10}$ aryl), —S(C$_{2-9}$ heteroaryl), —S(O)(C$_{2-9}$ heteroaryl) and —S(O)$_2$(C$_{2-9}$ heteroaryl); wherein each alkyl group is optionally substituted with 1 to 5 fluoro substitutents; and each aryl, cycloalkyl, heteroaryl and heterocyclic group is optionally substituted with 1 to 3 substituents independently selected from R$^k$;

each $R^k$ is independently selected from the group consisting of C$_{1-4}$ alkyl, C$_{2-4}$ alkenyl, C$_{2-4}$ alkynyl, cyano, halo, —OR$^f$, —SR$^f$, —S(O)R$^f$, —S(O)$_2$R$^f$ and —NR$^g$R$^h$; or two adjacent R$^k$ groups are joined to form C$_{3-6}$ alkylene, —(C$_{2-4}$ alkylene)-O— or —O—(C$_{1-4}$ alkylene)-O—; wherein each alkyl, alkylene, alkenyl and alkynyl group is optionally substituted with 1 to 5 fluoro substitutents;

a is an integer from 2 to 7;

b is 0 or 1;

c is an integer from 2 to 7; provided that a+b+c equals 7, 8 or 9;

m is an integer from 0 to 3;

n is an integer from 0 to 3;

p is 1 or 2;

q is an integer from 0 to 4;

r is an integer from 0 to 4;

x is an integer from 2 to 4;

y is an integer from 2 to 4;

or a pharmaceutically-acceptable salt or solvate or stereoisomer thereof.

In another of its composition aspects, this invention is directed to a compound of formula II:

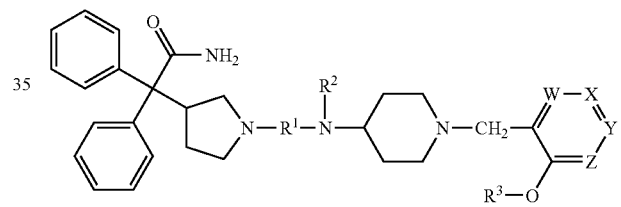

II wherein $R^1$, $R^2$, $R^3$, W, X, Y and Z are as defined herein; or a pharmaceutically-acceptable salt or solvate or stereoisomer thereof.

In yet another of its composition aspects, this invention is directed to a compound of formula III:

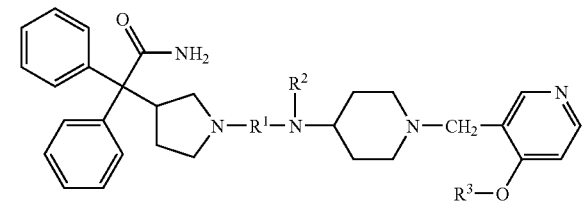

III wherein $R^1$, $R^2$ and $R^3$ are as defined herein; or a pharmaceutically-acceptable salt or solvate or stereoisomer thereof.

This invention is also directed to intermediates useful for preparing compounds of formula I, or salts thereof. Accordingly, in another of its composition aspects, this invention provides a compound of formula IV:

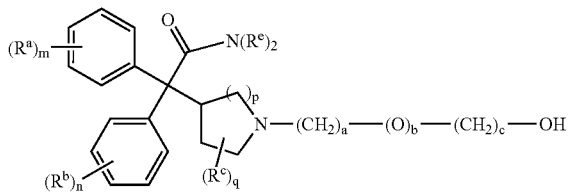

IV wherein $R^a$, $R^b$, $R^c$, $R^e$, a, b, c, m, n, p and q are as defined herein, or a salt or stereoisomer or protected derivative thereof;

or a compound of formula V:

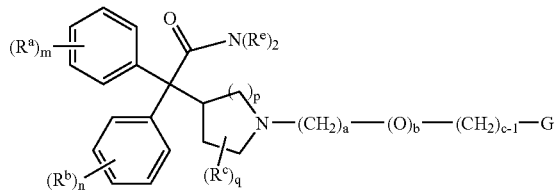

V wherein $R^a$, $R^b$, $R^c$, $R^e$, a, b, c, m, n, p and q are as defined herein, and G is selected from the group consisting of:

—CHO (formula Va),

—CH(OR$^m$), where R$^m$ is $C_{1-6}$ alkyl, or both R$^m$ groups are joined to form $C_{2-6}$ alkylene (formula Vb);

—COOH (formula Vc);

—CH=CH$_2$ (formula Vd);

—CH$_2$-L, where L is a leaving group (formula Ve);

or a salt or stereoisomer or protected derivative thereof;

or a compound of formula VI:

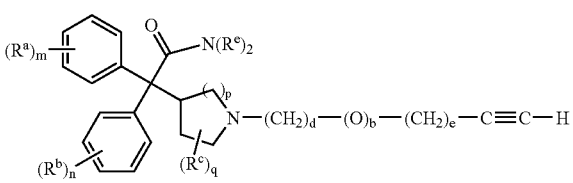

VI wherein $R^a$, $R^b$, $R^c$, $R^e$, m, n, p and q are as defined herein;

d is an integer from 2 to 5;

b is 0 or 1;

e is an integer from 1 to 4, provided that d+b+e+3 equals 7, 8 or 9; or a salt or stereoisomer or protected derivative thereof;

or a compound of formula VII:

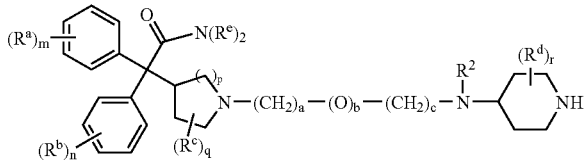

VII wherein $R^2$, $R^a$, $R^b$, $R^c$, $R^d$, $R^e$, a, b, c, m, n, p, q and r are as defined herein, or a salt or stereoisomer or protected derivative thereof; which compounds are useful as intermediates for preparing compounds of formula I.

In yet another of its composition aspects, this invention provides a compound of formula VIII:

VIII $$\underset{HN}{\overset{R^2}{|}} \overset{(R^d)_r}{\underset{|}{\bigcirc}} N-CH_2-\overset{W=X}{\underset{R^3-O}{\bigcirc}}\overset{Y}{\underset{Z}{||}}$$

wherein $R^2$, $R^3$, $R^d$, r, W, X, Y and Z are as defined herein; or a salt or stereoisomer or protected derivative thereof; which compounds are useful as intermediates for preparing compounds of formula I.

In another of its composition aspects, this invention provides a pharmaceutical composition comprising a pharmaceutically-acceptable carrier and a therapeutically effective amount of a compound of formula I, or a pharmaceutically-acceptable salt or solvate or stereoisomer thereof.

The compounds of this invention are muscarinic receptor antagonists. Accordingly, in one of its method aspects, this invention provides a method for treating a mammal having a medical condition alleviated by treatment with a muscarinic receptor antagonist, the method comprising administering to the mammal a therapeutically effective amount of a pharmaceutical composition comprising a pharmaceutically-acceptable carrier and a compound of formula I, or a pharmaceutically-acceptable salt or solvate or stereoisomer thereof.

The compounds of this invention can also be used as research tools, i.e., to study biological systems or samples, or to discover new muscarinic receptor antagonists. Accordingly, in another of its method aspects, this invention is directed to a method of antagonizing a muscarinic receptor in a biological system or sample, the method comprising contacting a biological system or sample comprising a muscarinic receptor with a muscarinic receptor-antagonizing amount of a compound of formula I, or a pharmaceutically-acceptable salt or solvate or stereoisomer thereof.

This invention is also directed to processes for preparing compounds of formula I or a salt thereof. Accordingly, in another of its method aspects, this invention provides a process for preparing a compound of formula I, or a salt or stereoisomer or protected derivative thereof; the process comprising reacting a compound of formula Va, or a salt or stereoisomer or protected derivative thereof; with a compound of formula VIII, or a salt or protected derivative thereof; and a reducing agent to provide a compound of formula I or a salt or protected derivative thereof.

In a preferred embodiment, the above process further comprises the step of forming a pharmaceutically-accept-able salt of a compound of formula I. This invention is also directed to the other processes described herein; and to the product prepared by any of the processes described herein.

This invention is also directed to a compound of formula I, or a pharmaceutically-acceptable salt or solvate or stereoisomer thereof, for use in therapy or as a medicament.

Additionally, this invention is directed to the use of a compound of formula I, or a pharmaceutically-acceptable salt or solvate or stereoisomer thereof, for the manufacture of a medicament; especially for the manufacture of a medicament for the treatment of a medical condition which is alleviated by treatment with a muscarinic receptor antagonist, such as overactive bladder.

DETAILED DESCRIPTION OF THE INVENTION

This invention provides novel substituted 4-amino-1-(pyridylmethyl)-piperidine and related compounds of formula I or pharmaceutically-acceptable salts or solvates or stereoisomers thereof. These compounds may contain one or more chiral centers and, when such a chiral center or centers are present, this invention is directed to racemic mixtures; pure stereoisomers (i.e., individual enantiomers or diastereomers); and stereoisomer-enriched mixtures of such isomers, unless otherwise indicated. When a particular stereoisomer is shown, it will be understood by those skilled in the art that minor amounts of other stereoisomers may be present in the compositions of this invention unless otherwise indicated, provided that the utility of the composition as a whole is not eliminated by the presence of such other isomers.

The compounds of this invention also contain several basic groups (e.g., amino groups) and therefore, the compounds of formula I can exist in various salt forms. All such salt forms are included within the scope of this invention. Also, included within the scope of this invention are pharmaceutically-acceptable solvates of the compounds of formula I or the salts thereof.

Additionally, all cis-trans or E/Z isomers (geometric isomers) and tautomeric forms of the compounds of formula I are included within the scope of this invention. For example, when $R^3$ is hydrogen and X is N, then such compounds may exist in the pyridin-4-one form.

The nomenclature used to describe the compounds of this invention is illustrated by the following representative example. The name 4-{N-[7-(3-(S)-1-carbamoyl-1,1-diphenylmethyl)pyrrolidin-1-yl)hept-1-yl]-N-(ethyl)amino}-1-(4-methoxypyrid-3-ylmethyl)piperidine designates a compound of the formula:

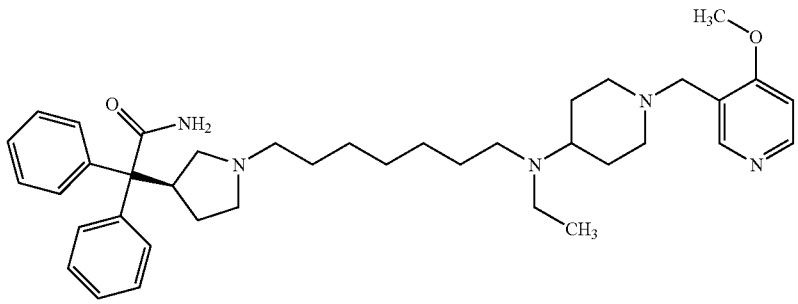

This compound can also be named using AutoNom (MDL, San Leandro Calif.) as follows: 2-[(S)-1-(7-{ethyl-[1-(4-methoxypyridin-3-ylmethyl)piperidin-4-yl]amino}heptyl)pyrrolidin-3-yl]-2,2-diphenylacetamide.

REPRESENTATIVE EMBODIMENTS

The following substituents and values are intended to provide representative examples and embodiments of various aspects of this invention. These representative values are intended to further define such aspects and embodiments and are not intended to exclude other embodiments or limit the scope of this invention. In this regard, the representation that a particular value or substituent is preferred is not intended in any way to exclude other values or substituents from this invention unless specifically indicated.

In the compounds of this invention, $R^1$ is a group of the formula $-(CH_2)_a-(O)_b-(CH_2)_c-$, wherein a, b and c are as defined herein. In one preferred embodiment, $R^1$ is $-(CH_2)_{a+c}-$, i.e., where b is 0, and a and c are as defined herein. In another preferred embodiment, $R^1$ is $-(CH_2)_a-O-(CH_2)_c-$, i.e., where b is 1, and a and c are as defined herein.

Preferred $R^1$ groups include $-(CH_2)_7-$, $-(CH_2)_8-$, $-(CH_2)_9-$, $-(CH_2)_2-O-(CH_2)_4-$, $-(CH_2)_2-O-(CH_2)_5-$, $-(CH_2)_2-O-(CH_2)_6-$, $-(CH_2)_3-O-(CH_2)_3-$, $-(CH_2)_3-O-(CH_2)_4-$, $-(CH_2)_3-O-(CH_2)_5-$, $-(CH_2)_4-O-(CH_2)_2-$, $-(CH_2)_4-O-(CH_2)_3-$, $-(CH_2)_4-O-(CH_2)_4-$, $-(CH_2)_5-O-(CH_2)_2-$, $-(CH_2)_5-O-(CH_2)_3-$ and $-(CH_2)_6-O-(CH_2)_2-$.

Particularly preferred $R^1$ groups include $-(CH_2)_7-$, $-(CH_2)_8-$, $-(CH_2)_9-$, $-(CH_2)_3-O-(CH_2)_3-$ and $-(CH_2)_4-O-(CH_2)_4-$. An especially preferred $R^1$ group is $-(CH_2)_7-$.

In $R^1$, each $-CH_2-$ group is optionally substituted with 1 or 2 substituents selected from the group consisting of methyl, ethyl and fluoro, wherein the methyl and ethyl groups are optionally substituted with 1 to 3 fluoro substituents. Representative substituents include fluoro, methyl, fluoromethyl, difluoromethyl, trifluoromethyl, 2,2,2-trifluoroethyl and the like.

In a preferred embodiment, $R^2$ is $C_{1-4}$ alkyl; more preferably, $R^2$ is $C_{2-3}$ alkyl; wherein the alkyl group is optionally substituted with 1 to 3 fluoro substituents. Particularly preferred $R^2$ groups in this embodiment are methyl, ethyl, n-propyl, isopropyl, n-butyl and isobutyl. Especially preferred $R^2$ groups are ethyl, n-propyl and isopropyl.

In another preferred embodiment, $R^2$ is —$CH_2$—$R^5$, wherein $R^5$ is as defined herein. In this embodiment, $R^2$ (i.e., —$CH_2$—$R^5$) is preferably selected from the group consisting of:

(a) —$CH_2$—($C_{3-5}$ cycloalkyl); and more preferably, —$CH_2$—($C_3$ cycloalkyl); wherein the cycloalkyl group is optionally substituted with 1 to 3 fluoro substituents;

(b) —$CH_2$-(phenyl), i.e., benzyl, wherein the phenyl group is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents;

(c) —$CH_2$-(naphthyl); wherein the naphthyl group (i.e., a 1- or 2-naphthyl group) is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents;

(d) —$CH_2$-(biphenyl), wherein each phenyl ring of the biphenyl group (i.e., a 1,2-, 1,3- or 1,4-biphenyl group) is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents;

(e) —$CH_2$-(pyridyl); wherein the pyridyl group (i.e., a 2-, 3- or 4-pyridyl group) is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents; and (f) —$CH_2C(O)$-(phenyl), i.e., phenacyl, wherein the phenyl ring of the phenacyl group is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents.

Particularly preferred $R^2$ groups in this embodiment include cyclopropylmethyl, cyclobutylmethyl and cyclopentylmethyl; and benzyl, 4-cyanobenzyl, 4-methylbenzyl, 4-trifluoromethoxybenzyl, 4-difluoromethoxybenzyl, 4-thiomethoxybenzyl, 4-methanesulfonylbenzyl, 4-tert-butylbenzyl, 4-phenylbenzyl, pyridyl-2-ylmethyl, pyrid-3-ylmethyl, napthth-2-ylmethyl, 3-cyanophenacyl, and 3,4-ethylenedioxyphenacyl.

In yet another preferred embodiment, $R^2$ is —$(CH_2)_x$—$R^6$, wherein x is 2, 3 or 4; preferably 2 or 3. In this embodiment, $R^2$ (i.e., —$(CH_2)_x$—$R^6$) is preferably selected from the group consisting of:

(a) —$(CH_2)_x$—OH;

(b) —$(CH_2)_x$—O($C_{1-4}$ alkyl); more preferably, —$(CH_2)_x$—O($C_{1-3}$ alkyl); and still more preferably, —$(CH_2)_x$—O($C_{1-2}$ alkyl); wherein the alkyl group is optionally substituted with 1 to 3 fluoro substituents;

(c) —$(CH_2)_x$—S($C_{1-4}$ alkyl), —$(CH_2)_x$—S(O)($C_{1-4}$ alkyl), or —$(CH_2)_x$—S(O)$_2$($C_{1-4}$ alkyl); more preferably, —$(CH_2)_x$—S($C_{1-3}$ alkyl), —$(CH_2)_x$—S(O)($C_{1-3}$ alkyl), or —$(CH_2)_x$—S(O)$_2$($C_{1-3}$ alkyl); and still more preferably, —$(CH_2)_x$—S($C_{1-2}$ alkyl), —$(CH_2)_x$—S(O)($C_{1-2}$ alkyl), or —$(CH_2)_x$—S(O)$_2$($C_{1-2}$ alkyl); wherein the alkyl group is optionally substituted with 1 to 3 fluoro substituents;

(d) —$(CH_2)_x$-(phenyl), e.g., phenethyl, wherein the phenyl group is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents;

(e) —$(CH_2)_x$—(O-phenyl), wherein the phenyl group is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents;

(f) —$(CH_2)_x$-(naphthyl), wherein the naphthyl group (i.e., a 1- or 2-naphthyl group) is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents; and (g) —$(CH_2)_x$-(indolyl), wherein the indolyl group (i.e., a 2- or 3-indolyl group) is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substitutents.

For this embodiment, preferred $R^2$ groups include 2-hydroxyethyl, 2-methoxyethyl, 2-(methylthio)ethyl, 2-ethoxyethyl, 2-(ethylthio)ethyl, 2-(2,2,2-trifluoroethoxy)ethyl, 2-phenethyl, 2-(naphth-1-yl)ethyl, 2-(indol-3-yl)ethyl, 3-hydroxypropyl, 3-methoxypropyl, 3-ethoxypropyl, 3-phenylpropyl and 3-phenoxypropyl.

In a preferred embodiment, $R^2$ is $C_{1-4}$ alkyl, —$CH_2$—($C_{3-5}$ alkyl), —$CH_2$—($C_{3-5}$ cycloalkyl), —$CH_2CH_2$—OH or —$CH_2CH_2$—O($C_{1-4}$ alkyl).

More preferably, $R^2$ is ethyl, n-propyl, isopropyl, cyclopropylmethyl or 2-hydroxyethyl.

Preferably, each $R^3$ is independently selected from the group consisting of hydrogen, $C_{1-4}$ alkyl, cyclopropylmethyl and 2-hydroxyethyl; wherein each alkyl group is optionally substituted with 1 to 5 fluoro substituents. More preferably, each $R^3$ is hydrogen or $C_{1-4}$ alkyl; wherein each alkyl group is optionally substituted with 1 to 4 fluoro substitutents. Still more preferably, each $R^3$ is independently $C_{1-3}$ alkyl optionally substituted with 1 to 4 fluoro substitutents. Still more preferably, each $R^3$ is methyl.

Particularly preferred $R^3$ groups include hydrogen, methyl, ethyl, n-propyl, isopropyl, difluoromethyl, trifluoromethyl, 2,2,2-trifluoroethyl, 1,3-difluoroprop-2-yl, 1,1,3-trifluoroprop-2-yl, and 1,1,3,3-tetrafluoroprop-2-yl.

Preferably, $R^4$ is selected from the group consisting of $C_{1-4}$ alkyl, —$OR^3$ and halo; wherein $R^3$ is as defined herein including its preferred embodiments and wherein the alkyl group is optionally substituted with 1 to 5 fluoro substituents. More preferably, $R^4$ is $C_{1-3}$ alkyl, —$OR^3$, fluoro and chloro; wherein the alkyl group is optionally substituted with 1 to 3 fluoro substitutents. Still more preferably, $R^4$ is $C_{1-2}$ alkyl, —$OR^3$, fluoro or chloro. Still more preferably, $R^4$ is methyl, —$OR^3$, fluoro or chloro. In a preferred embodiment, $R^4$ is —$OR^3$.

In the compounds of this invention, one or two of W, X, Y and Z are N or N→O. In a preferred embodiment, one and only one of W, X, Y and Z is N or N→O, i.e., the ring containing W, X, Y and Z is a pyridine or pyridine N-oxide ring. In separate embodiments of this aspect of the invention, W, X, Y and Z are defined as follows:

(a) W is N; X is CH; Y is CH; and Z is CH;
(b) W is CH or $CR^4$; X is N; Y is CH and Z is CH;
(c) W is CH or $CR^4$; X is CH; Y is N; and Z is CH;
(d) W is CH or $CR^4$; X is CH; Y is CH; and Z is N; or
(e) W is CH; X is N; Y is CH and Z is CH.

In other preferred embodiments, two of W, X, Y and Z are N or N→O, i.e., the ring containing W, X, Y and Z is a pyridazine, pyrimidine or pyrazine ring or the corresponding N-oxides.

Preferably, when W, X, Y and Z are not CH or $CR^4$, they are N.

Preferably, when X, Y and Z are not N or N→O, they are CH.

In the compounds of formula I, the —$CH_2$— group attached to the piperidine nitrogen atom and the pyridine ring containing W, X, Y and Z, is optionally substituted with 1 or 2 substituents selected from the group consisting of methyl, ethyl and fluoro, wherein the methyl and ethyl groups are optionally substituted with 1 to 3 fluoro substituents. Representative substituents include fluoro, methyl, fluoromethyl, difluoromethyl, trifluoromethyl, 2,2,2-trifluoroethyl and the like.

When present, each $R^a$ or $R^b$ is preferably independently selected from the group consisting of $C_{1-4}$ alkyl, fluoro, chloro and —$OR^f$; wherein each alkyl group is optionally substituted with 1 to 3 fluoro substituents. More preferably, each $R^a$ and $R^b$ is $C_{1-2}$ alkyl or fluoro. Particularly preferred $R^a$ and $R^b$ groups include methyl, ethyl, n-propyl, isopropyl, difluoromethyl, trifluoromethyl, 2,2,2-trifluoroethyl, fluoro, chloro, methoxy, ethoxy, difluoromethoxy and trifluoromethoxy.

When present, each $R^c$ or $R^d$ is preferably independently selected from the group consisting of $C_{1-2}$ alkyl and fluoro; wherein each alkyl group is optionally substituted with 1 to 3 fluoro substitutents. When two $R^c$ or $R^d$ substituents are present, they can be on the same or different carbon atoms. Particularly preferred $R^c$ and $R^d$ groups include methyl, ethyl, difluoromethyl, trifluromethyl and fluoro.

Preferably, each $R^e$ is independently hydrogen or $C_{1-4}$ alkyl. More preferably, each $R^e$ is independently hydrogen or $C_{1-2}$ alkyl. Still more preferably, each $R^e$ is hydrogen. Particularly preferred $R^e$ groups include hydrogen, methyl and ethyl.

Alternatively, both $R^e$ groups are joined together with the nitrogen atom to which they are attached to form $C_{5-6}$ heterocyclic ring optionally containing one additional heteroatom selected from nitrogen, oxygen or sulfur. Particularly preferred heterocyclic rings include pyrrolidin-1-yl, piperidin-1-yl, piperazin-1-yl, morpholin-4-yl and thiomorpholin-4-yl Preferably, each $R^i$ is independently phenyl; wherein each phenyl group is optionally substituted with 1 to 3 substituents independently selected from $R^k$.

Preferably, each $R^j$ is independently selected from the group consisting of phenyl, —OH and —O($C_{1-2}$ alkyl); wherein each alkyl group is optionally substituted with 1 to 3 fluoro substitutents; and each phenyl group is optionally substituted with 1 to 3 substituents independently selected from $R^k$.

Preferably, m is 0, 1 or 2; more preferably, m is 0 or 1; and still more preferably, m is 0.

Preferably, n is 0, 1 or 2; more preferably, n is 0 or 1; and still more preferably, n is 0.

Preferably, p is 1.

When p is 1, i.e., when the ring defined by p is a pyrrolidine ring, then in one preferred embodiment, the stereocenter at the 3-position of the pyrrolidine ring (i.e., the carbon atom bearing the 1-carbamoyl-1,1-diphenylmethyl group) preferable has the (S) stereochemistry. In another preferred embodiment, this stereocenter has the (R) stereochemistry.

Preferably, q is 0.
Preferably, r is 0.
Preferably, x is 2 or 3.
Preferably, y is 2 or 3.

A preferred group of compounds are compounds of formula I wherein $R^1$ is —$(CH_2)_7$—, —$(CH_2)_8$— or —$(CH_2)_9$—; $R^3$ is methyl; W is CH; X is N; Y is CH; Z is CH; both $R^e$ are hydrogen; m, n, q and r are 0; p is 1; and $R^2$ is as defined herein including its preferred embodiments; or a pharmaceutically-acceptable salt or solvate or stereoisomer thereof.

Another preferred group of compounds are compounds of formula I wherein $R^1$ is —$(CH_2)_7$—, —$(CH_2)_8$— or —$(CH_2)_9$—; $R^3$ is ethyl; W is CH; X is N; Y is CH; Z is CH; both $R^e$ are hydrogen; m, n, q and r are 0; p is 1; and $R^2$ is as defined herein including its preferred embodiments; or a pharmaceutically-acceptable salt or solvate or stereoisomer thereof.

Another preferred group of compounds are compounds of formula I wherein $R^1$ is —$(CH_2)_7$—, —$(CH_2)_8$— or —$(CH_2)_9$—; $R^2$ is isopropyl; W is CH; X is N; Y is CH; Z is CH; both $R^e$ are hydrogen; m, n, q and r are 0; p is 1; and $R^3$ is as defined herein including its preferred embodiments; or a pharmaceutically-acceptable salt or solvate or stereoisomer thereof.

Still another preferred group of compounds are compounds of formula I wherein $R^2$ is isopropyl; $R^3$ is methyl; W is CH; X is N; Y is CH; Z is CH; both Re are hydrogen; m, n, q and r are 0; p is 1; and $R^1$ is as defined herein including its preferred embodiments; or a pharmaceutically-acceptable salt or stereoisomer thereof.

Yet another preferred group of compounds are compounds of formula I wherein $R^2$ is isopropyl; $R^3$ is ethyl; W is CH; X is N; Y is CH; Z is CH; both $R^e$ are hydrogen; m, n, q and r are 0; p is 1; and $R^1$ is as defined herein including its preferred embodiments; or a pharmaceutically-acceptable salt or stereoisomer thereof.

Another preferred group of compounds are compounds of formula IX:

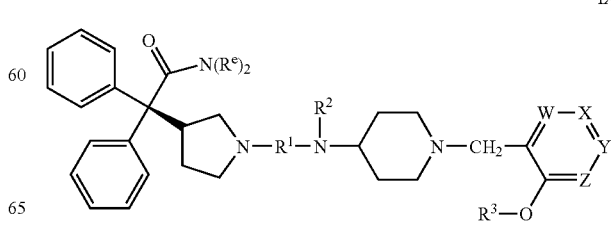

IX wherein $R^1$, $R^2$, $R^3$, W, X, Y and Z are as defined in Table I, and each $R^e$ is hydrogen unless indicated otherwise in Table I, or a pharmaceutically-acceptable salt or solvate or stereoisomer thereof.

TABLE I

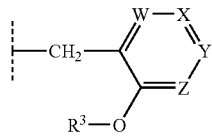

| Ex. No. | $R^1$ | $R^2$ | $R^3$—O |
|---|---|---|---|
| 1 | —(CH$_2$)$_7$— | isopropyl | (4-methoxypyrid-3-yl)methyl |
| 2 | —(CH$_2$)$_3$—O—(CH$_2$)$_3$— | isopropyl | (4-methoxypyrid-3-yl)methyl |
| 3 | —(CH$_2$)$_4$—O—(CH$_2$)$_2$— | isopropyl | (4-methoxypyrid-3-yl)methyl |
| 4 | —(CH$_2$)$_7$— | ethyl | (2-methoxypyrid-3-yl)methyl |
| 5 | —(CH$_2$)$_7$— | ethyl | (3-methoxypyrid-2-yl)methyl |
| 6 | —(CH$_2$)$_7$— | ethyl | (4-methoxypyrid-3-yl)methyl |
| 7 | —(CH$_2$)$_3$—O—(CH$_2$)$_3$— | ethyl | (4-methoxypyrid-3-yl)methyl |
| 8 | —(CH$_2$)$_8$— | ethyl | (4-methoxypyrid-3-yl)methyl |
| 9 | —(CH$_2$)$_9$— | ethyl | (4-methoxypyrid-3-yl)methyl |
| 10 | —(CH$_2$)$_2$—O—(CH$_2$)$_4$— | ethyl | (4-methoxypyrid-3-yl)methyl |
| 11 | —(CH$_2$)$_2$—O—(CH$_2$)$_5$— | ethyl | (4-methoxypyrid-3-yl)methyl |
| 12 | —(CH$_2$)$_2$—O—(CH$_2$)$_6$— | ethyl | (4-methoxypyrid-3-yl)methyl |
| 13 | —(CH$_2$)$_3$—O—(CH$_2$)$_4$— | ethyl | (4-methoxypyrid-3-yl)methyl |
| 14 | —(CH$_2$)$_3$—O—(CH$_2$)$_5$— | ethyl | (4-methoxypyrid-3-yl)methyl |
| 15 | —(CH$_2$)$_4$—O—(CH$_2$)$_2$— | ethyl | (4-methoxypyrid-3-yl)methyl |
| 16 | —(CH$_2$)$_4$—O—(CH$_2$)$_3$— | ethyl | (4-methoxypyrid-3-yl)methyl |
| 17 | —(CH$_2$)$_4$—O—(CH$_2$)$_4$— | ethyl | (4-methoxypyrid-3-yl)methyl |
| 18 | —(CH$_2$)$_5$—O—(CH$_2$)$_2$— | ethyl | (4-methoxypyrid-3-yl)methyl |
| 19 | —(CH$_2$)$_5$—O—(CH$_2$)$_3$— | ethyl | (4-methoxypyrid-3-yl)methyl |
| 20 | —(CH$_2$)$_6$—O—(CH$_2$)$_2$— | ethyl | (4-methoxypyrid-3-yl)methyl |
| 21 | —(CH$_2$)$_7$— | n-propyl | (4-methoxypyrid-3-yl)methyl |
| 22 | —(CH$_2$)$_8$— | n-propyl | (4-methoxypyrid-3-yl)methyl |
| 23 | —(CH$_2$)$_9$— | n-propyl | (4-methoxypyrid-3-yl)methyl |
| 24 | —(CH$_2$)$_2$—O—(CH$_2$)$_4$— | n-propyl | (4-methoxypyrid-3-yl)methyl |
| 25 | —(CH$_2$)$_2$—O—(CH$_2$)$_5$— | n-propyl | (4-methoxypyrid-3-yl)methyl |
| 26 | —(CH$_2$)$_2$—O—(CH$_2$)$_6$— | n-propyl | (4-methoxypyrid-3-yl)methyl |
| 27 | —(CH$_2$)$_3$—O—(CH$_2$)$_3$— | n-propyl | (4-methoxypyrid-3-yl)methyl |
| 28 | —(CH$_2$)$_3$—O—(CH$_2$)$_4$— | n-propyl | (4-methoxypyrid-3-yl)methyl |
| 29 | —(CH$_2$)$_3$—O—(CH$_2$)$_5$— | n-propyl | (4-methoxypyrid-3-yl)methyl |
| 30 | —(CH$_2$)$_4$—O—(CH$_2$)$_2$— | n-propyl | (4-methoxypyrid-3-yl)methyl |
| 31 | —(CH$_2$)$_4$—O—(CH$_2$)$_3$— | n-propyl | (4-methoxypyrid-3-yl)methyl |
| 32 | —(CH$_2$)$_4$—O—(CH$_2$)$_4$— | n-propyl | (4-methoxypyrid-3-yl)methyl |
| 33 | —(CH$_2$)$_5$—O—(CH$_2$)$_2$— | n-propyl | (4-methoxypyrid-3-yl)methyl |
| 34 | —(CH$_2$)$_5$—O—(CH$_2$)$_3$— | n-propyl | (4-methoxypyrid-3-yl)methyl |
| 35 | —(CH$_2$)$_6$—O—(CH$_2$)$_2$— | n-propyl | (4-methoxypyrid-3-yl)methyl |
| 36 | —(CH$_2$)$_7$— | isopropyl | (4-n-propoxypyrid-3-yl)methyl |
| 37 | —(CH$_2$)$_7$— | isopropyl | (4-isopropoxypyrid-3-yl)methyl |
| 38 | —(CH$_2$)$_7$— | isopropyl | (4-cyclopropylmethoxypyrid-3-yl)methyl |
| 39 | —(CH$_2$)$_7$— | isopropyl | {4-(2-hydroxyethoxy)pyrid-3-yl}methyl |
| 40 | —(CH$_2$)$_7$— | isopropyl | (4-isobutoxypyrid-3-yl)methyl |
| 41 | —(CH$_2$)$_7$— | isopropyl | (2,4-dimethoxypyrid-3-yl)methyl |
| 42 | —(CH$_2$)$_7$— | isopropyl | (2-fluoro-4-methoxypyrid-3-yl)methyl |
| 43 | —(CH$_2$)$_7$— | isopropyl | (2-chloro-4-methoxypyrid-3-yl)methyl |
| 44 | —(CH$_2$)$_7$— | isopropyl | (2-methyl-4-methoxypyrid-3-yl)methyl |
| 45 | —(CH$_2$)$_8$— | isopropyl | (4-methoxypyrid-3-yl)methyl |
| 46 | —(CH$_2$)$_9$— | isopropyl | (4-methoxypyrid-3-yl)methyl |
| 47 | —(CH$_2$)$_7$— | isopropyl | (3-methoxypyrid-2-yl)methyl |
| 48 | —(CH$_2$)$_8$— | isopropyl | (3-methoxypyrid-2-yl)methyl |
| 49 | —(CH$_2$)$_9$— | isopropyl | (3-methoxypyrid-2-yl)methyl |
| 50 | —(CH$_2$)$_7$— | isopropyl | (3-methoxypyrid-4-yl)methyl |
| 51 | —(CH$_2$)$_8$— | isopropyl | (3-methoxypyrid-4-yl)methyl |
| 52 | —(CH$_2$)$_9$— | isopropyl | (3-methoxypyrid-4-yl)methyl |
| 53 | —(CH$_2$)$_7$— | isopropyl | (2-methoxypyrid-3-yl)methyl |
| 54 | —(CH$_2$)$_8$— | isopropyl | (2-methoxypyrid-3-yl)methyl |
| 55 | —(CH$_2$)$_9$— | isopropyl | (2-methoxypyrid-3-yl)methyl |
| 56 | —(CH$_2$)$_2$—O—(CH$_2$)$_4$— | isopropyl | (4-methoxypyrid-3-yl)methyl |
| 57 | —(CH$_2$)$_2$—O—(CH$_2$)$_5$— | isopropyl | (4-methoxypyrid-3-yl)methyl |

TABLE I-continued

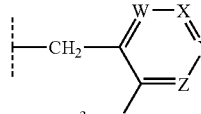

| Ex. No. | R¹ | R² | R³ |
|---|---|---|---|
| 58 | —(CH₂)₂—O—(CH₂)₆— | isopropyl | (4-methoxypyrid-3-yl)methyl |
| 59 | —(CH₂)₃—O—(CH₂)₄— | isopropyl | (4-methoxypyrid-3-yl)methyl |
| 60 | —(CH₂)₃—O—(CH₂)₅— | isopropyl | (4-methoxypyrid-3-yl)methyl |
| 61 | —(CH₂)₄—O—(CH₂)₃— | isopropyl | (4-methoxypyrid-3-yl)methyl |
| 62 | —(CH₂)₄—O—(CH₂)₄— | isopropyl | (4-methoxypyrid-3-yl)methyl |
| 63 | —(CH₂)₅—O—(CH₂)₂— | isopropyl | (4-methoxypyrid-3-yl)methyl |
| 64 | —(CH₂)₅—O—(CH₂)₃— | isopropyl | (4-methoxypyrid-3-yl)methyl |
| 65 | —(CH₂)₆—O—(CH₂)₂— | isopropyl | (4-methoxypyrid-3-yl)methyl |
| 66 | —(CH₂)₇— | cyclopropylmethyl | (4-methoxypyrid-3-yl)methyl |
| 67 | —(CH₂)₈— | cyclopropylmethyl | (4-methoxypyrid-3-yl)methyl |
| 68 | —(CH₂)₉— | cyclopropylmethyl | (4-methoxypyrid-3-yl)methyl |
| 69 | —(CH₂)₂—O—(CH₂)₄— | cyclopropylmethyl | (4-methoxypyrid-3-yl)methyl |
| 70 | —(CH₂)₂—O—(CH₂)₅— | cyclopropylmethyl | (4-methoxypyrid-3-yl)methyl |
| 71 | —(CH₂)₂—O—(CH₂)₆— | cyclopropylmethyl | (4-methoxypyrid-3-yl)methyl |
| 72 | —(CH₂)₃—O—(CH₂)₃— | cyclopropylmethyl | (4-methoxypyrid-3-yl)methyl |
| 73 | —(CH₂)₃—O—(CH₂)₄— | cyclopropylmethyl | (4-methoxypyrid-3-yl)methyl |
| 74 | —(CH₂)₃—O—(CH₂)₅— | cyclopropylmethyl | (4-methoxypyrid-3-yl)methyl |
| 75 | —(CH₂)₄—O—(CH₂)₂— | cyclopropylmethyl | (4-methoxypyrid-3-yl)methyl |
| 76 | —(CH₂)₄—O—(CH₂)₃— | cyclopropylmethyl | (4-methoxypyrid-3-yl)methyl |
| 77 | —(CH₂)₄—O—(CH₂)₄— | cyclopropylmethyl | (4-methoxypyrid-3-yl)methyl |
| 78 | —(CH₂)₅—O—(CH₂)₂— | cyclopropylmethyl | (4-methoxypyrid-3-yl)methyl |
| 79 | —(CH₂)₅—O—(CH₂)₃— | cyclopropylmethyl | (4-methoxypyrid-3-yl)methyl |
| 80 | —(CH₂)₆—O—(CH₂)₂— | cyclopropylmethyl | (4-methoxypyrid-3-yl)methyl |
| 81 | —(CH₂)₇— | 2-hydroxyethyl | (4-methoxypyrid-3-yl)methyl |
| 82 | —(CH₂)₈— | 2-hydroxyethyl | (4-methoxypyrid-3-yl)methyl |
| 83 | —(CH₂)₉— | 2-hydroxyethyl | (4-methoxypyrid-3-yl)methyl |
| 84 | —(CH₂)₂—O—(CH₂)₄— | 2-hydroxyethyl | (4-methoxypyrid-3-yl)methyl |
| 85 | —(CH₂)₂—O—(CH₂)₅— | 2-hydroxyethyl | (4-methoxypyrid-3-yl)methyl |
| 86 | —(CH₂)₂—O—(CH₂)₆— | 2-hydroxyethyl | (4-methoxypyrid-3-yl)methyl |
| 87 | —(CH₂)₃—O—(CH₂)₃— | 2-hydroxyethyl | (4-methoxypyrid-3-yl)methyl |
| 88 | —(CH₂)₃—O—(CH₂)₄— | 2-hydroxyethyl | (4-methoxypyrid-3-yl)methyl |
| 89 | —(CH₂)₃—O—(CH₂)₅— | 2-hydroxyethyl | (4-methoxypyrid-3-yl)methyl |
| 90 | —(CH₂)₄—O—(CH₂)₂— | 2-hydroxyethyl | (4-methoxypyrid-3-yl)methyl |
| 91 | —(CH₂)₄—O—(CH₂)₃— | 2-hydroxyethyl | (4-methoxypyrid-3-yl)methyl |
| 92 | —(CH₂)₄—O—(CH₂)₄— | 2-hydroxyethyl | (4-methoxypyrid-3-yl)methyl |
| 93 | —(CH₂)₅—O—(CH₂)₂— | 2-hydroxyethyl | (4-methoxypyrid-3-yl)methyl |
| 94 | —(CH₂)₅—O—(CH₂)₃— | 2-hydroxyethyl | (4-methoxypyrid-3-yl)methyl |
| 95 | —(CH₂)₆—O—(CH₂)₂— | 2-hydroxyethyl | (4-methoxypyrid-3-yl)methyl |
| 96 | —(CH₂)₇— | isopropyl | (4-tert-butoxypyrid-3-yl)methyl |
| 97 | —(CH₂)₇— | isopropyl | (4-hydroxypyrid-3-yl)methyl[1] |
| 98 | —(CH₂)₇— | isopropyl | (4-ethoxypyrid-3-yl)methyl |
| 99 | —(CH₂)₇— | isopropyl | (4-trifluoromethoxypyrid-3-yl)methyl |
| 100 | —(CH₂)₇— | isopropyl | (4-difluoromethoxypyrid-3-yl)methyl |
| 101 | —(CH₂)₇— | isopropyl | (4-methoxy-2-trifluoro-methoxypyrid-3-yl)methyl |
| 102 | —(CH₂)₇— | isopropyl | (2-difluoromethoxy-4-methoxypyrid-3-yl)methyl |
| 103 | —(CH₂)₇— | isopropyl | (2-methox-4-trifluoro-methoxyypyrid-3-yl)methyl |
| 104 | —(CH₂)₇— | isopropyl | (4-difluoromethoxy-2-methoxypyrid-3-yl)methyl |
| 105 | —(CH₂)₇— | isopropyl | {2,4-di(trifluoromethoxy)-pyrid-3-yl}methyl |
| 106 | —(CH₂)₇— | isopropyl | {2,4-di(difluoromethoxy)-pyrid-3-yl}methyl |
| 107 | —(CH₂)₇— | isopropyl | (2-ethoxy-4-trifluoro-methoxypyrid-3-yl)methyl |
| 108 | —(CH₂)₇— | isopropyl | (2-ethoxy-4-difluoromethoxy-pyrid-3-yl)methyl |
| 109 | —(CH₂)₇— | isopropyl | (2,4-diethoxypyrid-3-yl)methyl |
| 110 | —(CH₂)₇— —N(Rᵉ)₂ = —N(H)CH₃ | isopropyl | (4-methoxypyrid-3-yl)methyl |
| 111 | —(CH₂)₇— —N(Rᵉ)₂ = —N(CH₃)₂ | isopropyl | (4-methoxypyrid-3-yl)methyl |
| 112 | —(CH₂)₇— —N(Rᵉ)₂ = —N(H)Et | isopropyl | (4-methoxypyrid-3-yl)methyl |

TABLE I-continued

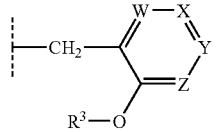

| Ex. No. | R[1] | R[2] | R[3]—O |
|---|---|---|---|
| 113 | —(CH₂)₇—N(Rᵉ)₂ = piperidin-1-yl | isopropyl | (4-methoxypyrid-3-yl)methyl |
| 114 | —(CH₂)₇—N(Rᵉ)₂ = morpholin-4-yl | isopropyl | (4-methoxypyrid-3-yl)methyl |
| 115 | —(CH₂)₇— | isopropyl | [4-(2-fluoroethoxy)pyrid-3-yl)methyl |

[1]In compound 97, the (4-hydroxypyrid-3-yl)methyl group may exist partially or fully as the tautomer, i.e., (pyrid-4-one-3-yl)methyl.

Definitions

When describing the compounds, compositions, methods and processes of this invention, the following terms have the following meanings, unless otherwise indicated.

The term "alkyl" refers to a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" refers to a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenyl" refers to a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like.

The term "alkynyl" refers to a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like.

The term "aryl" refers to a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "cycloalkyl" refers to a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "halo" refers to fluoro, chloro, bromo and iodo.

The term "heteroaryl" refers to a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocyclyl" or "heterocyclic" refers to a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "(4-methoxypyrid-3-yl)methyl" refers to a group of the formula:

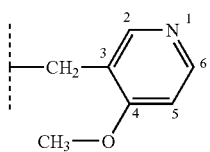

Related pyridyl groups are named in a similar manner.

The term "pyridine N-oxide" refers to a pyridine compound in which the nitrogen atom of the pyridine has been oxidized, i.e., N⁺—O⁻ or N→O.

The term "overactive bladder" or "OAB" refers to a condition characterized symptomatically by urinary urge, urinary incontinence, increased frequency of urination, and/or nightime urination and the like. The term "urinary urge" refers to a strong and sudden desire to void the bladder.

The term "pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids. Salts derived from pharmaceutically-acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically-acceptable acids include acetic, ascorbic, benzenesulfonic, benzoic, camphosulfonic, citric, ethanesulfonic, edisylic, flumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, phosphoric, sulfuric and tartaric acids.

The term "salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

The term "solvate" refers to a complex or aggregate formed by one or more molecules of a solute, i.e. a compound of formula I or a pharmaceutically-acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" refers to an amount sufficient to effect treatment when administered to a patient in need of treatment.

The term "treating" or "treatment" as used herein refers to the treating or treatment of a disease or medical condition (such as overactive bladder) in a patient, such as a mammal (particularly a human or a companion animal) which includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "leaving group" refers to a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected derivatives thereof" refers to a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "amino-protecting group" refers to a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" refers to a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluroenylmethyl (Fm), trimethylsilyl (TMS), tert-butyldimethylsilyl (TBS), diphenylmethyl (benzhydryl, DPM) and the like.

General Synthetic Procedures

The substituted 4-amino-1-(pyridylmethyl)piperidine and related compounds of this invention can be prepared from readily available starting materials using the following general methods and procedures. Although a particular embodiment of the present invention may be shown or described in the Schemes below, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. The optimum reaction conditions may vary with the particular reactants or solvent used, but such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well known in the art. Protecting groups other than those illustrated in the procedures described herein may be used, if desired. For example, numerous protecting groups, and their introduction and removal, are described in T. W.

Greene and G. M. Wuts, *Protecting Groups in Organic Synthesis*, Third Edition, Wiley, New York, 1999, and references cited therein.
In a preferred method of synthesis, the compounds of formula I are prepared as illustrated in Scheme A (the substituents and variables shown in the following Schemes have the definitions provided herein unless otherwise indicated).
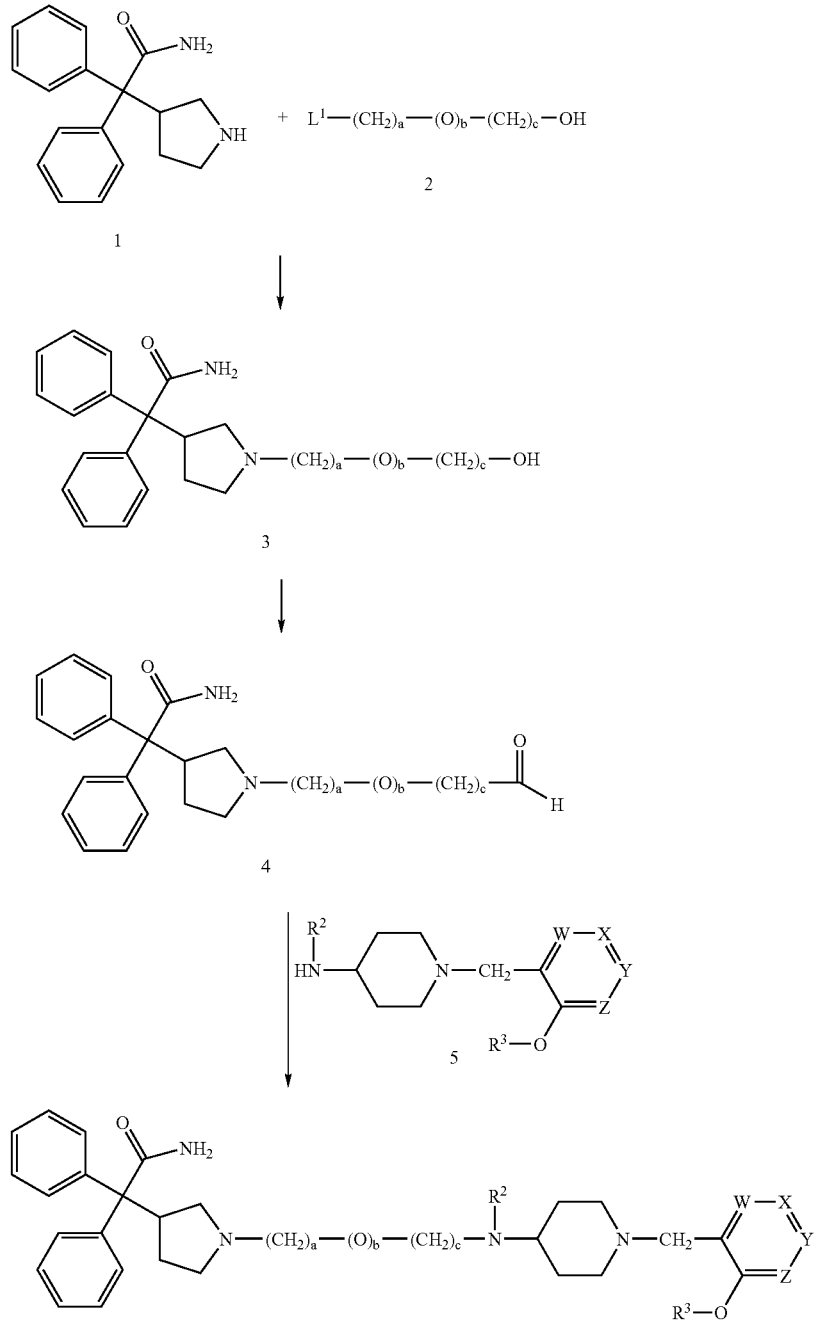

As shown in Scheme A, a compound of formula 1 is first reacted with alcohol 2 where $L^1$ is a suitable leaving group, such as bromo, iodo, tosyl, mesyl and the like, to provide intermediate 3. Typically, this reaction is conducted by contacting 1 with at least one equivalent, preferably with about 1.0 to about 1.1 equivalents, of alcohol 2 in an inert diluent, such as acetonitrile and the like. This reaction is generally conducted in presence of excess base; preferably, in the presence of about 2 to about 4 equivalent of a base, such as a trialkylamine, preferably triethylamine. Typically, this reaction is conducted at a temperature ranging from about 0° C. to about 80° C., preferably about 40 to 50° C., for about 1 to 24 hours, or until the reaction is substantially complete. If desired, the resulting intermediate 3 is readily purified by standard procedures, such as chromatography, recrystallization and the like.

The alcohols of formula 2 used in this reaction are either commercially available or can be prepared from commercially available starting materials and reagents using well-known procedures. Representative alcohols of formula 2 include, by way of example, 7-chloro-1-heptanol, 8-chloro-1-octanol, 9-chloro-1-nonanol, 7-bromo-1-heptanol, 8-bromo-1-octanol, 9-bromo-1-nonanol, 7-iodo-1-heptanol, 8-iodo-1-octanol, 9-iodo-1-nonanol, 7-bromo-3-oxaheptan-1-ol, 7-bromo-4-oxaheptan-1-ol, 7-bromo-5-oxaheptan-1-ol, 8-bromo-3-oxaoctan-1-ol, 8-bromo-4-oxaoctan-1-ol, 8-bromo-5-oxaoctan-1-ol, 8-bromo-6-oxaoctan-1-ol, 8-bromo-3-oxaoctan-1-ol, 9-bromo-3-oxanonan-1-ol, 9-bromo-4-oxanonan-1-ol, 9-bromo-5-oxanonan-1-ol, 9-bromo-6-oxanonan-1-ol, 9-bromo-7-oxanonan-1-ol and the like.

The hydroxyl group of intermediate 3 is then oxidized to the corresponding aldehyde to provide intermediate 4. This reaction is typically conducted by contacting 3 with an excess amount of a suitable oxidizing agent. Any oxidizing agent capable of oxidizing a hydroxyl group to an aldehyde may be used in this reaction including chromium (VI) reagents, such as dipyridine chromium (VI) oxide, pyridinium chlorochromate, pyridinium dichromate and the like; and activated dimethyl sulfoxide reagents, such oxalyl chloride/DMSO, sulfur trioxide pyridine complex/DMSO/trialkylamine and the like.

Preferably, this reaction is conducted using an excess of sulfur trioxide pyridine complex and dimethyl sulfoxide in the presence of a trialkylamine, such as triethylamine, diisopropylethylamine and the like. Typically, this reaction is conducted by contacting 3 with about 2.5 to about 3.5 equivalents of sulfur trioxide pyridine complex and an excess, preferably about 10 equivalents, of dimethyl sulfoxide in the presence of an excess, preferably about 5 equivalents, of diisopropylethylamine in an inert diluent, such as dichloromethane. This reaction is generally conducted at a temperature ranging from about −30° C. to about 0° C., preferably at about −10 to about −20° C., for about 0.25 to about 2 hours, or until the reaction is substantially complete. Optionally, the resulting aldehyde intermediate 4 is then purified using standard procedures, such as chromatography, recrystallization and the like.

Alternatively, aldehyde intermediate 4 can be prepared by first reacting 1 with a compound of the formula:

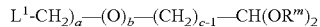

or

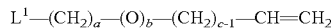

or

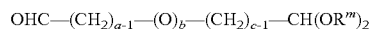

wherein each $L^1$, $R^m$, a, b and c are as defined herein, to provide an intermediate of the formula Vb or Vd. Ozonolysis of the olefin in Vd (i.e., using $O_3$, followed by decomposition of the ozonide with a reducing agent, such as trimethyl phosphite, dimethyl sulfide and the like) then affords aldehyde 4. Alternatively, hydrolysis of the acetal of formula Vb (i.e., using aqueous acid) also affords aldehyde 4.

Aldehyde intermediate 4 is then coupled with 4-amino-1-(pyridylmethyl)piperidine intermediate 5 to afford a compound of formula 6. Typically, this reaction is conducted by contacting aldehyde 4 with about 1.0 to about 1.2 equivalents of 5 in the presence of an excess, preferably about 1.2 to about 1.5 equivalent, of a suitable reducing agent in an inert diluent, such as dichloromethane. Suitable reducing agents include, by way of illustration, sodium triacetoxyborohydride, sodium cyanoborohydride and the like. Preferably, the reducing agent is sodium triacetoxyborohydride. Generally, this reaction is conducted at a temperature ranging from about 0° C. to about 30° C. for about 6 to about 24 hours, or until the reaction is substantially complete. The resulting compound of formula 6 is typically purified using standard procedures, such as chromatography, recrystallization and the like.

If desired, alcohol 3 can also be oxidized to the corresponding carboxylic acid using a strong oxidizing agent, such as chromic acid, permanganate, nitric acid and the like. The resulting carboxylic acid can then be coupled with 4-amino-1-(pyridylmethyl)piperidine intermediate 5 to form an amide and the resulting amide reduced with a reducing agent, such as diisobutylaluminum hydride, to afford compound 6.

The compounds of formula 1 employed in the reactions described herein are readily prepared by the procedures illustrated in Scheme B.

Scheme B

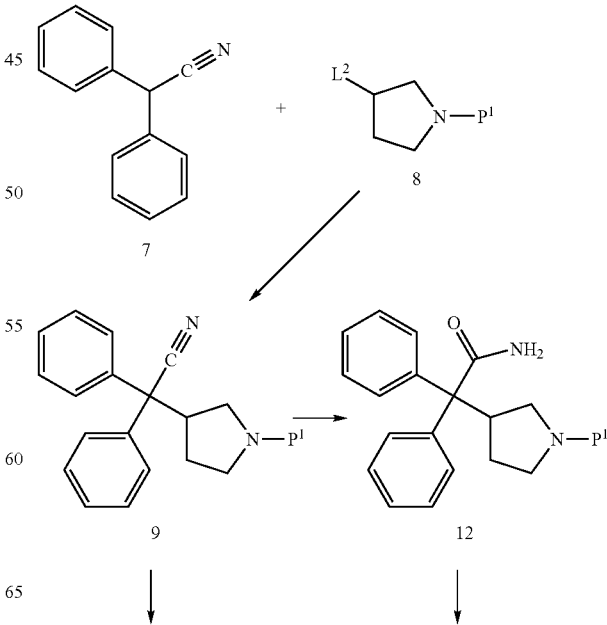

-continued

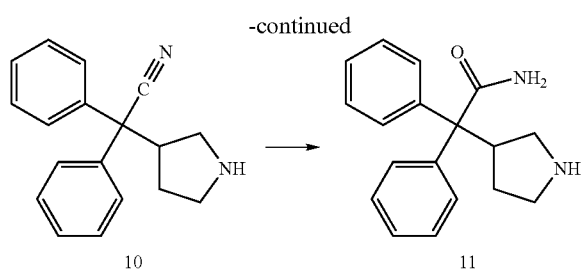

As illustrated in Scheme B, diphenylacetonitrile 7 is reacted with intermediate 8, where L² is a suitable leaving group, such as chloro, bromo, iodo, tosyl, mesyl and the like, and P¹ is an amino-protecting group, such as benzyl, 4-methoxybenzyl, 4-nitrobenzyl, ethoxycarbonyl, phenylcarbonyl and the like, to provide intermediate 9. Typically, this reaction is conducted by first forming the anion of compound 7 by contacting 7 with excess, preferably about 1.4 to about 1.6 equivalents, of a strong base, such as potassium tert-butoxide, in an inert diluent, such as tetrahydrofuran, at a temperature ranging from about −10° C. to about 10° C. for about 0.5 to about 2.0 hours. The resulting anion is then reacted in situ with about 0.95 to about 1.05 equivalents of 8 at a temperature ranging from about 20° C. to about 50° C. for about 10 to about 48 hours, or until the reaction is substantially complete. Compounds of formula 8, where L² is a sulfonate ester leaving group, are readily prepared from the corresponding alcohol using conventional procedures and reagents. For example, (S)-1-benzyl-3-pyrrolidinol is readily converted to (S)-1-benzyl-3-(p-toluenesulfonyloxy) pyrrolidine by treatment with about 1.1 equivalents of p-toluenesulfonyl chloride and about 1.2 equivalents of 1,4-diazabicyclo[2.2.2]octane (DABCO). Other compounds of formula 8 can be prepared by similar procedures using commercially available starting materials and reagents.

Compound 9 is then deprotected using conventional procedures and reagents to afford compound 10. For example, if P¹ in compound 9 is a benzyl protecting group, the benzyl group is readily removed by transfer hydrogenolysis using a hydrogen source, such as ammonium formate, and a catalyst, such as palladium on carbon. Preferably, this reaction is conducted using the hydrochloride or hydrobromide salt of compound 9 or in the presence of an acid, such as hydrochloric acid, hydrobromic acid, formic acid, sulfuric acid, phosphoric acid, p-toluenesulfonic acid, acetic acid, oxalic acid and the like. This hydrogenolysis reaction can also be conducted using hydrogen and a catalyst in the presence of an acid. See, for example, U.S. Pat. No. 6,005,119, issued Dec. 21, 1999 to N. Mori et al.

The nitrile group of compound 10 is then hydrolyzed to the corresponding amide (i.e., —C(O)NH₂) to provide a compound of formula 11. This reaction is typically conducted by contacting 10 with aqueous sulfuric acid, preferably 80% sulfuric acid, at a temperature ranging from about 70° C. to about 100° C., preferably about 90° C., for about 12 to about 36 hours, or until the reaction is substantially complete. As shown in Scheme B, hydrolysis of the nitrile group to the amide can also be performed before removal of the protecting group to afford 12, which can then be deprotected to provide compound 11.

If desired, the nitrile group of compound 9 or 10 can be hydrolyzed to the corresponding carboxylic acid (i.e., —COOH) using, for example, aqueous sodium hydroxide containing about 6 to about 12% hydrogen peroxide. The resulting carboxylic acid can then be coupled to various amines (i.e., R$^e$R$^e$NH, where R$^e$ is as defined herein) to form substititued amides using well-known procedures and reagents.

The 4-aminopiperidine compounds of formula 5 used in the reactions described herein can be prepared by the procedures illustrated in Scheme C.

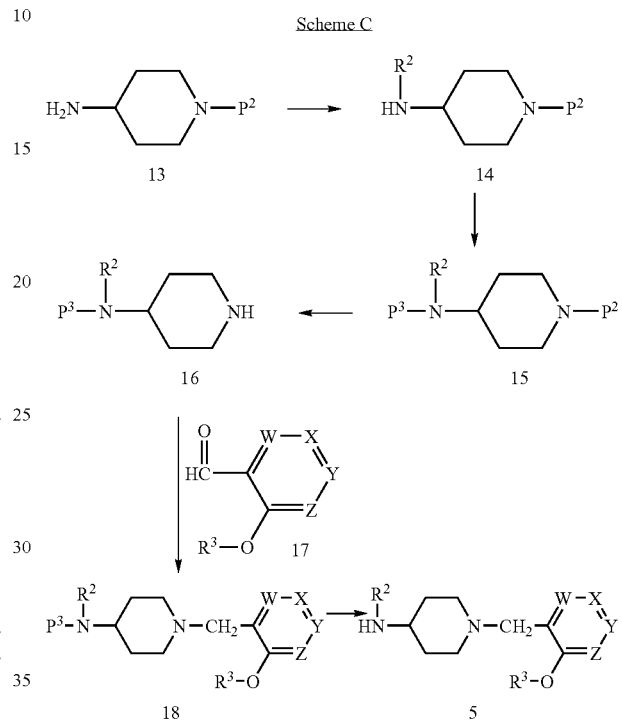

As shown in Scheme C, a compound of formula 13, where p² is an amino protecting group (such as benzyl), is first reductively alkylated with an aldehyde or ketone to provide a compound of formula 14. Compounds of formula 13 are either commercially available or can be prepared from commercially available starting materials using known reagents and procedures. A preferred compound of formula 13 is 4-amino-1-benzylpiperidine which is commercially available from, for example, Aldrich Chemical Company, Inc.

Aldehydes and ketones suitable for use in this reaction include, by way of example, acetaldehyde, propionaldehyde, butyraldehyde, acetone, cyclopropanecarboxaldehyde, and the like.

Typically, this reaction is conducted by contacting 13 with an excess, i.e., at least 1.1 equivalents of the aldehyde or ketone in the presence of an excess, preferably about 1.1 to about 1.3 equivalents, of a suitable reducing agent in an inert diluent, such as methanol. Suitable reducing agents include, by way of illustration, sodium triacetoxyborohydride, sodium cyanoborohydride and the like. Preferably, the reducing agent is sodium triacetoxyborohydride. Generally, this reaction is conducted at a temperature ranging from about 0° C. to about 30° C. for about 1 to about 6 hours, or until the reaction is substantially complete. The resulting compound of formula 14 is typically purified using standard procedures, such as chromatography, recrystallization and the like.

The 4-amino group of the compound of formula 14 is then protected to provide a compound of formula 15, where $P^3$ is an amino-protecting group. Preferably, $P^2$ and $P^3$ are different protecting groups which are selected to allow $P^2$ to be selectively removed in the presence of $P^3$. For example, when $P^2$ is a benzyl group, $P^3$ is preferably a tert-butoxycarbonyl (BOC); benzyloxycarbonyl (Cbz); or 9-fluorenylmethoxycarbonyl (Fmoc) group; or the like. When $P^3$ is a tert-butoxycarbonyl group, compound 15 is typically prepared by contacting 14 with about 1.0 to about 1.2 equivalents of di-tert-butyl dicarbonate in an inert diluent, such as dichloromethane. Typically, this reaction is conducted at a temperature ranging from about 0° C. to about 30° C. for about 6 to about 48 hours, or until the reaction is substantially complete.

Compound 15 is then deprotected using standard procedures and reagents to afford compound 16. For example, when $P^2$ is a benzyl group, the protecting group is removed by hydrogenolysis using a catalyst, such as palladium on carbon. Typically, this reaction is conducted by contacting 15 with hydrogen at a pressure ranging from about 40 to about 60 psi in the presence of a catalyst, such as 10% palladium on carbon. This reaction is generally conducted in an inert diluent, such as ethanol, at ambient temperature for about 12 to 48 hours, or until the reaction is substantially complete.

Compound 16 is then coupled with aldehyde 17 under reductive alkylation conditions to provide compound 18. The aldehydes of formula 17 used in this reaction are commercially available or can be prepared from commercially available starting materials using known reagents and procedures. Representative aldehydes suitable for use in this reaction include, by way of example, 3-methoxypyridine-2-carboxaldehyde, 3-methoxypyridine-4-carboxaldehyde, 2-methoxypyridine-3-carboxaldehyde, 4-methoxypyridine-3-carboxaldehyde; and the like. The preparation of 2-methoxypyridine-3-carboxaldehyde, 3-methoxypyridine-2-carboxaldehyde, 4-methoxypyridine-3-carboxaldehyde from 2-methoxypyridine, 3-methoxypyridine and 4-methoxypyridine, respectively, is described in *J. Org. Chem.*, 1990, 55, 69-73.

Typically, the coupling reaction is conducted by contacting 16 with about 0.9 to about 1.1 equivalents of 17 in an inert diluent, such as dichloromethane, at a temperature ranging from about 0° C. to about 50° C., preferably at ambient temperature, for about 1 to about 6 hours. The resulting imine is typically not isolated, but is reacted in situ with an excess, preferably about 1.1 to about 1.3 equivalents, of a suitable reducing agent. Suitable reducing agents include, by way of example, sodium triacetoxyborohydride, sodium cyanoborohydride and the like. Preferably, the reducing agent is sodium triacetoxyborohydride. Generally, this reduction reaction is conducted at a temperature ranging from about –10° C. to about 25° C. for about 0.5 to about 12 hours, or until the reaction is substantially complete. The resulting compound of formula 18 is typically purified using standard procedures, such as chromatography, recrystallization and the like.

Compound 18 is then deprotected using standard procedures and reagents to afford compound 5. For example, when $P^3$ is a tert-butoxycarbonyl group, the protecting group is removed by treating 18 with aqueous hydrochloric acid in an inert diluent, such as dioxane. Typically, this reaction is conducted by contacting 18 with concentrated hydrochloric acid in dioxane, initially at a temperature of about 0° C. to about 10° C. for about 0.25 to 1 hour, and then at ambient temperature for about 6 to about 24 hours, or until the reaction is substantially complete. The resulting compound of formula 5 is typically purified using standard procedures, such as chromatography, recrystallization and the like.

Alternatively, instead of coupling aldehyde 17 with 16, a carboxylic acid corresponding to 17 can be coupled to 16 using standard coupling reagents and reaction conditions to form an amide. The amide can then be reduced with a reducing agent, such as lithium aluminum hydride, to form intermediate 5.

It will also be appreciated by those skilled in the art that the synthetic steps illustrated in Schemes A, B and C can be conducted in a different order from that shown, or by using different reagents from those described, to produce the compounds of formula 6.

For example, intermediate 14 can be coupled to aldehyde 4 in place of compound 5 using the procedures described herein. After removal of the protecting group (i.e., $P^2$) from the resulting intermediate, aldehyde 17 can be coupled to the piperidine nitrogen using the procedures described herein to afford compounds of formula 6.

Additionally, instead of oxidizing the hydroxyl group of intermediate 3 to an aldehyde, this hydroxyl group can be converted into a leaving group, such as a chloro, bromo, iodo, mesylate or tosylate, using conventional reagents and reaction procedures. The resulting leaving group is then readily displaced with 4-amino-1-(pyridylmethyl)piperidine 5 to afford compound 6. Alternatively, this leaving group can also be displaced with intermediate 14 to provide compounds of formula 6 after deprotection and coupling to aldehyde 17 as described above.

Compounds of this invention can also be prepared by the procedure illustrated in Scheme D.

Scheme D

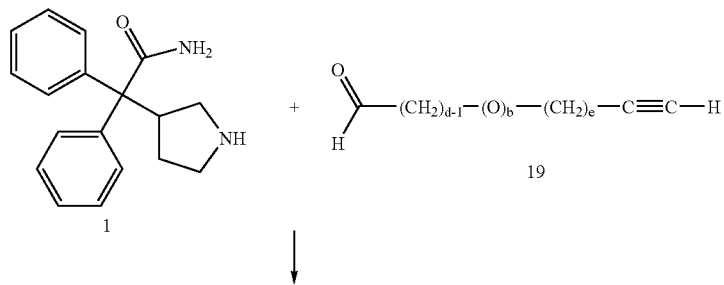

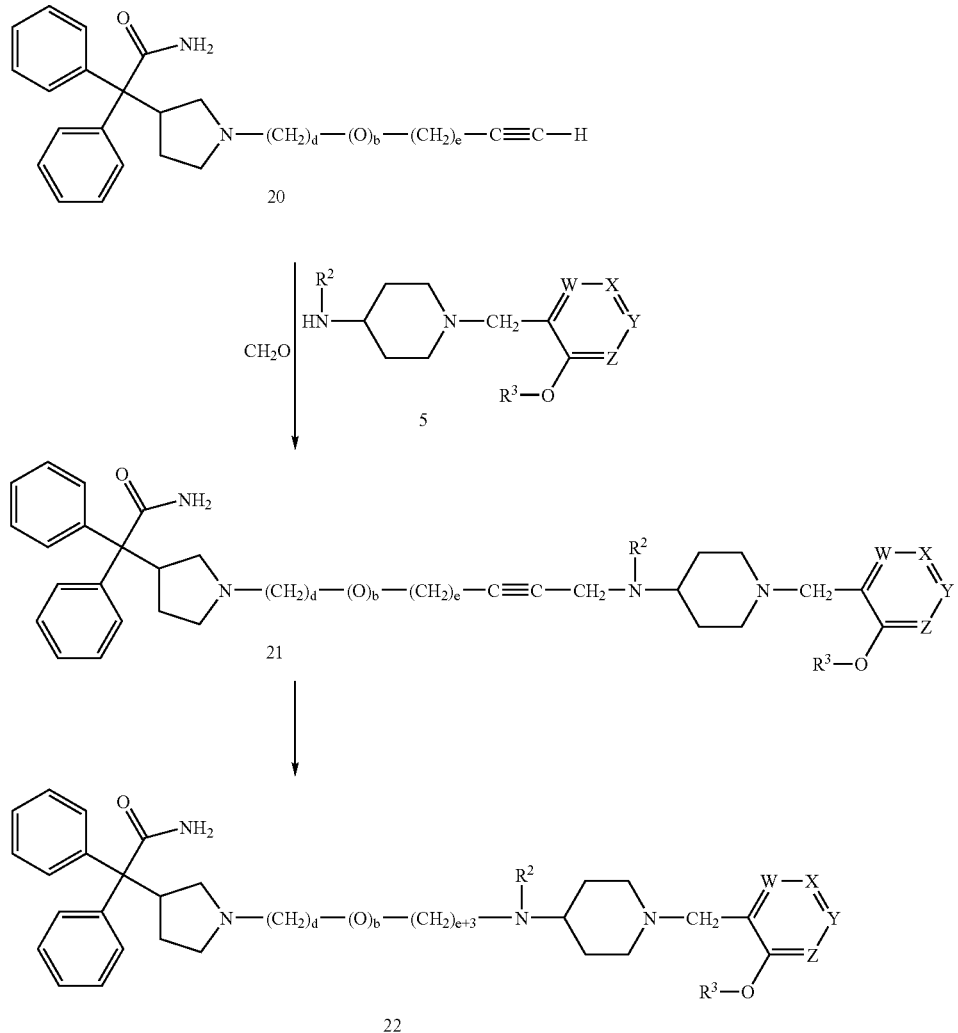

As shown in Scheme D, a compound of formula 1 is first coupled with an aldehyde of formula 19 to provide alkyne intermediate 20. This reaction is typically conducted by contacting 1 with about 1.1 to about 1.3 equivalents of 19 in the presence of a suitable reducing agent. Preferably, this reaction is conducted using about 1.0 to about 1.1 equivalents of sodium triacetoxyborohydride and about 1.0 equivalents of acetic acid. Typically, this reaction is conducted in an inert diluent, such as dichloromethane, at a temperature ranging from about 0° C. to about 50° C., preferably at ambient temperature, for about 0.25 to about 6 hours, or until the reaction is substantially complete.

The aldehydes of formula 19 employed in this reaction are either commercially available or can be prepared from commercially available starting materials using standard reagents and procedures. Representative aldehydes suitable for use in this reaction include, by way of example, 5-hexyn-1-al, 6-heptyn-1-al, 7-octyn-1-al, 4-oxa-7-octyn-1-al and the like.

The alkyne intermediate of formula 20 is then coupled to 4-amino-1-(pyridylmethyl)piperidine 5 using formaldehyde and a copper (I) catalyst to afford intermediate 24. Typically, the reaction is conducted by contacting 20 with about 1.05 to about 1.2 equivalents of 5 and about 1.2 to about 1.4 equivalents of paraformaldehyde in the presence of a catalytic amount, preferably about 0.2 equivalents, of a copper (I) salt, such as copper (I) chloride. Typically, the reaction is carried out in an inert diluent, such as tetrahydrofuran, at a temperature ranging from about 25° C. to about 75° C. for about 2 to about 24 hours, or until the reaction is substantially complete.

The resulting intermediate of formula 21 is then reduced to provide a compound of formula 22. Preferably, this reduction is conducted by contacting 21 with excess, preferably with about 10 equivalents, of p-toluenesulfonhydrazide, and an excess, preferably about 20 equivalents, of sodium acetate. Typically, this reaction is conducted by contacting of a solution of 21 and p-toluenesulfon-hydrazide in an inert diluent, such as 1,2-dimethoxyethane, with an aqueous solution of sodium acetate at a temperature ranging from about 50° C. to about 100° C. for about 12 to about 48 hours, or until the reaction is substantially complete. The resulting compound of formula 22 is typically purified using standard procedures, such as chromatography, recrystallization and the like.

Compounds of this invention can also be prepared by the procedure illustrated in Scheme E.

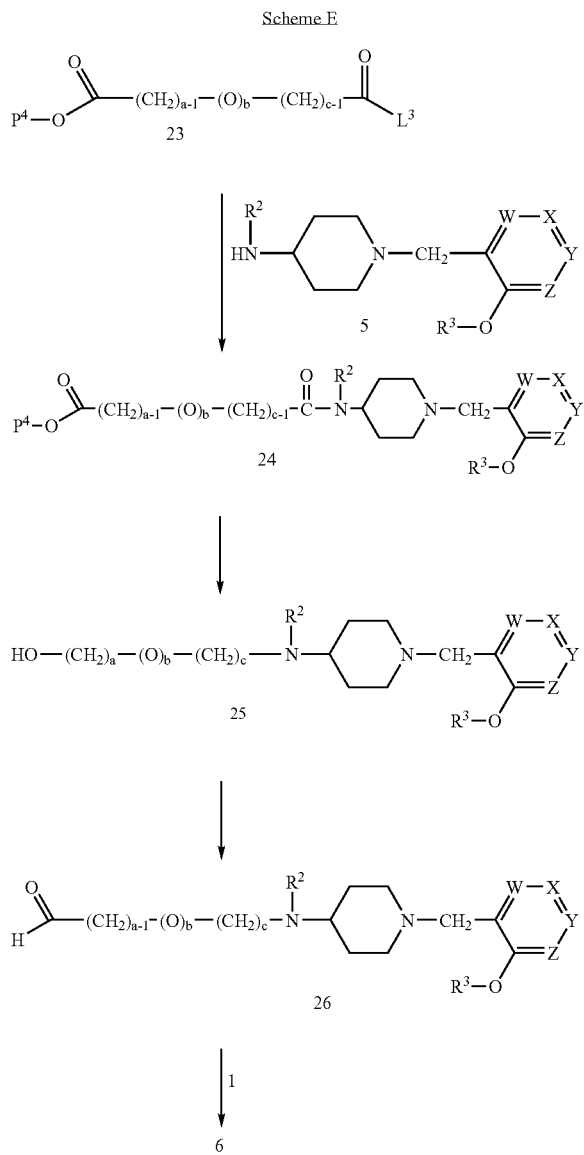

As shown in Scheme E, 4-amino-1-(pyridylmethyl)piperidine 5 can be reacted with compound 23, where $L^3$ is a leaving group, such as chloro or bromo, and $P^4$ is a carboxy-protecting group, such as a methyl or ethyl; to provide amide intermediate 24. This reaction is typically conducted by contacting 5 with about 1.0 to about 1.2 equivalents of compound 23 in the presence of excess, preferably about 1.2 to about 2.0 equivalents of a trialkylamine, such as N,N-diisopropylethylamine. This reaction is typically conducted in an inert diluent, such as dichloromethane, at a temperature ranging from about −10° C. to about 25° C. for about 1 to about 24 hours or until the reaction is substantially complete.

Amide 24 is then reduced with a metal hydride reducing agent, such as lithium aluminum hydride, to afford alcohol 25. This reaction is typically conducted by contacting 24 with excess metal hydride reducing agent, preferably with about 3 to about 5 equivalents of lithium aluminum hydride, in an inert diluent, such as tetrahydrofuran. This reduction is generally conducted at a temperature ranging from about −30° C. to about 10° C. for about 6 to about 24 hours, or until the reaction is substantially complete.

Using the procedures described herein above, alcohol 25 can then be oxidized to aldehyde 26, and 26 then coupled to intermediate 1 to afford compounds of formula 6. Alternatively, alcohol 25 can be converted into a leaving group, such as chloro, bromo, mesylate or tosylate, and then coupled to intermediate 1 using the procedures described herein above.

Finally, if desired, the pyridine N-oxide compounds of this invention can be prepared by oxidizing the corresponding pyridine compound with any suitable oxidizing agent. For example, pyridine N-oxides can be prepared using 30% hydrogen peroxide in acetic acid; 40% peracetic acid in acetic acid; and the like.

Further details regarding specific reaction conditions and other procedures for preparing representative compounds of this invention or intermediates thereto are described in the Examples set forth below.

Pharmaceutical Compositions

The substituted 4-amino-1-(pyridylmethyl)piperidine and related compounds of this invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, this invention is directed to a pharmaceutical composition comprising a pharmaceutically-acceptable carrier or excipient and a therapeutically effective amount of a compound of formula I or a pharmaceutically acceptable salt thereof. Optionally, such pharmaceutical compositions may contain other therapeutic and/or formulating agents if desired.

The pharmaceutical compositions of this invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of this invention. The choice of a particular carrier or excipient, or combinations of carriers or exipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of this invention are typically prepared by throughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of this invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of this invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In another preferred embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of this invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of this invention and a powder suitable for use in a powder inhaler. Suitable powder bases include, by way of example, lactose or starch.

The compounds of this invention can also be administered transdermally using known transdermal delivery systems and excipients. For example, a compound of this invention can be admixed with permeation enhancers, such as propylene glycol, polyethylene glycolm monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with a compound of formula I, or pharmaceutically-acceptable salt or solvate or stereoisomer thereof. For example, the pharmacuetical compositions of this invention may further comprise one or more therapeutic agents selected from the group consisting of $O_2$ adrenergic receptor agonists, anti-inflammatory agents (e.g. corticosteroids and non-steroidal anti-inflammatory agents (NSAIDs), other muscarinic receptor antagonistst (i.e., antichlolinergic agents), antiinfective agents (e.g. antibiotics or antivirals) and antihistamines. The other therapeutic agents can be used in the form of pharmaceutically acceptable salts or solvates. Additionally, if appropriate, the other therapeutic agents can be used as optically pure stereoisomers.

The following formulations illustrate representative pharmaceutical compositions of the present invention:

FORMULATION EXAMPLE A

Hard gelatin capsules for oral administration are prepared as follows:

| Ingredients | Amount |
| --- | --- |
| Compound of the invention | 250 mg |
| Lactose (spray-dried) | 200 mg |
| Magnesium stearate | 10 mg |

Representative Procedure: The ingredients are throughly blended and then loaded into a hard gelatine capsule (460 mg of composition per capsule).

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are throughly blended and then passed through a No. 45 mesh U.S. sieve and loaded into a hard gelatin capsule (200 mg of composition per capsule).

FORMULATION EXAMPLE C

Capsules for oral administration are prepared as follows:

| Ingredients | Amount |
| --- | --- |
| Compound of the invention | 100 mg |
| Polyoxyethylene sorbitan monooleate | 50 mg |
| Starch powder | 250 mg |

Representative Procedure: The ingredients are throughly blended and then loaded into a gelatin capsule (300 mg of composition per capsule).

FORMULATION EXAMPLE D

Tablets for oral administration are prepared as follows:

| Ingredients | Amount |
| --- | --- |
| Compound of the invention | 10 mg |
| Starch | 45 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed throughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

FORMULATION EXAMPLE E

Tablets for oral administration are prepared as follows:

| Ingredients | Amount |
| --- | --- |
| Compound of the invention | 250 mg |
| Microcrystalline cellulose | 400 mg |
| Silicon dioxide fumed | 10 mg |
| Stearic acid | 5 mg |

Representative Procedure: The ingredients are throughly blended and then compressed to form tablets (665 mg of composition per tablet).

FORMULATION EXAMPLE F

Single-scored tablets for oral administration are prepared as follows:

| Ingredients | Amount |
| --- | --- |
| Compound of the invention | 400 mg |
| Cornstarch | 50 mg |
| Croscarmellose sodium | 25 mg |
| Lactose | 120 mg |
| Magnesium stearate | 5 mg |

Representative Procedure: The ingredients are throughly blended and compressed to form a single-scored tablet (600 mg of compositions per tablet).

FORMULATION EXAMPLE G

A suspension for oral administration is prepared as follows:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 100 mg of active ingredient per 10 mL of suspension.

FORMULATION EXAMPLE H

A dry powder for administration by inhalation is prepared as follows:

| Ingredients | Amount |
| --- | --- |
| Compound of the invention | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

FORMULATION EXAMPLE I

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of active compound as micronized particles with mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into cartridges with pressurized 1,1,1,2-tetrafluoroethane.

FORMULATION EXAMPLE J

An injectable formulation is prepared as follows:

| Ingredients | Amount |
| --- | --- |
| Compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

FORMULATION EXAMPLE K

Capsules for oral administration are prepared as follows:

| Ingredients | Amount |
| --- | --- |
| Compound of the Invention (as naphthalene-1-5-disulfonic acid salt) | 40.05 mg |
| Microcrystalline cellulose (Avicel PH 103) | 259.2 mg |
| Magnesium stearate | 0.75 mg |

Representative Procedure: The ingredients are throughly blended and then loaded into a gelatin capsule (Size #1, White, Opaque) (300 mg of composition per capsule).

FORMULATION EXAMPLE L

Capsules for oral administration are prepared as follows:

| Ingredients | Amount |
| --- | --- |
| Compound of the Invention (as naphthalene-1,5-disulfonic acid salt) | 160.2 mg |
| Microcrystalline cellulose (Avicel PH 103) | 139.05 mg |
| Magnesium stearate | 0.75 mg |

Representative Procedure: The ingredients are throughly blended and then loaded into a gelatin capsule (Size #1, White, Opaque) (300 mg of composition per capsule).

Utility

The substituted 4-amino-1-(pyridylmethyl)piperidine and related compounds of this invention are useful as muscarinic receptor antagonists and therefore, such compounds are useful for treating medical conditions mediated by muscarinic receptors, i.e., medical conditions which are ameliorated by treatment with a muscarinic receptor antagonist. Such medical conditions include, by way of example, genitourinary tract disorders, such as overactive bladder or detrusor hyperactivity and their symptoms; gastrointestinal tract disorders, such as irritable bowel syndrome, diverticular disease, achalasia, gastrointestinal hypermotility disorders and diarrhea; respiratory tract disorders, such as chronic obstructive pulmonary disease, asthma and pulmonary fibrosis; cardiac arrhythmias, such as sinus bradycardia; Parkinson's disease; cognitive disorders, such as Alzheimer's disease; dismenorrhea; and the like.

In particular, the compounds of this invention are useful for treating smooth muscle disorders in mammals, including humans. Such smooth muscle disorders include, by way of illustration, overactive bladder, chronic obstructive pulmonary disease and irritable bowel syndrome.

When used to treat smooth muscle disorders or other conditions mediated by muscarinic receptors, the compounds of this invention will typically be administered orally, rectally, parenterally or by inhalation in a single daily dose or in multiple doses per day. The amount of active agent administered per dose or the total amount administered per day will typically be determined by the patient's physician and will depend on such factors as the nature and severity of the patients condition, the condition being treated, the age and general health of the patient, the tolerance of the patient to the active agent, the route of administration and the like.

Typically, suitable doses for treating smooth muscle disorders or other disorders mediated by muscarinic receptors will range from about 0.01 to about 50 mg/kg/day of active agent; preferably from about 0.02 to about 10 mg/kg/day. For an average 70 kg human, this would amount to about 0.7 to about 3500 mg per day of active agent.

In a preferred embodiment, the compounds of this invention are used to treat overactive bladder. When used to treat overactive bladder, the compounds of this invention will typically be administered orally in a single daily dose or in multiple doses per day; preferably in a single daily dose. Preferably, the dose for treating overactive bladder will range from about 1.0 to about 2000 mg/day.

In another preferred embodiment, the compounds of this invention are used to treat a respiratory disorder, such as chronic obstructive pulmonary disease or asthma. When used to treat chronic obstructive pulmonary disease or asthma, the compounds of this invention will typically be administered by inhalation in a single daily dose or in multiple doses per day. Preferably, the dose for treating chronic obstructive pulmonary disease or asthma will range from about 10 µg/day to about 10 mg/day.

In yet another preferred embodiment, the compounds of this invention are used to treat irritable bowel syndrome. When used to treat irritable bowel syndrome, the compounds of this invention will typically be administered orally or rectally in a single daily dose or in multiple doses per day. Preferably, the dose for treating irritable bowel syndrome will range from about 1.0 to about 2000 mg/day.

If desired, the compounds of this invention can be administered in combination with other therapeutic agents including one or more therapeutic agents selected from the group consisting of $\beta_2$ adrenergic receptor agonists (i.e., $\beta_2$ adrenoceptor agonists), anti-inflammatory agents (e.g. corticosteroids and non-steroidal anti-inflammatory agents (NSAIDs), $\beta_3$ adrenergic receptor agonists (i.e., $\beta_3$ adrenceptor agonists), other muscarinic receptor antagonistst (i.e., anticholinergic agents), antiinfective agents (e.g. antibiotics or antivirals), antihistamines and other therapeutic agents, such as cromylin sodium or theophylline.

Representative $\beta_2$ adrenergic receptor agonists that can be used in combination with the compounds of this invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically-acceptable salts thereof. Other $\beta_2$ adrenergic receptor agonists that can be used in combination with the compounds of this invention include, but are not limited to, 3-(4-{[6-({(2R)-2-hydroxy-2-[4-hydroxy-3-(hydroxymethyl)-phenyl]ethyl}amino) hexyl]oxy}butyl)benzenesulfonamide and 3-(-3-{[7-({(2R)-2-hydroxy-2-[4-hydroxy-3-(hydroxymethyl)phenyl] ethyl}amino)heptyl]oxy}-propyl)benzenesulfonamide and related compounds disclosed in WO 02/066422, published on Aug. 29, 2002; 3-[3-(4-{[6-([(2R)-2-hydroxy-2-[4-hydroxy-3-(hydroxymethyl)phenyl]ethyl}amino)hexyl] oxy}butyl)phenyl]imidazolidine-2,4-dione and related compounds disclosed in WO 02/070490, published Sep. 12, 2002; 3-(4-{[6-({(2R)-2-[3-(formylamino)-4-hydroxyphenyl]-2-hydroxyethyl}amino)hexyl]oxy}butyl)benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino) hexyl]oxy}butyl)benzenesulfonamide, N-(tert-butyl)-3-(4-{[6-({(2R)-2-[3-(formylamino)-4-hydroxyphenyl]-2-hydroxyethyl}amino)hexyl]-oxy}butyl) benzenesulfonamide, N-(tert-butyl)-3-(4-{[6-({(2S)-2-[3-(formylamino)-4-hydroxyphenyl]-2-hydroxyethyl}amino) hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl) benzenesulfonamide and related compounds disclosed in WO 02/076933, published on Oct. 3, 2002; 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439, published on Mar. 27, 2003; and pharmaceutically-acceptable salts thereof. When employed, the P$_2$-adrenoreceptor agonist will be present in the pharmaceutical composition in a therapeutically effective amount. Typically, the $\beta_2$-adrenergic receptor agonist will be present in an amount sufficient to provide from about 0.05 µg to about 500 µg per dose.

Representative corticosteroids that can be used in combination with the compounds of this invention include, but are not limited to, methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, ST-126 and the like, or pharmaceutically-accetable salts thereof. When employed, the cortecosteriod will be present in the pharmaceutical composition in a therapeutically effective amount. Typically, the steroidal anti-inflammatory agent will be present in an amount sufficient to provide from about 0.05 µg to about 500 µg per dose.

Other suitable combinations include, for example, other anti-inflammatory agents, e.g., NSAIDs (such as sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis.

For example, representative phosphodiesterase-4 (PDE4) inhibitors or mixed PDE3/PDE4 inhibitors that can be used in combination with the compounds of this invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3- cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically-acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Punafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative $\beta_3$ adrenergic receptor agonists that can be used in combination with the compounds of this invention include, but are not limited to, 2-[4-[2-[[(1S,2R)-2-hydroxy-2-[4-hydroxyphenyl)-1-methylethyl]amino]ethyl]phenoxy]acetic acid; 2-[2-chloro-4-[2-[[(1S,2R)-2-hydroxy-2-[4-hydroxyphenyl)-1-methylethyl]amino]ethyl]-phenoxy]acetic acid; and related compounds disclosed in U.S. Pat. No. 6,538,152 B1, issued on Mar. 25, 2003, and U.S. Pat. No. 6,376,707 B1, issued on Apr. 23, 2002. Other suitable $\beta_3$ adrenergic receptor agonists include those disclosed in U.S. Pat. No. 6,353,025 B1, issued on Mar. 5, 2002; and U.S. patent application Publication No. US 2003/0166719 A1, published on Sep. 4, 2003, and US 2003/0181726 A1, published on Sep. 25, 2003. When employed, the $\beta_3$ adrenergic receptor agonist will be present in the pharmaceutical composition in a therapeutically effective amount. Typically, the $\beta_3$ adrenergic receptor agonist will be present in an amount sufficient to provide from about 1 mg to about 1000 mg per day per adult human. The administration of a muscarinic receptor antagonist of the present invention in combination with a $\beta_3$ adrenergic receptor agonist is particularly useful for treating overactive bladder and other urinary disorders. Such compounds, when administered simultaneously or sequentially, will have synergistic effects for the treatment of smooth muscle disorders, such as overactive bladder.

Representative muscarinic antagonists (i.e., anticholinergic agents) that can be used in combination with, and in addition to, the compounds of this invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically-acceptable salt thereof; or, for those compounds listed as a salt, alternate pharmaceutically-acceptable salt thereof.

Representative antihistamines (i.e., $H_1$-receptor antagonists) that can be used in combination with the compounds of this invention include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically-acceptable salt thereof, or, for those compounds listed as a salt, alternate pharmaceutically-acceptable salt thereof.

Suitable doses for the other therapeutic agents administered in combination with a compound of the invention are in the range of about 0.05 µg/day to about 100 mg/day.

Since compounds of this invention are muscarinic receptor antagonists, such compounds are also useful as research tools for investigating or studying biological systems or samples having muscarinic receptors, or for discovering new muscarinic receptor antagonists. Such biological systems or samples may comprise $M_1$, $M_2$, $M_3$, $M_4$ and/or $M_5$ muscarinic receptors. Moreover, since compounds of this invention are selective $M_2$ muscarinic receptor subtype antagonists, such compounds are particularly useful for studying the effects of selective antagonism of $M_2$ receptors in a biological system or sample. Any suitable biological system or sample having muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

In this embodiment, a biological system or sample comprising a muscarinic receptor is contacted with a muscarinic receptor-antagonizing amount of a compound of this invention. The effects of antagonizing the muscarinic receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio) triphosphate ([$^{35}$S]GTPγS) into isolated membranes via receptor catalyzed exchange of [$^{35}$S]GTPγS for GDP, ligand-mediated changes in free intracellular calcium ions (measured, for example, with a fluorescence-linked imaging plate reader or FLIPR® from Molecular Devices, Inc.). A compound of this invention will antagonize or decrease the activation of muscarinic receptors in any of the functional assays listed above, or assays of a similar nature. A muscarinic receptor-antagonizing amount of a compound of this invention will typically range from about about 0.1 nanomolar to about 100 nanomolar.

Additionally, the compounds of this invention can be used as research tools for discovering new muscarinic receptor antagonists. In this embodiment, muscarinic receptor binding data (for example, as determined by an in vitro radioligand displacement assay) for a test compound or a group of test compounds is compared to the muscarinic binding data for a compound of this invention to identify test compounds that have about equal or superior muscarinic receptor binding, if any. This aspect of the invention includes, as separate embodiments, both the generation of comparison data (using the appropriate assay) and the analysis of the test data to identify test compounds of interest.

Among other properties, compounds of this invention have been found to be potent inhibitors of $M_2$ muscarinic receptor activity. Accordingly, in a preferred embodiment, this invention is directed to compounds of formula I having an inhibition dissociation constant for the $M_2$ receptor subtype of less than or equal to 100 nM; preferably, less than or equal to 50 nM; and more preferably, less than or equal to 10 nM (as determined by in vitro radioligand displacement assays).

Additionally, compounds of this invention have also been found to possess surprising and unexpected selectivity for the $M_2$ muscarinic receptor relative to the $M_3$ muscarinic receptor. Accordingly, in another preferred embodiment, this invention is directed to compounds of formula I having an $hM_3/hM_2$ ratio of at least 5; preferably at least 10; and more preferably at least 20 (as determined by in vitro radioligand displacement assays). In one embodiment, the $hM_3/hM_2$ ratio is in the range of from about 5 to about 200; preferably, from about 10 to about 100.

These properties, as well as the utility of the compounds of this invention, can be demonstrated using various in vitro and in vivo assays well-known to those skilled in the art. For example, representative assays are described in further detail in the following Examples.

EXAMPLES

The following synthetic and biological examples are offered to illustrate this invention and are not to be construed in any way as limiting the scope of this invention. In the examples below, the following abbreviations have the following meanings unless otherwise indicated. Abbreviations not defined below have their generally accepted meaning.

| | |
|---|---|
| AC = | adenylyl cyclase |
| ACN = | acetonitrile |
| BSA = | bovine serum albumin |
| BOC = | tert-butoxycarbonyl |
| cAMP = | cyclic adenosine monophosphate |
| CHO = | Chinese hampster ovary |
| cpm = | counts per minute |
| DCM = | dichloromethane |
| DIPEA = | diisopropylethylamine |
| DME = | ethylene glycol dimethyl ether |
| DMF = | N,N-dimethylformamide |
| DMSO = | dimethyl sulfoxide |
| dPBS = | Dulbecco's phosphate buffered saline, without $CaCl_2$ and $MgCl_2$ |
| EDC = | 1-(3-dimethylaminopropyl)-3-ethylcarbodimide hydrochloride |
| EDTA = | ethylenediaminetetraacetic acid |
| EtOAc = | ethyl acetate |
| FBS = | fetal bovine serum |
| GDP = | guanosine 5'-diphosphate |
| HEPES = | 4-(2-hydroxyethyl)-1-piperazine-ethanesulfonic acid |
| $hM_1$ = | human muscarinic receptor subtype 1 |
| $hM_2$ = | human muscarinic receptor subtype 2 |
| $hM_3$ = | human muscarinic receptor subtype 3 |
| $hM_4$ = | human muscarinic receptor subtype 4 |
| $hM_5$ = | human muscarinic receptor subtype 5 |
| HOAt = | 1-hydroxy-7-azabenzotriazole |
| HPLC = | high performance liquid chromatography |
| $K_i$ = | inhibition dissociation constant |
| MS = | mass spectrometry |
| [$^3$H]NMS = | l-[N-methyl-$^3$H]scopolamine methyl chloride |
| OIS = | oxotremorine-induced salivation |
| PMB = | p-methoxybenzyl |
| PyBOP = | benzotriazol-1-yloxytripyrrolidino-phosphonium hexafluorophosphate |
| TEA = | triethylamine |
| THF = | tetrahydrofuran |
| TLC = | thin layer chromatography |
| TFA = | trifluoroacetic acid |
| VIBC = | volume-induced bladder contraction |
| $VIBC_{Amp}$ = | volume-induced bladder contraction amplitude |

All temperatures reported in the following examples are in degrees Celsius (° C.) unless otherwise indicated. Also, unless noted otherwise, reagents, starting materials and solvents were purchased from commercial suppliers (such as Aldrich, Fluka, Sigma and the like) and were used without further purification.

HPLC was conducted using an Agilent 1100 HPLC or equivalent instrument under the following conditions as indicated:

HPLC Method A:

| | |
|---|---|
| Column: | Agilent Zorbax ® Bonus-RP 5μ 4.6 × 250 mm |
| Detector Wavelength: | 214 nm |
| Column Temperature: | 40° C. |
| Flow Rate: | 1.0 mL/min |
| Mobile Phases: | A = 2% acetonitrile, 98% water, 0.1% TFA |
| | B = 90% acetonitrile, 10% water, 0.1% TFA |
| Injection Volume: | 5 μL |
| Run Time: | 62 min |
| Gradient: | 2-40% B in A |

HPLC Method B:

| | |
|---|---|
| Column: | YMC ODSA 5μ C18 4.6 × 50 mm |
| Detector Wavelength: | 220 nm |
| Column Temperature: | 35° C. |
| Flow Rate: | 4.0 mL/min |
| Mobile Phases: | A = 10% methanol, 90% water, 0.1% TFA |
| | B = 90% methanol, 10% water, 0.1% TFA |
| Injection Volume: | 5 μL |
| Run Time: | 5 min |
| Gradient: | 0-100% B in A |

HPLC Method C:

| | |
|---|---|
| Column: | Inertsil ODS-2 C18 |
| Detector Wavelength: | 254 nm |
| Column Temperature: | 35° C. |
| Flow Rate: | 1.0 mL/min |
| Mobile Phases: | A = 5% methanol, 95% water, 0.1% TFA |
| | B = 95% methanol, 5% water, 0.1% TFA |
| Injection Volume: | 5 μL |
| Run Time: | 15 min |
| Gradient: | 0-100% B in A |

HPLC Method D:

| | |
|---|---|
| Column: | ACE 5 C18, 4.6 mm × 25 cm |
| Detector: | DAD1, Signal = 230 nm/10 nm, Ref = 360 nm |
| Column Temperature: | 45° C. |
| Flow Rate: | 1.5 mL/min |
| Mobile Phases: | A = 20 mM TEA (pH 5.65)/acetonitrile (98:2; v/v) B = 100 mM TEA (pH 5.5)/acetonitrile (20:80; v/v) |
| Injection Volume: | 20 μL |
| Run Time: | 38 min |
| Gradient: | 10-80% B in A |

Example A

Preparation of (S)-3-(1-Carbamoyl-1,1-diphenylmethyl)pyrrolidine

Step A—Preparation of (S)-Benzyl-3-(p-toluenesulfonyloxy)pyrrolidine

To a stirred solution of (S)-1-benzyl-3-pyrrolidinol (44.3 g, 0.25 mol) and 1,4-diazabicyclo[2.2.2]octane (33.7 g, 0.3 mol) in 250 mL of tert-butyl methyl ether under an atmosphere of nitrogen at 0° C., was added p-toluenesulfonyl chloride (52.4 g, 0.275 mol) portion-wise over 20 min. The reaction mixture was stirred at 0° C. for 1 h. The ice bath was removed and the mixture was stirred at ambient temperature overnight (20±5 h). Ethyl acetate (100 mL) was added, followed by saturated aqueous sodium bicarbonate solution (250 mL). The resulting mixture was stirred at ambient temperature for 1 h. The layers were separated and the organic layer was washed with saturated aqueous sodium bicarbonate solution (250 mL); saturated aqueous ammonium chloride solution (250 mL); saturated aqueous sodium chloride solution (250 mL); and then dried over sodium sulfate (80 g). The sodium sulfate was filtered off and washed with ethyl acetate (20 mL) and the solvent was removed in vacuo to give 78.2 g of the title intermediate as an off-white solid (94% yield; 95% purity by HPLC Method B).

Step B—Preparation of (S)-1-Benzyl-3-(1-cyano-1,1-diphenylmethyl)-pyrrolidine

To a stirred solution of diphenylacetonitrile (12.18 g, 61.8 mmol) in anhydrous THF (120 mL) at 0° C., potassium tert-butoxide (10.60 g, 94.6 mmol) was added over 5 min. The reaction mixture was stirred at 0° C. for 1 h. To the reaction mixture at 0° C. was added (S)-1-benzyl-3-(p-toluenesulfonyloxy)-pyrrolidine (20.48 g, 61.3 mmol) in one portion. The cold bath was removed and the reaction mixture was stirred for 5-10 min at which time the reaction mixture had become a brown homogeneous solution. The reaction mixture was then heated at 40° C. overnight (20±5 h). The reaction mixture (bright yellow suspension) was allowed to cool to room temperature before adding water (150 mL). Most of the THF was then removed in vacuo and isopropyl acetate (200 mL) was added. The layers were separated and the organic layer was washed with saturated aqueous ammonium chloride solution (150 mL); saturated aqueous sodium chloride solution (150 mL); and then dried over sodium sulfate (50 g). The sodium sulfate was filtered off and washed with isopropyl acetate (20 mL) and the solvent was removed in vacuo to give 23.88 g of the title intermediate as a light brown oil (>99% yield, 75% purity by HPLC Method B, contaminated mainly with excess diphenylacetonitrile).

Step C—Preparation of (S)-3-(1-Cyano-1,1-diphenylmethyl)pyrrolidine (S)-1-Benzyl-3-(1-cyano-1,1-diphenylmethyl)pyrrolidine was dissolved in isopropyl acetate (ca. 1 g/10 mL) and the solution was mixed with an equal volume of 1N aqueous hydrochloric acid. The resulting layers were separated and the aqueous layer was extracted with an equal volume of isopropyl acetate. The organic layers were combined, dried over sodium sulfate and filtered. The solvent was removed in vacuo to afford (S)-1-benzyl-3-(1-cyano-1,1-diphenylmethyl)pyrrolidine hydrochloride as a light yellow foamy solid. (Note: This hydrochloride salt can also be prepared during the work-up of Step B).

To a stirred solution of (S)-1-benzyl-3-(1-cyano-1,1-diphenylmethyl)pyrrolidine hydrochloride (8.55 g, 21.98 mmol) in methanol (44 mL) was added palladium on carbon (1.71 g) and ammonium formate (6.93 g, 109.9 mmol). The reaction mixture was heated to 50° C. with stirring for 3 h. The reaction was cooled to ambient temperature and water (20 mL) was added. The resulting mixture was filtered through a pad of Celite, washing with methanol (20 mL). The filtrate was collected and most of the methanol was removed in vacuo. The residue was mixed with isopropyl acetate (100 mL) and 10% aqueous sodium carbonate (50 mL). The resulting layers were separated and the aqueous layer was extracted with isopropyl acetate (50 mL). The organic layers were combined and dried over sodium sulfate (20 g). The sodium sulfate was filtered off and washed with isopropyl acetate (20 µL). The solvent was removed in vacuo to afford 5.75 g of the title intermediate as a light yellow oil (99.7% yield, 71% purity by HPLC).

Step D—Preparation of (S)-3-(1-Carbamoyl-1,1-diphenylmethyl)-pyrrolidine

A 200 mL flask with a magnetic stir bar and a nitrogen inlet was charged with (S)-3-(1-cyano-1,1-diphenylmethyl)pyrrolidine (2.51 g) and 80% $H_2SO_4$ (19.2 mL; pre-prepared with 16 mL of 96% $H_2SO_4$ and 3.2 mL of $H_2O$). The reaction mixture was then heated at 90° C. for 24 h or until starting material was consumed as indicated by HPLC. The reaction mixture was allowed to cool to room temperature and then poured onto ice (ca. 50 mL by volume). A 50% aqueous sodium hydroxide solution was added slowly to the mixture with stirring over an ice bath until the pH was about 12. Dichloromethane (200 mL) was added and mixed with the aqueous solution at which time sodium sulfate precipitated out and was filtered off. The filtrate was collected and the layers were separated. The aqueous layer was extracted with dichloromethane (100 mL) and the organic layers were combined and dried with over sodium sulfate (5 g). The sodium sulfate was filtered off and washed with dichloromethane (10 mL). The solvent was removed in vacuo to give the crude product as a light yellow foamy solid (ca. 2.2 g, 86% purity by HPLC).

The crude product was dissolved in ethanol (18 mL) with stirring. To this solution was added a warm solution of L-tartaric acid (1.8 g) in ethanol (14 mL) and the resulting mixture was stirred overnight (15±5 h). The resulting precipitate was isolated by filtration to give an off-white solid (ca. 3.2 g, >95% purity by HPLC). Methanol (15 mL) was added to this solid and the resulting slurry was stirred at 70° C. overnight (15 h). The slurry was allowed to cool to ambient temperature and a white solid (~2.6 g, >99% purity by HPLC) was obtained after filtration. To this solid was added ethyl acetate (30 mL) and 1 N aqueous sodium hydroxide (25 mL). This mixture was mixed until two distinct layers formed and then the layers were separated and the aqueous layer was extracted with ethyl acetate (20 mL). The organic layers were combined and dried over sodium sulfate (10 g). The sodium sulfate was removed by filtration and the solvent was evaporated in vacuo to afford 1.55 g of the title intermediate as an off-white foamy solid (58% yield; >99% purity by HPLC Method C).

Example B

Preparation of (S)-3-(1-Carbamoyl-1,1-diphenylmethyl)-1-(7-hydroxyhept-1-yl)pyrrolidine To a stirred solution of (S)-3-(1-carbamoyl-1,1-diphenylmethyl)pyrrolidine (40 g, 142.7 mmol) and triethylamine (59.6 mL, 428 mmol) in acetonitrile (1.1 L) at 40° C. under a nitrogen atmosphere was added 7-bromo-1-heptanol (24 mL, 146 mmol) in acetonitrile (100 mL) dropwise. The reaction mixture was heated to 50° C. for 9 hours. The reaction mixture was allowed to cool before removing the solvent under reduced pressure. The crude residue was dissolved in dichloromethane (500 mL) and the organic layer washed with saturated aqueous sodium bicarbonate (2×300 mL), followed by water (300 mL) and saturated aqueous sodium chloride (300 mL), and then dried over magnesium sulfate (10 g). The magnesium sulfate was filtered off and washed with dichloromethane (100 mL). The solvent was then removed in vacuo to give the crude product which was purified on a short column ($SiO_2$) by varying the eluant from 19:1:0.1 to 3:1:0.1 $CH_2Cl_2$/MeOH/$NH_4OH$ to give 31.35 g of the title intermediate as a white solid (56% yield; >95% purity by HPLC Method A).

Example C

Preparation of (S)-3-(1-Carbamoyl-1,1-diphenylmethyl)-1-(7-oxohept-1-yl)pyrrolidine To a stirred solution of (S)-3-(1-carbamoyl-1,1-diphenylmethyl)-1-(7-hydroxyhept-1-yl)pyrrolidine (31.00 g, 78.57 mmol); N,N-diisopropylethylamine (68.4 mL, 392.8 mmol); and methyl sulfoxide (60.7 mL, 785.7 mmol) in dichloromethane (780 mL) under an atmosphere of nitrogen at −15° C., was added sulfur trioxide pyridine complex (37.5 g, 235.71 mmol) portion-wise over a 40 min. period. The reaction mixture was maintained between −10° C. and −20° C. during the addition. The reaction was then stirred in this temperature range for 40±10 min. Deionized water (300 mL) was added and the mixture was stirred for 10 minutes. The organic layer was separated and washed with deionized water (200 mL), followed by saturated aqueous sodium chloride (200 mL) and the organic layer was then dried with magnesium sulfate (10 g). The magnesium sulfate was filtered off and washed with dichloromethane (50 mL) and the solvent was reduced in vacuo. The resultant syrup was washed with petroleum ether (2×200 mL) to remove the remaining pyridine and DMSO and the resulting white solid was dried in vacuo to give 33.02 g of the title intermediate (98% yield; >93% purity by chiral HPLC Method A).

Example D

Preparation of (S)-3-(1-Carbamoyl-1,1-diphenylmethyl)-1-(hex-5-yn-1-yl)pyrrolidine Step A—Preparation of Hex-5-yn-1-al To a stirred solution of 5-hexyn-1-ol (10.0 g, 0.10 mol) stirring in dichloromethane (1 L) under an atmosphere of nitrogen, was added DMSO (71 mL, 1.0 mol) followed by DIPEA (174 mL, 1.0 mol). The reaction mixture was cooled to −15° C. and sulfur trioxide pyridine complex (79.6 g, 0.5 mol) was added in 10 g portions over 60 mins. The reaction mixture was stirred at −15° C. for 1 hour before examining by TLC (30% EtOAc/Hexane) to observe for complete consumption of the starting material. To the reaction mixture was added 1 N aqueous hydrochloric acid (1 L), and the organic layer was separated and washed with 1 N aqueous hydrochloric acid (3×500 mL), saturated aqueous sodium bicarbonate (500 mL), brine (1 L), dried over magnesium sulfate and the solvent reduced in vacuo to afford the title intermediate (NOTE: Product is volatile, use cold water bath and remove when solvent evaporated).

Step B—Preparation of (S)-3-(1-Carbamoyl-1,1-diphenylmethyl)-1-(hex-5-yn-1-yl)pyrrolidine To a stirred solution of (S)-3-(1-carbamoyl-1,1-diphenylmethyl)pyrrolidine (64.4 g, 0.23 mol); sodium triacetoxyborohydride (50.9 g, 0.24 mol) and acetic acid (13 mL, 0.23 mol) in dichloromethane (511 mL) at room temperature, was added a solution of hex-5-yn-1-al (26.14 g, 0.27 mol) in dichloromethane (256 mL). The reaction mixture stirred at room temperature overnight (ca. 8 hours) and then the reaction mixture was quenched by addition of concentrated hydrochloric acid (30 mL) and stirring was continued for 1 hour at room temperature. The mixture was then diluted with water (750 mL) and made basic to pH 5 using 10 N sodium hydroxide (18 mL). The layers were separated and the organic layer was washed with 1 N sodium hydroxide (200 mL). The organic layer was dried over magnesium sulfate (10 g); filtered and then concentrated in vacuo to afford 67.6 g of the title intermediate as a yellow gummy solid (83% yield).

Example E

Preparation of 4-Methoxypyridine-3-carboxaldehyde

Tert-butyllithium (90.6 mL, 154 mmol; 1.7 M in pentane) was added via cannula to a stirred solution of tetrahydrofuran (380 mL) under an atmosphere of nitrogen at room temperature. The reaction mixture was cooled to −78° C. before adding 2-bromomesitylene (11.3 mL, 74.1 mmol) dropwise. The reaction mixture was allowed to stir for 1 hour at −78° C. To the reaction mixture at −78° C. was added 4-methoxypyridine (5.79 mL, 57 mmol) dropwise, and the resulting mixture was stirred at −23° C. for 3 hours. The reaction mixture was then re-cooled to −78° C. and dimethylformamide (6.62 mL, 85.5 mmol) was added and stirring was continued for 1 hour at −78° C. The reaction mixture was quenched slowly at −78° C. with saturated aqueous sodium chloride solution (100 mL) and allowed to warm to room temperature slowly. To the reaction mixture was added diethyl ether (200 mL) and the layers were separated. The aqueous layer was extracted with diethyl ether (2×150 mL) and the combined organic layers were dried over potassium carbonate (20 g). The potassium carbonate was removed by filtration and washed with diethyl ether (100 mL) and the solvent removed under reduced pressure. The resulting crude 4-methoxy-3-pyridinecarboxaldehyde was purified by column chromatography (SiO$_2$, 5:95 ethanol:ethyl acetate) to give 4.79 g of the title intermediate as a yellow solid (61% yield; >98% purity by $^1$H NMR).

Analytical Data: $^1$H NMR (300 MHz, CDCl$_3$) δ 10.43 (s, 1H, CHO), 8.87 (s, 1H, ArH), 8.63 (d, 1H, J=6, ArH), 6.92 (d, 1H, J=6, ArH), 3.98 (s, 3H, CH$_3$O).

Example F

Preparation of 2-Methoxypyridine-3-carboxaldehyde

Using the procedure of Example E and substituting 2-methoxypyridine for 4-methoxypyridine, the title intermediate was prepared.

Example G

Preparation of 3-Methoxypyridine-2-carboxaldehyde

Using the procedure of Example E and substituting 3-methoxypyridine for 4-methoxypyridine, the title intermediate was prepared.

Example H

Preparation of 4-Isopropylamino-1-(4-methoxypyrid-3-ylmethyl)piperidine Monobenzoic Acid Salt Step A—Preparation of 1-Benzyl-4-isopropylaminopiperidine A solution of 4-amino-1-benzylpiperidine (45.8 g, 0.24 mol) and acetone (531 mL) was stirred at room temperature for 12 hours. The reaction mixture was then reduced to ca. 150 mL in vacuo. To this mixture was added methanol (100 mL) and the resulting mixture was cooled to 5° C. in an ice/water bath. Sodium triacetoxyborohydride (61.2 g, 0.29 mol) in methanol (350 mL), previously cooled to 5° C. in an ice/water bath, was added and this reaction mixture was stirred at 5° C. for 0.5 hours. The ice/water bath was removed and the reaction mixture was stirred for 2 hours at room temperature and then re-cooled to 5° C. in ice/water bath. To this mixture was added concentrated hydrochloric acid (75 mL) until the pH of the reaction mixture was about 3. This mixture was stirred for 1 hour and then concentrated in vacuo to about 600 mL and 1 N aqueous hydrochloric acid (200 mL) was added to dissolve the solids. The aqueous layer was washed with isopropyl acetate (400 mL) and the layers were separated. The aqueous layer was adjusted to pH 12 with 10 N aqueous sodium hydroxide (200 mL) and isopropylacetate (600 mL) was added. This mixture was stirred for 1 hour at room temperature and then the layers were separated and the organic layer washed with saturated aqueous sodium chloride solution (600 mL) and dried over sodium sulfate (80 g). The sodium sulfate was filtered off and washed with ethyl acetate (20 mL). The solvent was removed in vacuo to give 52.0 g of the title intermediate as a yellow oil (95% yield).

Step B—Preparation of 1-Benzyl-4-(N-tert-butoxycarbonyl-N-isopropylamino)piperidine A solution of 1-benzyl-4-isopropylaminopiperidine (69.7 g, 0.30 mol) in dichloromethane (200 mL) was cooled to 5° C. in an ice/water bath. To this solution was added di-tert-butyl dicarbonate (72.0 g, 0.33 mol) in dichloromethane (180 mL). The temperature did not rise more than 5° C. during the addition. The reaction mixture was stirred at 5° C. for 0.5 hour and then the ice/water bath was removed. The reaction mixture was stirred for 24 hours and was then concentrated in vacuo. The resulting yellow oil was placed under vacuum for 2 hours at which time it slowly crystallized to afford 98 g of the title intermediate as light yellow needle-shaped crystals (>99% yield).

Step C—Preparation of 4-(N-tert-Butoxycarbonyl-N-isopropylamino)piperidine

A solution of 1-benzyl-4-(N-tert-butoxycarbonyl-N-isopropylamino)piperidine (79.0 g, 0.24 mol) in ethanol (140 mL) was flushed with nitrogen for 15 minutes. This solution was then added to a 2 L Parr flask containing a mixture of 10% palladium on carbon (15.8 g; ca. 50% wt. water) in ethanol (100 mL), which solution had been flushed with nitrogen for 15 minutes. This reaction mixture was placed on a Parr Shaker under hydrogen at 50 psi for 24 hours. The reaction mixture was filtered through a pad of Celite and the Celite washed with ethanol. The filtrate was then concentrated in vacuo to afford 57.0 g of the title intermediate as a white solid (>99% yield).

Step D—Preparation of 4-(N-tert-Butoxycarbonyl-N-isopropylamino)-1-(4-methoxypyrid-3-ylmethyl)piperidine A solution of 4-(N-tert-butoxycarbonyl-N-isopropylamino)piperidine (118 g, 0.49 mol) in dichloroethane (600 mL) was stirred at room temperature for 1 hour, and then 4-methoxypyridine-3-carboxylate (63.5 g, 0.46 mol) was added. The resulting solution was stirred at room temperature for 2.5 hours and then cooled to 5° C. in an ice/water bath. Sodium triacetoxyborohydride (124 g, 0.58 mol) in dichloroethane (600 mL) was added and the reaction mixture was stirred at 5° C. for 15 minutes. The ice bath was then removed and reaction mixture was stirred for 4 hours at room temperature. Acetic acid (30 mL) was then added to the reaction mixture and the resulting mixture was stirred for 0.5 hours, and then concentrated to half its original volume. This solution was cooled in a dry ice/acetone bath and 10 N aqueous sodium hydroxide (350 mL) was added. This mixture was stirred for 0.5 hours and then the organic layer was separated and washed with 1 N aqueous sodium hydroxide (400 mL). The aqueous layer was then washed three times with dichloromethane (400 mL) and the combined organic layers were dried over sodium sulfate (40 g). The sodium sulfate was filtered off and washed with dichloromethane (100 mL) and the combined organic layers were concentrated in vacuo to give 177 g of the title intermediate as a yellow oil (>99% yield; 74% purity by GC).

Step E—Preparation of 4-Isopropylamino-1-(4-methoxypyrid-3-ylmethyl)piperidine

A solution of 4-(N-tert-butoxycarbonyl-N-isopropylamino)-1-(4-methoxypyrid-3-ylmethyl)piperidine (17.0 g, 0.047 mol) in dioxane (93 mL) was cooled to 5° C. in ice/water bath. To this solution was added concentrated hydrochloric acid (40 mL) and the resulting mixture was stirred 5° C. for 15 minutes. The ice/water bath was then removed and the reaction mixture was stirred for 12 hours. The reaction mixture was then concentrated in vacuo to dryness, diluted with dichloromethane (100 mL) and 10 N aqueous sodium hydroxide was added slowly (CAUTION: very exothermic) until the pH was 14. The mixture was stirred for 0.5 hours and the organic layer was then separated and the aqueous layer was washed three times with dichloromethane (200 mL). The organic layers were then separated and dried over sodium sulfate (10 g). The sodium sulfate was removed by filtration and the organic layer was concentrated in vacuo to give 7.8 g of the title intermediate as a yellow oil (65% yield; 83% purity by GC).

Step F—Preparation of 4-Isopropylamino-1-(4-methoxypyrid-3-ylmethyl)piperidine Monobenzoic Acid Salt To a 1L reaction flask equipped with a mechanical stirrer and a nitrogen inlet was added 4-isopropylamino-1-(4-methoxypyrid-3-ylmethyl)piperidine (45.7 g, 0.174 mol) and 200 mL of MTBE. The resulting mixture was heated to 50-55° C. to dissolve the solid. To this solution was added a solution of benzoic acid (21.3 g, 0.174 mol) in 100 mL of MTBE at 50-55° C. (Note: Heat may be needed to dissolve the benzoic acid in MTBE). This mixture was stirred at 50-55° C. for 30 minutes and then stirred at room temperature for 16 hours. The resulting solid was filtered and washed with 50 mL of MTBE and then dried under vacuum at 40° C. for 16 hours to give 54.9 g of the title intermediate as a white solid (82% yield; ≧99% purity).

Preparation of 4-Isopropylamino-1-(4-alkoxypyrid-3-ylmethyl)piperidines

If desired, the methyl group of the 4-methoxy substituent of 4-isopropylamino-1-(4-methoxypyrid-3-ylmethyl)piperidine can be exchanged for other alkyl groups using the following general procedure:

To a 1 M solution of 4-isopropylamino-1-(4-methoxypyrid-3-ylmethyl)piperidine in DMF was added sodium ethoxide (2 eq.), followed by anhydrous $Na_2SO_4$ (10 eq). The resulting mixture was heated at 80° C. with agitation for 15-20 h. The reaction mixture was then cooled to 0° C. under nitrogen and an alkyl halide (5-10 eq.) was added dropwise. The resulting mixture was stirred at 0° C. for 15 min and then stirred at room temperature for 30 to 60 min. The reaction was then quenched with water (10 times the volume of the reaction mixture). The aqueous layer was extracted with isopropyl acetate (equal volume to water). The layers were separated and the organic layer was dried over sodium sulfate, filtered and the solvent removed in vacuo to afford the desired product, typically as an oil.

For example, using this procedure, the following intermediates were prepared:

(a) Isopropyl-[1-(4-isopropoxypyridin-3-ylmethyl)piperidin-4-yl]amine: $^1$H NMR ($CDCl_3$, 300 MHz) δ: 8.39 (s, 1H), 8.31 (d, J=5.7 Hz, 1H), 6.70 (d, J=5.7 Hz, 1H), 4.60 (hept, J=6.0 Hz, 1H), 3.50 (s, 2H), 2.94 (hept, J=6.3 Hz, 1H), 2.84 (br d, J=12.4 Hz, 2H), 2.47 (ddd, J=4.2, 4.2, 10.8 Hz, 1H), 2.05 (ddd, J=2.4, 11.7, 11.7 Hz, 2H), 1.82 (br d, J=12.4 Hz, 2H), 1.33 (d, J=6.0 Hz, 6H), 1.1-1.2 (m, 2H), 1.00 (d, J=6.3 Hz, 6H) ppm; MS m/z 292.2 (expected 291.43 for $C_{17}H_{29}N_3O$);

(b) Isopropyl-[1-(4-n-propoxypyridin-3-ylmethyl)piperidin-4-yl]amine: MS m/z 292.2 (expected 291.43 for $C_{17}H_{29}N_3O$);

(c) Isopropyl-[1-{4-(2-fluoroethoxy)pyridin-3-ylmethyl}piperidin-4-yl]amine: MS m/z 296.3 (expected 295.40 for $C_{16}H_{26}FN_3O$); and (d) Isopropyl-[1-{4-(1-bromo-1,1-difluoromethoxy)pyridin-3-ylmethyl}piperidin-4-yl]amine: MS m/z 292.2 (expected 378.26 for $C_{15}H_{22}BrF_2N_3O$).

Additionally, the bromo substituent in intermediate (d) above can be exchanged for a fluoro substituent to afford isopropyl-[1-{4-(trifluoromethoxy)pyridin-3-ylmethyl}piperidin-4-yl]amine using the following procedure:

To a solution of isopropyl-[1-{4-(1-bromo-1,1-difluoromethoxy)pyridin-3-ylmethyl}piperidin-4-yl]amine (215 mg, 0.57 mmol) in hydrogen fluoride-pyridine (1 mL) at room temperature was added mercury(II) oxide (red, 147.9 mg, 0.68 mmol). After stirring at room temperature for 17 h, the volatile components were removed in vacuo. The residue was diluted with methanol (5 mL) and filtered. To the filtrate was added $NaBH(OAc)_3$ and the resulting black precipitate was removed by filtration. The step was repeated using additional $NaBH(OAc)_3$ until no black precipitate was observed. The solvent was then removed in vacuo and the resulting residue was purified by silica gel chromatography ($CH_2Cl_2/CH_3OH$/aqueous $NH_4OH$=1/0.1/0.05) to afford 12.3 mg of the title compound as a yellow oil ($R_f$=0.2).

Analytical Data: $^1$H NMR ($CDCl_3$, 300 MHz) δ: 7.78 (d, J=2.7 Hz, 1H), 7.54 (dd, J=2.7, 7.8 Hz, 1H), 6.47 (br s, 1H), 6.38 (d, J=7.8 Hz, 1H), 3.40 (s, 2H), 3.20 (hept, J=6.3 Hz, 1H), 2.81-2.96 (m, 3H), 2.14 (br dd, J=12.0 Hz, 2H), 1.89-1.98 (m, 2H), 1.69 (dddd, J=3.3, 12.0, 12.0, 12.0 Hz, 2H), 1.23 (d, J=6.3 Hz, 6H) ppm; MS m/z 318.3 (expected 317.35 for $C_{15}H_{22}F_3N_3O$).

Example I

Preparation of 4-{N-[7-(3-(S)-1-Carbamoyl-1,1-diphenylmethyl)pyrrolidin-1-yl)-4-oxahept-1-yl]-N-(isopropyl)amino}piperidine Step A—Preparation of 3-(3-Bromopropoxy)propionic Acid To a flask was added 3-bromopropanol (25 mL, 0.28 mol) and β-propiolactone (5.0 mL, 0.07 mol) and the resulting mixture was heated to 80° C. for 14 h. The reaction mixture was then cooled to room temperature and the excess 3-bromopropanol was removed under reduced pressure. The crude product was dissolved in dichloromethane (300 mL) and extracted with 1 N sodium hydroxide (300 mL). The aqueous layer was then acidified to pH 2 and extracted with dichloromethane (300 mL). The organic layer was then washed with water (200 mL), brine (200 mL), dried over anhydrous magnesium sulfate and the solvent removed under reduced pressure to give 9.4 g of the title intermediate, which was used without further purification (64% yield).

Analytical Data: $^1$H NMR ($CDCl_3$): δ 3.65 (t, 2H), 3.52 (t, 2H), 3.41 (t, 2H), 2.55 (t, 2H), 2.11 (t, 2H).

Step B—Preparation of 3-(3-Bromopropoxy)propionyl Chloride

To a stirred solution of 3-(3-bromopropoxy)propionic acid (15.2 g, 72.2 mmol) in $CCl_4$ (250 mL) was added $SOCl_2$ (5.5 mL, 76.0 mmol) and DMF (20 drops) and the reaction mixture was allowed to stir at room temperature for 18 h. The reaction mixture was concentrated under reduced pressure to give the title intermediate, which was used without further purification.

Step C—Preparation of N-(1-Benzylpiperdin-4-yl)-N-isopropyl 3-(bromopropoxy)propionamide The crude 3-(3-bromopropoxy)propionyl chloride from Step B was dissolved in dichloromethane (250 mL) and added dropwise to a solution of 1-benzyl-4-(isopropylamino)piperidine (16.7 g, 72 mmol) and diisopropylamine (11.8 mL, 86.0 mmol) in dichloromethane (300 mL) at 0° C. The mixture was stirred at 0° C. for 15 mins and then at room temperature for 2 hrs. The reaction mixture was then washed with saturated sodium bicarbonate, brine, dried over magnesium sulfate, and concentrated in vacuo to give 29.0 g of the title intermediate (95% yield for Steps B and C).

Analytical Data: MS m/z 425.3 ($MH^+$).

Step D—Preparation of 4-[N-(7-Bromo-4-oxahept-1-yl)-N-(isopropyl)amino]-1-benzylpiperidine To a stirred solution of N-(1-benzylpiperdin-4-yl)-N-isopropyl 3-(bromopropoxy)propionamide (28.2 g, 66 mmol) in THF (300 mL) was added $BH_3$-THF (100 mL, 2.0 M in THF, 200 mmol) and the reaction mixture was refluxed for 48 h. The reaction mixture was then allowed to cool to room temperature and methanol was added dropwise until evolution of hydrogen gas stopped. The mixture mixture was then concentrated under reduced pressure and dissolved in dichloromethane (500 mL). The reaction mixture was washed with 1 N hydrochlorid acid (500 mL) and the organic layer removed. The aqueous layer was then made basic to pH 12 using 1 N sodium hydroxide and extracted with dichloromethane (500 mL). The combined organic layers were washed with water (400 mL), brine (400 mL), dried over anhydrous magnesium sulfate and the solvent removed under reduced pressure. The resulting crude product was purified by silica gel chromatography (dichloromethane/methanol/aqueous ammonia: 9/0.5/0.05) to afford 20.5 g of the title intermediate (76% yield).

Analytical Data: MS m/z 411.4 (MH$^+$).

Step E—Preparation of 4-{N-[7-(3-(S)-1-Carbamoyl-1,1-diphenylmethyl)pyrrolidin-1-yl)-4-oxahept-1-yl]-N-(isopropyl)amino}-1-benzylpiperidine 4-[N-(7-Bromo-4-oxahept-1-yl)-N-(isopropyl)amino]-1-benzylpiperidine (6.0 g, 15 mmol) was dissolved in DMF (100 mL) and 4-methyl-2-pentanone (300 mL). To this mixture was added sodium carbonate (3.2 g, 30 mmol), 3-(S)-1-carbamoyl-1,1-diphenylmethyl)pyrrolidine (4.91 g, 18 mmol) and potassium iodide (250 mg, 1.5 mmol) and the resulting mixture was heated to 110° C. for 21 h. Upon completion, the reaction was brought to room temperature, concentrated under reduced pressure and the crude product purified by silica gel chromatography (dichloromethane/methanol/aqueous ammonia: 9/1/0.1) to afford 6.21 g of the title intermediate (56% yield).

Analytical Data: MS m/z 611.7 (MH$^+$).

Step F—Preparation of 4-{N-[7-(3-(S)-1-Carbamoyl-1,1-diphenylmethyl)pyrrolidin-1-yl)-4-oxahept-1-yl]-N-(isopropyl)amino}piperidine To a stirred solution of 4-{N-[7-(3-(S)-1-carbamoyl-1,1-diphenylmethyl)pyrrolidin-1-yl)-4-oxahept-1-yl]-N-(isopropyl)amino}-1-benzylpiperidine (9.3 g, 15.0 mmol) in acetic acid (100 mL) was added Pd(OH)$_2$ on carbon (0.90 g, 10% wt/wt) and Pd on carbon (0.90 g, 10% wt/wt). The reaction vessel was then evacuated and filled with hydrogen gas (3 times). The reaction mixture was allowed to stir at room temperature for 16 h and then flushed with nitrogen gas. The catalysts were removed by filtration and the filtrate was concentrated under reduced pressure to provide 7.18 g of the title intermediate, which was used without further purification (92% yield).

Analytical Data: MS m/z 521.3 (MH$^+$).

Example J

Preparation of 4-{N-[7-(3-(S)-1-Carbamoyl-1,1-diphenylmethyl)pyrrolidin-1-yl)-3-oxahept-1-yl]-N-(isopropyl)amino}piperidine

Step A—Preparation of N-(1-Benzylpiperdin-4-yl)-N-isopropyl 2-Chloroacetamide To a mixture of 1-benzyl-4-(isopropylamino)piperidine (8 g, 34.45 mmol) and DIPEA (7.2 mL, 41.3 mmol) in 200 mL of dichloromethane was added dropwise a solution of 2-chloroacetyl chloride (3.01 mL, 37.9 mmol) in dichloromethane (400 mL) at 0° C. The reaction mixture was stirred at 0° C. for 15 min and then at room temperature for 2 h. The reaction mixture was then washed with saturated sodium bicarbonate, brine, dried over magnesium sulfate and concentrated in vacuo. The resulting residue was purified by flash column chromatography (ethyl acetate/hexane/triethylamine: 42.5/56.5/1) to give 5.35 g of the title intermediate as a viscous oil (50% yield).

Analytical Data: MS: 309 (MH$^+$).

Step B—Preparation of N-(1-Benzylpiperdin-4-yl)-N-isopropyl 2-(4-Hydroxybut-1-oxy)acetamide 1,4-Butanediol (16 mL, 178 mmol) was refluxed with sodium hydroxide (970 mg, 24.3 mmol) in tert-butanol (8 mL) for 2 h at which time the solid sodium hydroxide had dissolved. The solution was then cooled to room temperature and a solution of N-(1-benzylpiperdin-4-yl)-N-isopropyl 2-chloroacetamide (5.0 g, 16.2 mmol) in tert-butanol (8 mL) was added dropwise. The reaction mixture was then stirred at room temperature overnight. After removal of tert-butanol under reduced pressure, the residue was dissolved in dichloromethane and this solution washed with sodium bicarbonate, water and brine. The organic layer was then dried over magnesium sulfate and concentrated. The residue was purified by flash column chromatography (dichloromethane/methanol/ammonium hydroxide: 90/9/1) to give 4.73 g of the title intermediate as a viscous oil (81% yield).

Analytical Data: MS: 363 (MH$^+$).

Step C—Preparation of 4-[N-(7-Hydroxy-3-oxahept-1-yl)-N-(isopropyl)amino-1-benzylpiperidine To a solution of N-(1-benzylpiperdin-4-yl)-N-isopropyl 2-(4-hydroxybut-1-oxy)acetamide (4.7 g, 13 mmol) in THF (30 mL) was slowly added 1 M lithium aluminum hydride in THF (20 mL, 19.5 mmol) at 0° C. The reaction mixture was stirred at room temperature overnight and then quenched by slow addition of 15% aqueous sodium hydroxide at 0° C. until no gas formation was observed. After stirring for 10 minutes at room temperature, a solid formed and the reaction mixture was filtered and the precipatate washed with THF three times. The filtrate was then concentrated and the residue was dissolved in dichloromethane and this solution was washed with brine, dried over magnesium sulfate and concentrated in vacuo to give 3.71 g of the title intermediate (82% yield).

Analytical Data: MS: 349 (MH$^+$).

Step D—Preparation of 4-[N-(7-Bromo-3-oxahept-1-yl)-N-(isopropyl)amino]-1-benzylpiperidine 4-[N-(7-Hydroxy-3-oxahept-1-yl)-N-(isopropyl)amino]-1-benzylpiperidine (3.7 g, 10.6 mmol) was treated with dibromotriphenylphosphorane (11.2 g, 26.6 mmol) in dichloromethane for 2 h. The reaction mixture was then was washed with 1 N sodium hydroxide, saturated sodium bicarbonate, brine, dried over magnesium sulfate and concentrated to give the title intermediate, which was used without further purification.

Step E—Preparation of 4-{N-[7-(3-(S)-1-Carbamoyl-1,1-diphenylmethyl)pyrrolidin-1-yl)-3-oxahept-1-yl]-N-(isopropyl)amino}-1-benzylpiperidine A mixture of 4-[N-(7-bromo-3-oxahept-1-yl)-N-(isopropyl)amino]-1-benzylpiperidine (from Step D), 3-(S)-1-carbamoyl-1,1-diphenylmethyl)pyrrolidine (3.28 g, 11.7 mmol) and triethylamine (4.5 mL, 31.9 mmol) in acetonitrile was refluxed for 24 h. The acetonitrile was removed under reduced pressure and the residue was dissolved in 1 N hydrochloric acid at a pH of about 1 to 2. After washing with ethyl acetate (4×), the aqueous layer was made basic with 50% aqueous sodium hydroxide to a pH of about 13 to 14 at 0° C. The aqueous layer was then extracted with dichloromethane (4×) and the combined organic layers were washed with saturated sodium bicarbonate, brine, dried over magnesium sulfate and concentrated in vacuo. The residue was purified by flash column chromatography (dichloromethane/methanol/ammonium hydroxide: 90/9/1) to give 2.08 g of the title intermediate as a white solid (32% yield).

Analytical Data: MS 611 (MH+).

Step F—Preparation of 4-{N-[7-(3-(S)-1-Carbamoyl-1,1-diphenylmethyl)pyrrolidin-1-yl)-3-oxahept-1-yl]-N-(isopropyl)amino}piperidine To a stirred solution of 4-{N-[7-(3-(S)-1-carbamoyl-1,1-diphenylmethyl)pyrrolidin-1-yl)-3-oxahept-1-yl]-N-(isopropyl)amino}-1-benzylpiperidine (2.08 g, 3.4 mmol) in acetic acid (30 mL) was added Pd(OH)$_2$ on carbon (0.20 g, 10% wt/wt) and Pd on carbon (0.20 g, 10% wt/wt). The reaction vessel was then evacuated and filled with hydrogen gas (3 times). The reaction was then allowed to stir at room temperature for 16 h. The reaction vessel was then flushed with nitrogen gas and the catalysts were removed by filtration. The filtrate was concentrated under reduced pressure to afford 1.69 g of the title intermediate, which was used without further purification (95% yield).

Analytical Data: MS 521 (MH+).

Example K

Preparation of 4-{N-[7-(3-(S)-1-Carbamoyl-1,1-diphenylmethyl)pyrrolidin-1-yl)-5-oxahept-1-yl]-N-(isopropyl)amino}-1-benzylpiperidine Step A—Preparation of N-(1-Benzylpiperdin-4-yl)-N-isopropyl 4-Chlorobutyramide A solution of 4-chlorobutyryl chloride (5.3 m]L, 47.4 mmol) in dichloromethane (400 mL) was added dropwise to a mixture of 1-benzyl-4-(isopropylamino)piperidine (10 g, 43.07 mmol) and DIPEA (9.0 mL, 51.7 mmol) in dichloromethane (200 mL) at 0° C. The reaction mixture was stirred at 0° C. for 15 min and then at room temperature for 2 h. The solution was then washed with saturated sodium bicarbonate, brine, dried over magnesium sulfate and concentrated in vacuo. The residue was purified by flash column chromatography (ethyl acetate/hexane/triethylamine: 42.5/56.5/1) to give 5.0 g of the title intermediate as viscous oil (35% yield).

Step B—Preparation of N-(1-Benzylpiperdin-4-yl)-N-isopropyl 4-(2-Hydroxyethoxy)butyramide A mixture of ethylene glycol (15 mL, 268 mmol) and N-(1-benzylpiperdin-4-yl)-N-isopropyl 4-chlorobutyramide (5.0 g, 14.9 mmol) was heated at 140° C. for 2 h in the presence of a catalytic amount p-toluenesulfonic acid. The reaction mixture was then dissolved in dichloromethane and the solution washed with 1 N sodium hydroxide, aqueous sodium bicarbonate solution and brine; and dried over MgSO$_4$ and concentrated in vacuo. The residue was purified by flash column chromatography (dichloromethane/methanol/ammonium hydroxide: 90/9/1) to give 2.72 g of the title intermediate as viscous oil (51% yield).

Step C—Preparation of 4-[N-(7-Hydroxy-5-oxahept-1-yl)-N-(isopropyl)amino]-1-benzylpiperidine To a solution of N-(1-benzylpiperdin-4-yl)-N-isopropyl 4-(2-hydroxyethoxy)butyramide (2.7 g, 7.5 mmol) in THF (20 mL) was slowly added 1 M lithium aluminum hydride in THF (11.3 mL, 11.3 mmol) at 0° C. The reaction mixture was stirred at room temperature overnight and then quenched by slow addition of 15% aqueous sodium hydroxide at 0° C. until no gas formation was observed. After stirring for 10 minutes at room temperature, a solid formed and the reaction mixture was filtered and the precipatate washed with THF three times. The filtrate was then concentrated and the residue was dissolved in dichloromethane and this solution was washed with brine, dried over magnesium sulfate and concentrated in vacuo to give 2.13 g of the title intermediate (82% yield).

Step D—Preparation of 4-[N-(7-Bromo-5-oxahept-1-yl)-N-(isopropyl)amino]-1-benzylpiperidine 4-[N-(7-Hydroxy-5-oxahept-1-yl)-N-(isopropyl)amino]-1-benzylpiperidine (2.0 g, 5.7 mmol) was treated with dibromotriphenylphosphorane (6.1 g, 14.4 mmol) in dichloromethane for 2 h. The reaction mixture was then washed with 1 N sodium hydroxide, saturated sodium bicarbonate, brine, dried over magnesium sulfate and concentrated to give the title intermediate, which was used without further purification.

Step E—Preparation of 4-{N-[7-(3-(S)-1-Carbamoyl-1,1-diphenylmethyl)pyrrolidin-1-yl)-5-oxahept-1-yl]-N-(isopropyl)amino}-1-benzylpiperidine A mixture of 4-[N-(7-bromo-3-oxahept-1-yl)-N-(isopropyl)amino]-1-benzylpiperidine (from Step D), 3-(S)-1-carbamoyl-1,1-diphenylmethyl)pyrrolidine (1.8 g, 6.3 mmol) and triethylamine (2.4 mL, 17.3 mmol) in acetonitrile was refluxed for 24 h. The acetonitrile was removed under reduced pressure and the residue was dissolved in 1 N hydrochloric acid at a pH of about 1 to 2. After washing with ethyl acetate (4×), the aqueous layer was made basic with 50% aqueous sodium hydroxide to a pH of about 13 to 14 at 0° C. The aqueous layer was then extracted with dichloromethane (4×) and the combined organic layers were washed with saturated sodium bicarbonate, brine, dried over magnesium sulfate and concentrated in vacuo. The residue was purified by flash column chromatography (dichloromethane/methanol/ammonium hydroxide: 90/9/1) to give 1.02 g of the title intermediate as a white solid (29% yield).

Example L

Preparation of (S)-3-(1-Carbamoyl-1,1-diphenylmethyl)-1-(7-oxohept-1-yl)pyrrolidine Step A—Preparation of 7,7-Dimethoxyheptanal Cycloheptene was added to a three-neck round-bottom flask containing low water UV-grade methanol (0.5 M concentration). The reaction mixture was cooled to −78° C., and ozone was bubbled through for 45 minutes. The solution was purged with nitrogen in order to prevent over oxidation. p-Toluenesulfonic acid (10 mol %) was added, and the reaction mixture was slowly warmed to 0° C. (two hours total reaction time). The acid was neutralized by adding excess solid sodium bicarbonate (4.0 equivalents) and after the mixture was stirred for 15 minutes, dimethyl sulfide (2.2 eq) was added. After 16 h, the reaction mixture was concentrated by solvent removal on rotary evaporator. Water was added (10 mL/g) and the heterogeneous mixture was stirred for 30 minutes. The crude product was extracted with MTBE (2×20 mL/g) and the combined organic extracts were dried with sodium sulfate and concentrated under reduced pressure. The crude product was purified by vacuum distillation (observed b.p. 80-85° C., at a pressure of about 1.0 mm) to give the title intermediate.

Step B—Preparation of (S)-3-(1-Carbamoyl-1,1-diphenylmethyl)-1-(7,7-dimethoxyhept-1-yl)pyrrolidine To a three-necked 50 L flask equipped with a mechanical stirrer, a nitrogen inlet, cooling bath and a thermometer was added (S)-3-(1-carbamoyl-1,1-diphenylmethyl)pyrrolidine (2.5 kg, 8.93 mol) and dichloromethane (20 L) and this mixture was stirred until the solid dissolved. The reaction mixture was then cooled to 0° C. and 7,7-dimethoxyheptanal (1.71 kg, 9.82 mol) was added slowly while maintaining the reaction temperature below 5° C. This reaction mixture was stirred at 0 to 5° C. for 1 hr and then sodium triacetoxyborohydride (2.27 kg, 10.72 mol) was added in small portions over 30 minutes while maintaining the reaction temperature below 5° C. The reaction mixture was then stirred at room temperature for 6 hrs. An aqueous 5% potassium carbonate solution (20 L) was then added while maintaining the reaction temperature below 20° C. and the reaction mixture was then stirred for 1 hr at room temperature. The layers were then separated and the organic layer was washed with brine (10 L) and then dried over sodium sulfate (2 kg) for about 3 hrs. After separating the organic layer from the sodium sulfate, the organic layer was concentrated to about 10 L under reduced pressure. This mixture was then purified by silica gel chromatography (40 kg) using the following sequence of eluents: dichloromethane (100 L); 3% MeOH, 97% DCM, as needed; 5% MeOH, 95% DCM, as needed; and 10% MeOH, 90% DCM, as needed. The fractions containing the desired intermediate were then combined ($R_f$ 0.3; 10% MeOH/90% DCM) and concentrated at a temperature less than 30° C. to afford 3.3 kg of the title intermediate.

Step C—Preparation of (S)-3-(1-Carbamoyl-1,1-diphenylmethyl)-1-(7-oxohept-1-yl)pyrrolidine To a three-necked 50 L flask equipped with a mechanical stirrer, a nitrogen inlet, cooling bath and a thermometer was added the intermediate from Step B (3.3 kg, 7.25 mol) and acetonitrile (15 L). This mixture was cooled to less than 10° C. and an aqueous 1 N hydrochloric acid solution (15 L) was added while maintaining the reaction temperature less than 20° C. The reaction mixture was then stirred at room temperature for 2 to 5 hrs. Dichloromethane (20 L) was then added and this mixture was stirred for 30 minutes and then separated. The aqueous layer was extracted with dichloromethane (2×10 L) and the combined organic layers were washed with brine (20 L) and dried over sodium sulfate (4 kg) for at least 3 hours. After separating the organic layer from the sodium sulfate, the organic layer was concentrated to about 20 L under reduced pressure at a temperature less than 25° C. This solution containing about 1.5 kg of the title intermediate, as the hydrochloride salt, was used in subsequent reactions without further purification. Alternatively, if desired, the solution can be further concentrated and the resulting residue purified by conventional procedures.

Example 1

Synthesis of 4-{N-[7-(3-(S)-1-Carbamoyl-1,1-diphenylmethyl)pyrrolidin-1-yl)hept-1-yl]-N-(isopropyl)amino}-1-(4-methoxypyrid-3-ylmethyl)piperidine Method A: To a 50 mL flask equipped with a nitrogen inlet was added (S)-3-(1-carbamoyl-1,1-diphenylmethyl)-1-(7-oxohept-1-yl)pyrrolidine (2.36 g, 6.0 mmol); 4-isopropylamino-1-(4-methoxypyrid-3-ylmethyl)piperidine (1.61 g, 6.1 mmol) and dichloromethane (12 mL). This mixture was stirred at room temperature for 1 hour and then sodium triacetoxyborohydride (1.65 g, 7.8 mmol) was added and stirring was continued at room temperature for 20 hours (at which time essentially all of the starting pyrrolidine compound had reacted as determined by HPLC). The reaction was then quenched by the addition of 6 N aqueous hydrochloric acid (12 mL) and the layers were separated. The aqueous layer was washed with dichloromethane (12 mL) and, after separation, isopropyl acetate (40 mL) was added to the aqueous layer. The aqueous layer was then made basic to pH 14 by adding 10 N aqueous sodium hydroxide solution (alternatively, conc. ammonium hydroxide may be used). The layers were separated and the organic layer was washed with saturated aqueous sodium chloride solution (40 mL); and dried over sodium sulfate (5 g). The sodium sulfate was filtered off, and solvent was removed in vacuo to give 2.4 g of crude product as a light yellow foamy solid (63% yield; $R_f$ 0.4 with $CH_2Cl_2$/MeOH/$NH_4OH$=88:10:2). The crude product was further purified by $SiO_2$ chromatography (60 g, $SiO_2$, $CH_2Cl_2$/MeOH/$NH_4OH$=90:10:1 (300 mL) to 85:15:1 (300 mL)). The appropriate fractions were combined to give 0.98 g of the title compound as a white solid (26% yield; 98% purity by HPLC Method A).

Method B: Alternatively, the title compound was prepared by the following procedure:

Step A—Synthesis of 4-{N-[7-(3-(S)-1-Carbamoyl-1,1-diphenylmethyl)pyrrolidin-1-yl)hept-2-yn-1-yl]-N-(isopropyl)amino}-1-(4-methoxypyrid-3-ylmethyl)piperidine To a stirred solution of (S)-3-(1-carbamoyl-1,1-diphenylmethyl)-1-(hex-5-yn-1-yl)pyrrolidine (17.8 g, 49.4 mmol), paraformaldehyde (1.93 g, 64.2 mmol) and 4-isopropylamino-1-(4-methoxypyrid-3-ylmethyl)piperidine (14.3 g, 54.3 mmol) in THF (247 mL) under nitrogen at 55° C., was added copper (I) chloride (0.978 g, 9.88 mmol). The reaction mixture was stirred at 55° C. for 5 hours and then the solvent was removed under reduced pressure. The crude residue was dissolved in dichloromethane (250 mL) and filtered through Celite, washing with dichloromethane (50 mL). The filterate was washed with 5 N sodium hydroxide (3×100 mL) and the dried over magnesium sulfate (10 g). The solvent was then removed in vacuo to provide 29.8 g of the title intermediate as a pale yellow solid (95% yield).

Step B—Synthesis of 4-{N-[7-(3-(S-1-Carbamoyl-1,1-diphenylmethyl)pyrrolidin-1-yl)hept-1-yl]-N-(isopropyl)amino}-1-(4-methoxypyrid-3-ylmethyl)piperidine The alkyne from Step A (28.4 g, 47 mmol) and p-toluenesulfonhydrazide (87.5 g, 470 mmol) were dissolved in DME (700 mL) and brought to reflux (ca. 85° C.). A solution of sodium acetate (77.1 g, 940 mmol) in water (470 mL) was then added dropwise at the rate of about 20 mL/hour and the reaction mixture was continually refluxed for 18 hours. The reaction mixture was then allowed to cool to room temperature and 10 N sodium hydroxide was added to adjust the pH to 12. The organic layer was separated and the aqueous layer was extracted with ethyl acetate (2×400 mL). The combined organic layers were washed with 1 N sodium hydroxide (2×350 mL) and then extracted using 1 N hydrochloric acid (2×350 mL). The combined acidic aqueous extracts were made basic to pH 12 with 10 N sodium hydroxide and extracted with ethyl acetate (2×400 mL). The combined organic layers were washed with saturated aqueous sodium chloride solution (400 mL), and dried over magnesium sulfate (10 g). The magnesium sulfate was filtered off and washed with ethyl acetate (200 mL) and the solvent removed in vacuo to give the title compound.

Method C: Alternatively, the title compound was prepared by the following procedure:

Step A—Preparation of 7,7-Dimethoxyheptanal

Cycloheptene (20.0 g, 0.208 mol) was added to a three-neck round-bottom flask containing low water UV-grade methanol (0.5 M concentration). The reaction mixture was cooled to −78° C., and ozone was bubbled through for 45 minutes. The solution was purged with nitrogen in order to prevent over oxidation. p-Toluenesulfonic acid (3.96 g, 0.021 mol) was added, and the reaction mixture was slowly warmed to 0° C. (two hours total reaction time). The acid was neutralized by adding excess solid sodium bicarbonate (69.9 g, 0.832 mol) and after the mixture was stirred for 15 minutes, dimethyl sulfide (28.6 g, 0.46 mol) was added. After 16 h, the reaction mixture was concentrated by solvent removal on rotary evaporator. Water was added (10 mL/g) and the heterogeneous mixture was stirred for 30 minutes. The crude product was extracted with MTBE (2×20 mL/g) and the combined organic extracts were dried with sodium sulfate and concentrated under reduced pressure. The crude product was purified by vacuum distillation (observed b.p. 80-85° C., at a pressure of about 1.0 mm) to give 28.95 g of the title intermediate.

Step B—Preparation of (S)-3-(1-Carbamoyl-1,1-diphenylmethyl)-1-(7,7-dimethoxyhept-1-yl)pyrrolidine To a three-necked 500 mL flask equipped with a mechanical stirrer, a nitrogen inlet, cooling bath, and a thermometer was added (S)-3-(1-carbamoyl-1,1-diphenylmethyl)pyrrolidine (25 g, 0.089 mol) and dichloromethane (200 m]L). This mixture was cooled to about 0° C. and 7,7-dimethoxyheptanal (18.6 g, 0.107 mol) was added slowly. During the addition, the reaction temperature was maintained at 5° C. or less. The resulting mixture was stirred at 0 to 5° C. for 1 hour and then sodium triacetoxyborohydride (24.6 g, 0.116 mol) was then added over a 30 minute period. During this addition, the reaction temperature was also maintained at 5° C. or less. The resulting mixture was then stirred at 0 to 5° C. for 6 hours. The reaction was then quenched by adding 5% aqueous potassium carbonate solution (200 mL) while keeping the reaction temperature less than about 20° C. and the resulting mixture was stirred for 1 hour at room temperature. The organic layer was separated and washed with brine (100 mL) and then dried with sodium sulfate (20 g). The organic layer was then concentrated under vacuum to a volume of about 100 mL and this mixture was purified by silica gel chromatography eluting with a gradient of 1 to 10% v/v methanol in dichloromethane. The fractions containing the desired product were combined and concentrated under vacuum to afford 28 g of the title intermediate as an oil (72% yield).

Analytical Data: $^1$HNMR(CDCl$_3$) δ: 7.44-7.15 (m, 10H); 5.88 (s, 2H); 4.33 (t, J=6.7 Hz, 1H);3.70-3.58 (m, 1H); 3.30 (s, 6H); 3.10-2.92 (m, 3H); 2.76-2.64 (m, 1H); 2.61-2.52 (m, 2H); 2.30 (m, 1H); 2.20 (m, 1H); 1.56 (m, 4H); 1.26 (m, 7H).

Step C—Preparation of (S)-3-(1-Carbamoyl-1,1-diphenylmethyl)-1-(7-oxohept-1-yl)pyrrolidine To a three-necked 500 μL flask equipped with a mechanical stirrer, a nitrogen inlet, cooling bath, and a thermometer was added (S)-3-(1-carbamoyl-1,1-diphenylmethyl)-1-(7,7-dimethoxyhept-1-yl)pyrrolidine (16 g, 0.036 mol) and acetonitrile (100 mL). This mixture was cooled to about 10° C. and 100 mL of 1N aqueous hydrochloric acid was added while maintaining the reaction temperature at 20° C. or less. The resulting mixture was stirred at 20±5° C. for 2 hours. The reaction mixture was then extracted with dichloromethane (1×200 mL and 2×100 mL). The combined organic layers were washed with brine (200 mL) and dried with sodium sulfate (40 g). The organic layer was then concentrated under vacuum at about 25° C. to a volume of about 200 mL. This solution, containing the title intermediate as the hydrochloride salt, was used directly in the next step without further purification.

Step D—Preparation of 4-{N-[7-(3-(S)-1-Carbamoyl-1,1-diphenylmethyl)pyrrolidin-1-yl)hept-1-yl]-N-(isopropyl)amino}-1-(4-methoxypyrid-3-ylmethyl)piperidine To a three-necked 500 mL flask equipped with a mechanical stirrer, a nitrogen inlet, cooling bath, and a thermometer was added 4-isopropylamino-1-(4-methoxypyrid-3-ylmethyl)piperidine benzoate (14.1 g, 0.036 mol) and (S)-3-(1-carbamoyl-1,1-diphenylmethyl)-1-(7-oxohept-1-yl)pyrrolidine hydrochloride salt solution (200 mL) from Step C above. This mixture was stirred at room temperature for 1 hour and then cooled to 10 to 15° C. Sodium triacetoxyborohydride (9.3 g, 0.044 mol) was added portionwise over 30 minutes and the resulting mixture was stirred at room temperature for 15 to 20 hours. The reaction mixture was then cooled to 0 to 10° C. and the reaction quenched by adding 6 N aqueous hydrochloric acid (200 mL) while maintaining the reaction temperature at 25° C. or less. The aqueous layer was separated and washed with dichloromethane (3×100 mL) and then made basic to about pH 12 by adding concentrated aqueous ammonium hydroxide. The resulting mixture was extracted with dichloromethane (1×200 mL and 1×100 mL) and the combined organic layers were washed with water (100 mL) and then concentration under vacuum. The resulting residue was dissolved in MTBE (250 mL) and the MTBE solution was then washed with water (3×100 mL), brine (100 mL), dried over sodium sulfate (30 g) and filtered. The MTBE solution was then concentrated under vacuum to give 19 g of the title compound as an oil (81.5% yield; 94.9% purity by HPLC Method D).

The title compound (1 g) was purified by silica gel chromatography eluting with a gradient of 3% to 10% v/v methanol in dichloromethane containing 0.5% concentrated ammonium hydroxide. The fractions containing the title compound were combined and concentrated under vacuum to give 0.6 g to the title compound as an oil (98.6% purity by HPLC Method D).

Analytical Data: $^1$HNMR(CDCl$_3$) δ: 8.41 (s, 1H); 8.39 (d, J=5.7 Hz, 1H); 7.44-7.41 (m, 2H); 7.33-7.14 (m, 8H); 6.76 (d, J=5.6 Hz, 1H); 5.74 (s, 2H); 3.85 (s, 3H); 3.52 (s, 2H); 3.42 (m 1H); 3.10-2.78 (m, 4H); 2.70-2.25 (m, 8H); 2.10-1.85 (m, 3H); 1.70-1.52 (m, 4H); 1.48-1.15 (m, 10H); 0.97 (d J=6.6 Hz, 6H).

The di(methanesulfonic acid) salt of the title compound was prepared as follows:

To a 5 L flask was added 4-{N-[7-(3-(S)-1-carbamoyl-1,1-diphenylmethyl)pyrrolidin-1-yl)hept-1-yl]-N-(isopropyl)amino}-1-(4-methoxypyrid-3-ylmethyl)piperidine (593 g, 0.93 mol) and 1.44 L of absolute ethanol and the mixture was stirred to dissolve the oil. This mixture was then cooled to 0-5° C. and a solution of 142.5 g of methanesulfonic acid (142.5 g, 1.48 mol) in 98 mL of absolute ethanol was added at 5° C. The mixture was stirred at 5-10° C. for 1 h and then it was added to 37.5 L of MTBE slowly and this mixture was stirred for 30 min at 10-15° C. The resulting solid was filtered and dissolved in 5 L of distilled water. The water solution was treated with activated carbon (70 g) and filtered. The filtrate was frozen at −40° C. and lyophilized for 72 hours to give 481 g of the di(methanesulfonic acid) (79% yield, 99.1% purity by HPLC).

The tri(methanesulfonic acid) salt of the title compound was prepared as follows:

A 100 mL Erlenmeyer flask was charged with 4-{N-[7-(3-(S)-1-carbamoyl-1,1-diphenylmethyl)pyrrolidin-1-yl)hept-1-yl]-N-(isopropyl)amino}-1-(4-methoxypyrid-3-ylmethyl)piperidine (3.9 g, 6.1 mmol) and acetonitrile (32 mL) and upon dissolution, water (25 mL) and methanesulfonic acid (1.29 mL, 1.91 g, 19.9 mmol) were added to bring the pH to about 5. The solution was then frozen in a dry ice/acetone bath and lyophilized for 48 h to afford 5.5 g of the tri(methanesulfonic acid) salt as an off-white solid (100% yield; 97.4% purity by HPLC).

Analytical Data: MS m/z 640.5 (MH$^+$).

The naphthalene-1,5-disulfonic acid salt of the title compound was prepared as follows:

To a 100 mL flask was added 4-{N-[7-(3-(S)-1-carbamoyl-1,1-diphenylmethyl)pyrrolidin-1-yl)hept-1-yl]-N-(isopropyl)amino}-1-(4-methoxypyrid-3-ylmethyl)piperidine (10.45 g, 16.33 mmol) and methanol (53 mL). After the compound dissolved, the solution was cooled to about 10° C. and naphthalene-1,5-disulfonic acid tetrahydrate (4.37 g, 15.15 mmol) was added portionwise while maintaining the reaction temperature below 10° C. When the addition was complete, the reaction mixture was stirred for 30 minutes. The reaction mixture was then added slowly over 2 h to a mixture of isopropanol (530 mL) and MTBE (265 mL) at 0-5° C. This mixture was then stirred for 1 hour and the resulting solid was filtered and washed with MTBE (50 mL). The solid was then dried under vacuum at room temperature for 5 days. During this time, the solid was removed from the drying chamber on days 2 and 4 and run through a ball mill (400 rpm, 3×2 minutes). This process provided 12 g of the title salt (80% yield) as an amorphous white powder (98.9% purity by HPLC; 65.1% free base content relative to reference standard).

Analytical Data: FTIR (cm$^{-1}$): 1671.7 (w), 1593.5 (w), 1497.6 (w), 1291.2 (w), 1220.9 (m), 1180.3 (m), 1030.1 (s); MS m/z 640.8 (MH$^+$ free base); 928.8 (MH$^+$ free base+salt); Anal. Calcd for $C_{50}H_{65}N_5O_8S_2$: C, 63.30; H, 7.52; N, 7.14; S, 6.15. Found: C, 63.53; H, 7.65; N, 7.23; S, 6.30.

This salt had a molar ratio of naphthalene-1,5-disulfonic acid to 4-{N-[7-(3-(S)-1-carbamoyl-1,1-diphenylmethyl)pyrrolidin-1-yl)hept-1-yl]-N-(isopropyl)amino}-1-(4-methoxypyrid-3-ylmethyl)piperidine of about 0.95 tol as determined by $^1$H NMR (ratio of naphthalene ring protons to pyridine ring protons).

If desired, the naphthalene-1,5-disulfonic acid salts of this invention can be further purified using the following slurry procedure: To the naphthalene-1,5-disulfonic acid salt of 4-{N-[7-(3-(S)-1-carbamoyl-1,1-diphenylmethyl)pyrrolidin-1-yl)hept-1-yl]-N-(isopropyl)amino}-1-(4-methoxypyrid-3-ylmethyl)piperidine (8.0 g) was added isopropanol (80 mL). The resulting slurry was stirred for 6 hrs at room temperature. The mixture was then filtered and the solids were washed with MTBE (2×40 mL) and then dried under vacuum and nitrogen for 16 hours to afford 7.8 g to the title compound (97.5% recovery by weight).

Example 2

Synthesis of 4-{N-[7-(3-(S)-1-Carbamoyl-1,1-diphenylmethyl)pyrrolidin-1-yl)-4-oxahept-1-yl]-N-(isopropyl)amino}-1-(4-methoxypyrid-3-ylmethyl)piperidine To a stirred solution of 4-{N-[7-(3-(S)-1-carbamoyl-1,1-diphenylmethyl)-pyrrolidin-1-yl)-4-oxahept-1-yl]-N-(isopropyl)amino}piperidine (500 mg, 0.96 mmol) in dichloromethane (10 mL) was added 4-methoxy-3-pyridinecarboxaldehyde (145 mg, 1.06 mmol) and sodium triacetoxyborohydride (426 mg, 1.9 mmol). The reaction mixture was stirred for 14 h and then the solvent was removed under reduced pressure. To the resulting mixture was added 1:1 ethyl acetate/water (1.0 mL) and this mixture was chromatographed on reverse-phase silica gel (gradient elution, acetonitrile/H$_2$O) to afford 289 mg of the title compound (47% yield).

Analytical Data: MS m/z 642.5 (MH$^+$); R$_f$ 1.43 (10-70 ACN:H$_2$O, reverse phase HPLC).

Example 3

Synthesis of 4-{N-[7-(3-(S)-1-Carbamoyl-1,1-diphenylmethyl)pyrrolidin-1-yl)-3-oxahept-1-yl]-N-(isopropyl)amino}-1-(4-methoxypyrid-3-ylmethyl)piperidine To a stirred solution of 4-{N-[7-(3-(S)-1-carbamoyl-1,1-diphenylmethyl)-pyrrolidin-1-yl)-3-oxahept-1-yl]-N-(isopropyl)amino}piperidine (52 mg, 0.1 mmol) in dichloroethane (1 mL) was added 4-methoxy-3-pyridinecarboxaldehyde (13.7 mg, 0.1 mmol) and sodium triacetoxyborohydride (24 mg, 1.05 mmol). The reaction mixture was stirred for 14 h and then the solvent was removed under reduced pressure. To the resulting residue was added a 1:1 acetic acid/water mixture (1.0 mL) and this mixture was chromatographed on reverse-phase silica gel (gradient elution, acetonitrile/water) to afford 27 mg of the title compound (42% yield).

Analytical Data: MS 642(MH$^+$).

Example 4

Synthesis of 4-{N-[7-(3-(S)-1-Carbamoyl-1,1-diphenylmethyl)pyrrolidin-1-yl)hept-1-yl]-N-(ethyl)amino}-1-(2-methoxypyrid-3-ylmethyl)piperidine To a stirred solution of 4-{N-[7-(3-(S)-1-carbamoyl-1,1-diphenylmethyl)-pyrrolidin-1-yl)hept-1-yl]-N-(ethyl)amino}piperidine (50.5 mg, 0.1 mmol) in dichloromethane (1 mL) was added 2-methoxypyridine-3-carboxaldehyde (205.7 mg, 0.15 mmol) and sodium triacetoxyborohydride (33 mg, 0.15 mmol). The reaction mixture was stirred for 14 h and then the solvent was removed under reduced pressure. To the resulting mixture was added 1:1 acetic acid/water (1.0 mL) and the mixture was chromatographed on reverse-phase silica gel (gradient elution, acetonitrile/$H_2O$) to afford the title compound.

Analyical Data: MS m/z 626.4 ($MH^+$); $R_f$ 2.11 (2-75 ACN: $H_2O$, reverse phase HPLC).

Example 5

Synthesis of 4-{N-[7-(3-(S)-1-Carbamoyl-1,1-diphenylmethyl)pyrrolidin-1-yl)hept-1-yl]-N-(ethyl)amino}-1-(3-methoxypyrid-2-ylmethyl)piperidine Using the procedure of Example 4 and substituting 3-methoxypyridine-2-carboxaldehyde in place of 2-methoxypyridine-3-carboxaldehyde, the title compound was prepared.

Analytical Data: MS m/z 626.4 ($MH^+$); $R_f$ 2.08 (2-75 ACN: $H_2O$, reverse phase HPLC).

Example 6

Synthesis of 4-{N-[7-(3-(S)-1-Carbamoyl-1,1-diphenylmethyl)pyrrolidin-1-yl)hept-1-yl]-N-(ethyl)amino}-1-(4-methoxypyrid-3-ylmethyl)piperidine Using the procedure of Example 4 and substituting 4-methoxypyridine-3-carboxaldehyde in place of 2-methoxypyridine-3-carboxaldehyde, the title compound was prepared.

Analytical Data: MS m/z 626.4 ($MH^+$); $R_f$ 2.04 (10-70 ACN: $H_2O$, reverse phase HPLC).

Example 7

Synthesis of 4-{N-[7-(3-(S)-1-Carbamoyl-1,1-diphenylmethyl)pyrrolidin-1-yl)-4-oxahept-1-yl]-N-(ethyl)amino}-1-(4-methoxypyrid-3-ylmethyl)piperidine Using the procedures of Example I and Example 2 and substituting 1-benzyl-4-(ethylamino)piperidine for 1-benzyl-4-(isopropylamino)piperidine, the title compound was prepared.

Example 36

Synthesis of 4-{N-[7-(3-(S)-1-Carbamoyl-1,1-diphenylmethyl)pyrrolidin-1-yl)hept-1-yl]-N-(isopropyl)amino}-1-(4-n-propoxypyrid-3-ylmethyl)piperidine Using the procedure of Example 1 and substituting 4-isopropylamino-1-(4-n-propoxypyrid-3-ylmethyl)piperidine in place of 4-isopropylamino-1-(4-methoxypyrid-3-ylmethyl)piperidine, the title compound was prepared. In this reaction, 1.2 equivalents of acetic acid (based on the 1.0 equivalents of the aldehyde) was added to the reaction mixture during the reductive alkylation reaction. The title compound was purified by reverse phase HPLC to afford the title compound as the tris-trifluoroacetic acid salt.

Analytical Data: MS m/z 668.4 ($MH^+$).

Example 37

Synthesis of 4-{N-[7-(3-(S)-1-Carbamoyl-1,1-diphenylmethyl)pyrrolidin-1-yl)hept-1-yl]-N-(isopropyl)amino}-1-(4-isopropoxypyrid-3-ylmethyl)piperidine Using the procedure of Example 1 and substituting 4-isopropylamino-1-(4-isopropoxypyrid-3-ylmethyl)piperidine in place of 4-isopropylamino-1-(4-methoxypyrid-3-ylmethyl)piperidine, the title compound was prepared. In this reaction, 1.2 equivalents of acetic acid (based on the 1.0 equivalents of the aldehyde) was added to the reaction mixture during the reductive alkylation reaction. The title compound was purified by reverse phase HPLC to afford the title compound as the tris-trifluoroacetic acid salt.

Analytical Data: MS m/z 668.4 ($MH^+$).

Example 98

Synthesis of 4-{N-[7-(3-(S)-1-Carbamoyl-1,1-diphenylmethyl)pyrrolidin-1-yl)hept-1-yl]-N-(isopropyl)amino}-1-(4-ethoxypyrid-3-ylmethyl)piperidine Step A—Preparation of 4-Chloropyridine To a solution of potassium bicarbonate (10.21 g, 0.102 mol) in water (50 mL) at 0° C. was added 50 mL of dichloromethane. 4-Chloropyridine hydrochloride (15.0 g, 0.1 mmol) was then added portionwise and the resulting mixture was stirred at 0° C. for 30 min. The layers were separated and the aqueous layer was extracted with dichloromethane (1×30 mL). The organic layers were combined, dried over sodium sulfate, filtered and the solvent removed in vacuo to afford 4-chloropyridine as a very light yellow oil.

Step B—Preparation of 4-Chloropyridine-3-carboxaldehyde

To a solution of diisopropylamine (18.2 mL, 0.13 mol) in THF (200 mL, 0.5 M) at −78° C. was added n-butyl lithium (2.5 M in hexane, 52 mL, 0.13 mol) dropwise. After 30 min, 4-chloropyridine from Step A in THF (10 mL) was added and the reaction mixture was stirred at −78° C. for 1 h. To the resulting reddish-brown solution at −78° C. was added N,N-dimethylformamide (12.4 mL, 0.16 mol). The reaction mixture was allowed to warm slowly to room temperature over a 15 h period, and then the reaction was quenched with water (150 mL). The THF was removed in vacuo and the aqueous layer was extracted with isopropyl acetate (3×150 mL). The organic layers were combined, dried over sodium sulfate, filtered and the solvent was removed in vacuo to give the crude product as a brown oil. This residue was purified by silica gel chromatography (using 5% EtOH in EtOAc) to afford 3.97 g of the title intermediate as a yellow solid ($R_f$=0.6, 28% yield).

Analytical Data: $^1$H NMR ($CDCl_3$, 300 MHz) δ: 10.48 (s, 1H), 9.02 (s, 1H), 8.65 (d, J=5.6 Hz, 1H), 7.41 (d, J=5.6 Hz, 1H); LC-MS m/z 141.9 (expected 141.55 for $C_4H_6ClNO$).

Step C—Preparation of 4-{N-[7-(3-(S)-1-Carbamoyl-1,1-diphenylmethyl)pyrrolidin-1-yl)hept-1-yl]-N-(isopropyl)amino}-1-(4-chloropyrid-3-ylmethyl)piperidine A solution of 4-{N-[7-(3-(S)-1-carbamoyl-1,1-diphenylmethyl)pyrrolidin-1-yl)hept-1-yl]-N-(isopropyl)amino}piperidine (0.56 g, 1.085 mmol) and 4-chloropyridine-3-carboxaldehyde (169 mg, 1.19 mmol) in 1,2-dichloroethane (11 mL, 0.1 M) was stirred at room temperature for 2 h. Acetic acid (75 μL, 1.30 mmol) was added and then sodium triacetoxyborohydride (299 mg, 1.41 mmol) was added. After 64 h, the reaction was quenched by adding aqueous 10% sodium carbonate (10 mL). The layers were separated and the aqueous layer was made basic by adding aqueous 1N sodium hydroxide until the pH was about 13 to 14. The aqueous layer was then extracted with dichloromethane (2×15 mL) and the organic layers were combined, dried over sodium sulfate, filtered and the solvent was removed in vacuo. The resulting residue (a yellow oil) was purified by silica gel chromatography (using $CH_2Cl_2$/$CH_3OH$/aqueous $NH_4OH$=84/15/1) to afford 0.46 g of the title intermediate as a very light yellow thick oil ($R_f$=0.2; 66% yield).

Analytical Date: LCMS m/z 644.3 (expected 644.34 for $C_{39}H_{54}ClN_5O$).

Step D—Preparation of 4-{N-[7-(3-(S)-1-Carbamoyl-1,1-diphenylmethyl)pyrrolidin-1-yl)hept-1-yl]-N-(isopropyl)amino}-1-(4-ethoxypyrid-3-ylmethyl)piperidine Sodium metal (109 mg, 4.74 mmol) was added to ethanol (3 mL) to form a solution of sodium ethoxide in ethanol. This solution was added to a solution of 4-{N-[7-(3-(S)-1-carbamoyl-1,1-diphenylmethyl)pyrrolidin-1-yl)hept-1-yl]-N-(isopropyl)amino}-(4-chloropyrid-3-ylmethyl)piperidine (304.6 mg, 0.47 mmol) in ethanol (0.2 mL). The resulting reaction mixture was heated to 80° C. and another aliquot of sodium ethoxide in ethanol (3 mL) was added (for a total volume of about 6 mL). The reaction was monitored by MS and when no further starting material was detected, most of the ethanol was removed in vacuo. The resulting residue was purified by RP-HPLC to afford 213 mg of the title compound as a white amorphous solid.

Analytical Data: $^1$H NMR ($CD_3OD$, 300 MHz) δ: 8.79 (s, 1H), 8.75 (d, J=6.9 Hz, 1H), 7.64 (d, J=6.9 Hz, 1H), 7.29-7.42 (m, 10H), 4.48 (q, J=7.2 Hz, 2H), 4.37 (s, 2H), 3.30-3.99 (m, 7H), 2.82-3.21 (m, 7H), 1.88-2.63 (m, 7H), 1.52-1.74 (m, 4H), 1.56 (t, J=7.2 Hz, 3H, overlapped), 1.28-1.42 (m, 12H) ppm; LC-MS m/z 654.5 (expected 693.94 for $C_{41}H_{59}N_5O_2$).

Example 99

Synthesis of 4-{N-[7-(3-(S)-1-Carbamoyl-1,1-diphenylmethyl)pyrrolidin-1-yl)hept-1-yl]-N-(isopropyl)amino}-1-(4-trifluromethoxypyrid-3-ylmethyl)piperidine Using the procedure of Example 1 and substituting 4-isopropylamino-1-(4-isopropoxypyrid-3-ylmethyl)piperidine in place of 4-isopropylamino-1-(4-methoxypyrid-3-ylmethyl)piperidine, the title compound was prepared. In this reaction, 1.2 equivalents of acetic acid (based on the 1.0 equivalents of the aldehyde) was added to the reaction mixture during the reductive alkylation reaction. The title compound was purified by reverse phase HPLC to afford the title compound as the tris-trifluoroacetic acid salt.

Analytical Data: MS m/z 672.4 (MH$^+$).

Example 115

Synthesis of 4-{N-[7-(3-(S)-1-Carbamoyl-1,1-diphenylmethyl)pyrrolidin-1-yl)hept-1-yl]-N-(isopropyl)amino}-1-[4-(2-fluoroethoxy)pyrid-3-ylmethyl]piperidine Using the procedure of Example 1 and substituting 4-isopropylamino-1-[4-(2-fluoroethoxy)pyrid-3-ylmethyl]piperidine in place of 4-isopropylamino-1-(4-methoxypyrid-3-ylmethyl)piperidine, the title compound was prepared. In this reaction, 1.2 equivalents of acetic acid (based on the 1.0 equivalents of the aldehyde) was added to the reaction mixture during the reductive alkylation reaction. The title compound was purified by reverse phase HPLC to afford the title compound as the tris-trifluoroacetic acid salt.

Analytical Data: MS nm/z 694.4 (MH$^+$).

Using the procedures described herein, the following compounds can be prepared:

Example 8—4-{N-[8-(3-(S)-1-Carbamoyl-1,1-diphenylmethyl)pyrrolidin-1-yl)oct-1-yl]-N-(ethyl)amino}-1-(4-methoxypyrid-3-ylmethyl)piperidine;

Example 9—4-{N-[9-(3-(S)-1-Carbamoyl-1,1-diphenylmethyl)pyrrolidin-1-yl)non-1-yl]-N-(ethyl)amino}-1-(4-methoxypyrid-3-ylmethyl)piperidine;

Example 10—4-{N-[7-(3-(S)-1-Carbamoyl-1,1-diphenylmethyl)pyrrolidin-1-yl)-3-oxahept-1-yl]-N-(ethyl)amino}-1-(4-methoxypyrid-3-ylmethyl)piperidine;

Example 11—4-{N-[8-(3-(S)-1-Carbamoyl-1,1-diphenylmethyl)pyrrolidin-1-yl)-3-oxaoct-1-yl]-N-(ethyl)amino}-1-(4-methoxypyrid-3-ylmethyl)piperidine;

Example 12—4-{N-[9-(3-(S)-1-Carbamoyl-1,1-diphenylmethyl)pyrrolidin-1-yl)-3-oxanon-1-yl]-N-(ethyl)amino}-1-(4-methoxypyrid-3-ylmethyl)piperidine;

Example 13—4-{N-[8-(3-(S)-1-Carbamoyl-1,1-diphenylmethyl)pyrrolidin-1-yl)-4-oxaoct-1-yl]-N-(ethyl)amino}-1-(4-methoxypyrid-3-ylmethyl)piperidine;

Example 14—4-{N-[9-(3-(S)-1-Carbamoyl-1,1-diphenylmethyl)pyrrolidin-1-yl)-4-oxanon-1-yl]-N-(ethyl)amino}-1-(4-methoxypyrid-3-ylmethyl)piperidine;

Example 15—4-{N-[7-(3-(S)-1-Carbamoyl-1,1-diphenylmethyl)pyrrolidin-1-yl)-5-oxahept-1-yl]-N-(ethyl)amino}-1-(4-methoxypyrid-3-ylmethyl)piperidine;

Example 16—4-{N-[8-(3-(S)-1-Carbamoyl-1,1-diphenylmethyl)pyrrolidin-1-yl)-5-oxaoct-1-yl]-N-(ethyl)amino}-1-(4-methoxypyrid-3-ylmethyl)piperidine;

Example 17—4-{N-[9-(3-(S)-1-Carbamoyl-1,1-diphenylmethyl)pyrrolidin-1-yl)-5-oxanon-1-yl]-N-(ethyl)amino}-1-(4-methoxypyrid-3-ylmethyl)piperidine;

Example 18—4-{N-[8-(3-(S)-1-Carbamoyl-1,1-diphenylmethyl)pyrrolidin-1-yl)-6-oxaoct-1-yl]-N-(ethyl)amino}-1-(4-methoxypyrid-3-ylmethyl)piperidine;

Example 19—4-{N-[9-(3-(S)-1-Carbamoyl-1,1-diphenylmethyl)pyrrolidin-1-yl)-6-oxanon-1-yl]-N-(ethyl)amino}-1-(4-methoxypyrid-3-ylmethyl)piperidine;

Example 20—4-{N-[9-(3-(S)-1-Carbamoyl-1,1-diphenylmethyl)pyrrolidin-1-yl)-7-oxanon-1-yl]-N-(ethyl)amino}-1-(4-methoxypyrid-3-ylmethyl)piperidine;

Example 21—4-{N-[7-(3-(S)-1-Carbamoyl-1,1-diphenylmethyl)pyrrolidin-1-yl)hep-1-yl]-N-(prop-1-yl)amino}-1-(4-methoxypyrid-3-ylmethyl)piperidine;

Example 22—4-{N-[8-(3-(S)-1-Carbamoyl-1,1-diphenylmethyl)pyrrolidin-1-yl)oct-1-yl]-N-(prop-1-yl)amino}-1-(4-methoxypyrid-3-ylmethyl)piperidine;

Example 23—4-{N-[9-(3-(S)-1-Carbamoyl-1,1-diphenylmethyl)pyrrolidin-1-yl)non-1-yl]-N-(prop-1-yl)amino}-1-(4-methoxypyrid-3-ylmethyl)piperidine;

Example 24—4-{N-[7-(3-(S)-1-Carbamoyl-1,1-diphenylmethyl)pyrrolidin-1-yl)-3-oxahept-1-yl]-N-(prop-1-yl)amino}-1-(4-methoxypyrid-3-ylmethyl)piperidine;

Example 25—4-{N-[8-(3-(S)-1-Carbamoyl-1,1-diphenylmethyl)pyrrolidin-1-yl)-3-oxaoct-1-yl]-N-(prop-1-yl)amino}-1-(4-methoxypyrid-3-ylmethyl)piperidine;

Example 26—4-{N-[9-(3-(S)-1-Carbamoyl-1,1-diphenylmethyl)pyrrolidin-1-yl)-3-oxanon-1-yl]-N-(prop-1-yl)amino}-1-(4-methoxypyrid-3-ylmethyl)piperidine;

Example 27—4-{N-[7-(3-(S)-1-Carbamoyl-1,1-diphenylmethyl)pyrrolidin-1-yl)-4-oxahep-1-yl]-N-(prop-1-yl)amino}-1-(4-methoxypyrid-3-ylmethyl)piperidine;

Example 28—4-{N-[8-(3-(S)-1-Carbamoyl-1,1-diphenylmethyl)pyrrolidin-1-yl)-4-oxaoct-1-yl]-N-(prop-1-yl)amino}-1-(4-methoxypyrid-3-ylmethyl)piperidine;

Example 29—4-{N-[9-(3-(S)-1-Carbamoyl-1,1-diphenylmethyl)pyrrolidin-1-yl)-4-oxanon-1-yl]-N-(prop-1-yl)amino}-1-(4-methoxypyrid-3-ylmethyl)piperidine;

Example 30—4-{N-[7-(3-(S)-1-Carbamoyl-1,1-diphenylmethyl)pyrrolidin-1-yl)-5-oxahept-1-yl]-N-(prop-1-yl)amino}-1-(4-methoxypyrid-3-ylmethyl)piperidine;

Example 31—4-{N-[8-(3-(S)-1-Carbamoyl-1,1-diphenylmethyl)pyrrolidin-1-yl)-5-oxaoct-1-yl]-N-(prop-1-yl)amino}-1-(4-methoxypyrid-3-ylmethyl)piperidine;

Example 32—4-{N-[9-(3-(S)-1-Carbamoyl-1,1-diphenylmethyl)pyrrolidin-1-yl)-5-oxanon-1-yl]-N-(prop-1-yl)amino}-1-(4-methoxypyrid-3-ylmethyl)piperidine;

Example 33—4-{N-[8-(3-(S)-1-Carbamoyl-1,1-diphenylmethyl)pyrrolidin-1-yl)-6-oxaoct-1-yl]-N-(prop-1-yl)amino}-1-(4-methoxypyrid-3-ylmethyl)piperidine;

Example 34—4-{N-[9-(3-(S)-1-Carbamoyl-1,1-diphenylmethyl)pyrrolidin-1-yl)-6-oxanon-1-yl]-N-(prop-1-yl)amino}-1-(4-methoxypyrid-3-ylmethyl)piperidine;

Example 35—4-{N-[9-(3-(S)-1-Carbamoyl-1,1-diphenylmethyl)pyrrolidin-1-yl)-7-oxanon-1-yl]-N-(prop-1-yl)amino}-1-(4-methoxypyrid-3-ylmethyl)piperidine;

Example 38—4-{N-[7-(3-(S)-1-Carbamoyl-1,1-diphenylmethyl)pyrrolidin-1-yl)hep-1-yl]-N-(isopropyl)amino}-1-(4-cyclopropyl-methoxypyrid-3-ylmethyl)piperidine;

Example 39—4-{N-[7-(3-(S)-1-Carbamoyl-1,1-diphenylmethyl)pyrrolidin-1-yl)hep-1-yl]-N-(isopropyl)amino}-1-{4-(2-hydroxyethoxy)pyrid-3-ylmethyl)piperidine;

Example 40—4-{N-[7-(3-(S)-1-Carbamoyl-1,1-diphenylmethyl)pyrrolidin-1-yl)hep-1-yl]-N-(isopropyl)amino}-1-(4-isobutoxypyrid-3-ylmethyl)piperidine;

Example 41—4-{N-[7-(3-(S)-1-Carbamoyl-1,1-diphenylmethyl)pyrrolidin-1-yl)hep-1-yl]-N-(isopropyl)amino}-1-(2,4-dimethoxypyrid-3-ylmethyl)piperidine;

Example 42—4-{N-[7-(3-(S)-1-Carbamoyl-1,1-diphenylmethyl)pyrrolidin-1-yl)hep-1-yl]-N-(isopropyl)amino}-1-(2-fluoro-4-methoxypyrid-3-ylmethyl)piperidine;

Example 43—4-{N-[7-(3-(S)-1-Carbamoyl-1,1-diphenylmethyl)pyrrolidin-1-yl)hep-1-yl]-N-(isopropyl)amino}-1-(2-chloro-4-methoxypyrid-3-ylmethyl)piperidine;

Example 44—4-{N-[7-(3-(S)-1-Carbamoyl-1,1-diphenylmethyl)pyrrolidin-1-yl)hep-1-yl]-N-(isopropyl)amino}-1-(2-methyl-4-methoxypyrid-3-ylmethyl)piperidine;

Example 45—4-{N-[8-(3-(S)-1-Carbamoyl-1,1-diphenylmethyl)pyrrolidin-1-yl)oct-1-yl]-N-(isopropyl)amino}-1-(4-methoxypyrid-3-ylmethyl)piperidine;

Example 46—4-{N-[9-(3-(S)-1-Carbamoyl-1,1-diphenylmethyl)pyrrolidin-1-yl)non-1-yl]-N-(isopropyl)amino}-1-(4-methoxypyrid-3-ylmethyl)piperidine;

Example 47—4-{N-[7-(3-(S)-1-Carbamoyl-1,1-diphenylmethyl)pyrrolidin-1-yl)hep-1-yl]-N-(isopropyl)amino}-1-(3-methoxypyrid-2-ylmethyl)piperidine;

Example 48—4-{N-[8-(3-(S)-1-Carbamoyl-1,1-diphenylmethyl)pyrrolidin-1-yl)oct-1-yl]-N-(isopropyl)amino}-1-(3-methoxypyrid-2-ylmethyl)piperidine;

Example 49—4-{N-[9-(3-(S)-1-Carbamoyl-1,1-diphenylmethyl)pyrrolidin-1-yl)non-1-yl]-N-(isopropyl)amino}-1-(3-methoxypyrid-2-ylmethyl)piperidine;

Example 50—4-{N-[7-(3-(S)-1-Carbamoyl-1,1-diphenylmethyl)pyrrolidin-1-yl)hep-1-yl]-N-(isopropyl)amino}-1-(3-methoxypyrid-4-ylmethyl)piperidine;

Example 51—4-{N-[8-(3-(S)-1-Carbamoyl-1,1-diphenylmethyl)pyrrolidin-1-yl)oct-1-yl]-N-(isopropyl)amino}-1-(3-methoxypyrid-4-ylmethyl)piperidine;

Example 52—4-{N-[9-(3-(S)-1-Carbamoyl-1,1-diphenylmethyl)pyrrolidin-1-yl)non-1-yl]-N-(isopropyl)amino}-1-(3-methoxypyrid-4-ylmethyl)piperidine;

Example 53—4-{N-[7-(3-(S)-1-Carbamoyl-1,1-diphenylmethyl)pyrrolidin-1-yl)hep-1-yl]-N-(isopropyl)amino}-1-(2-methoxypyrid-3-ylmethyl)piperidine;

Example 54—4-{N-[8-(3-(S)-1-Carbamoyl-1,1-diphenylmethyl)pyrrolidin-1-yl)oct-1-yl]-N-(isopropyl)amino}-1-(2-methoxypyrid-3-ylmethyl)piperidine;

Example 55—4-{N-[9-(3-(S)-1-Carbamoyl-1,1-diphenylmethyl)pyrrolidin-1-yl)non-1-yl]-N-(isopropyl)amino}-1-(2-methoxypyrid-3-ylmethyl)piperidine;

Example 56—4-{N-[7-(3-(S)-1-Carbamoyl-1,1-diphenylmethyl)pyrrolidin-1-yl)-3-oxahept-1-yl]-N-(isopropyl)amino}-1-(4-methoxypyrid-3-ylmethyl)piperidine;

Example 57—4-{N-[8-(3-(S)-1-Carbamoyl-1,1-diphenylmethyl)pyrrolidin-1-yl)-3-oxaoct-1-yl]-N-(isopropyl)amino}-1-(4-methoxypyrid-3-ylmethyl)piperidine;

Example 58—4-{N-[9-(3-(S)-1-Carbamoyl-1,1-diphenylmethyl)pyrrolidin-1-yl)-3-oxanon-1-yl]-N-(isopropyl)amino}-1-(4-methoxypyrid-3-ylmethyl)piperidine;

Example 59—4-{N-[7-(3-(S)-1-Carbamoyl-1,1-diphenylmethyl)pyrrolidin-1-yl)-4-oxahep-1-yl]-N-(isopropyl)amino}-1-(4-methoxypyrid-3-ylmethyl)piperidine;

Example 60—4-{N-[9-(3-(S)-1-Carbamoyl-1,1-diphenylmethyl)pyrrolidin-1-yl)-4-oxanon-1-yl]-N-(isopropyl)amino}-1-(4-methoxypyrid-3-ylmethyl)piperidine;

Example 61—4-{N-[8-(3-(S)-1-Carbamoyl-1,1-diphenylmethyl)pyrrolidin-1-yl)-5-oxaoct-1-yl]-N-(isopropyl)amino}-1-(4-methoxypyrid-3-ylmethyl)piperidine;

Example 62—4-{N-[9-(3-(S)-1-Carbamoyl-1,1-diphenylmethyl)pyrrolidin-1-yl)-5-oxanon-1-yl]-N-(isopropyl)amino}-1-(4-methoxypyrid-3-ylmethyl)piperidine;

Example 63—4-{N-[8-(3-(S)-1-Carbamoyl-1,1-diphenylmethyl)pyrrolidin-1-yl)-6-oxaoct-1-yl]-N-(isopropyl)amino}-1-(4-methoxypyrid-3-ylmethyl)piperidine;

Example 64—4-{N-[9-(3-(S)-1-Carbamoyl-1,1-diphenylmethyl)pyrrolidin-1-yl)-6-oxanon-1-yl]-N-(isopropyl)amino}-1-(4-methoxypyrid-3-ylmethyl)piperidine;

Example 65—4-{N-[9-(3-(S)-1-Carbamoyl-1,1-diphenylmethyl)pyrrolidin-1-yl)-7-oxanon-1-yl]-N-(isopropyl)amino}-1-(4-methoxypyrid-3-ylmethyl)piperidine;

Example 66—4-{N-[7-(3-(S)-1-Carbamoyl-1,1-diphenylmethyl)pyrrolidin-1-yl)hep-1-yl]-N-(cyclopropylmethyl)amino}-1-(4-methoxypyrid-3-ylmethyl)piperidine;

Example 67—4-{N-[8-(3-(S)-1-Carbamoyl-1,1-diphenylmethyl)pyrrolidin-1-yl)oct-1-yl]-N-(cyclopropylmethyl)amino}-1-(4-methoxypyrid-3-ylmethyl)piperidine;

Example 68—4-{N-[9-(3-(S)-1-Carbamoyl-1,1-diphenylmethyl)pyrrolidin-1-yl)non-1-yl]-N-(cyclopropylmethyl)amino}-1-(4-methoxypyrid-3-ylmethyl)piperidine;

Example 69—4-{N-[7-(3-(S)-1-Carbamoyl-1,1-diphenylmethyl)pyrrolidin-1-yl)-3-oxahept-1-yl]-N-(cyclopropylmethyl)amino}-1-(4-methoxypyrid-3-ylmethyl)piperidine;

Example 70—4-{N-[8-(3-(S)-1-Carbamoyl-1,1-diphenylmethyl)pyrrolidin-1-yl)-3-oxaoct-1-yl]-N-(cyclopropylmethyl)amino}-1-(4-methoxypyrid-3-ylmethyl)piperidine;

Example 71—4-{N-[9-(3-(S)-1-Carbamoyl-1,1-diphenylmethyl)pyrrolidin-1-yl)-3-oxanon-1-yl]-N-(cyclopropylmethyl)amino}-1-(4-methoxypyrid-3-ylmethyl)piperidine;

Example 72—4-{N-[7-(3-(S)-1-Carbamoyl-1,1-diphenylmethyl)pyrrolidin-1-yl)-4-oxahep-1-yl]-N-(cyclopropylmethyl)amino}-1-(4-methoxypyrid-3-ylmethyl)piperidine;

Example 73—4-{N-[8-(3-(S)-1-Carbamoyl-1,1-diphenylmethyl)pyrrolidin-1-yl)-4-oxaoct-1-yl]-N-(cyclopropylmethyl)amino}-1-(4-methoxypyrid-3-ylmethyl)piperidine;

Example 74—4-{N-[9-(3-(S)-1-Carbamoyl-1,1-diphenylmethyl)pyrrolidin-1-yl)-4-oxanon-1-yl]-N-(cyclopropylmethyl)amino}-1-(4-methoxypyrid-3-ylmethyl)piperidine;

Example 75—4-{N-[7-(3-(S)-1-Carbamoyl-1,1-diphenylmethyl)pyrrolidin-1-yl)-5-oxahept-1-yl]-N-(cyclopropylmethyl)amino}-1-(4-methoxypyrid-3-ylmethyl)piperidine;

Example 76—4-{N-[8-(3-(S)-1-Carbamoyl-1,1-diphenylmethyl)pyrrolidin-1-yl)-5-oxaoct-1-yl]-N-(cyclopropylmethyl)amino}-1-(4-methoxypyrid-3-ylmethyl)piperidine;

Example 77—4-{N-[9-(3-(S)-1-Carbamoyl-1,1-diphenylmethyl)pyrrolidin-1-yl)-5-oxanon-1-yl]-N-(cyclopropylmethyl)amino}-1-(4-methoxypyrid-3-ylmethyl)piperidine;

Example 78—4-{N-[8-(3-(S)-1-Carbamoyl-1,1-diphenylmethyl)pyrrolidin-1-yl)-6-oxaoct-1-yl]-N-(cyclopropylmethyl)amino}-1-(4-methoxypyrid-3-ylmethyl)piperidine;

Example 79—4-{N-[9-(3-(S)-1-Carbamoyl-1,1-diphenylmethyl)pyrrolidin-1-yl)-6-oxanon-1-yl]-N-(cyclopropylmethyl)amino}-1-(4-methoxypyrid-3-ylmethyl)piperidine;

Example 80—4-{N-[9-(3-(S)-1-Carbamoyl-1,1-diphenylmethyl)pyrrolidin-1-yl)-7-oxanon-1-yl]-N-(cyclopropylmethyl)amino}-1-(4-methoxypyrid-3-ylmethyl)piperidine;

Example 81—4-{N-[7-(3-(S)-1-Carbamoyl-1,1-diphenylmethyl)pyrrolidin-1-yl)hep-1-yl]-N-(2-hydroxyethyl)amino}-1-(4-methoxypyrid-3-ylmethyl)piperidine;

Example 82—4-{N-[8-(3-(S)-1-Carbamoyl-1,1-diphenylmethyl)pyrrolidin-1-yl)oct-1-yl]-N-(2-hydroxyethyl)amino}-1-(4-methoxypyrid-3-ylmethyl)piperidine;

Example 83—4-{N-[9-(3-(S)-1-Carbamoyl-1,1-diphenylmethyl)pyrrolidin-1-yl)non-1-yl]-N-(2-hydroxyethyl)amino}-1-(4-methoxypyrid-3-ylmethyl)piperidine;

Example 84—4-{N-[7-(3-(S)-1-Carbamoyl-1,1-diphenylmethyl)pyrrolidin-1-yl)-3-oxahept-1-yl]-N-(2-hydroxyethyl)amino}-1-(4-methoxypyrid-3-ylmethyl)piperidine;

Example 85—4-{N-[8-(3-(S)-1-Carbamoyl-1,1-diphenylmethyl)pyrrolidin-1-yl)-3-oxaoct-1-yl]-N-(2-hydroxyethyl)amino}-1-(4-methoxypyrid-3-ylmethyl)piperidine;

Example 86—4-{N-[9-(3-(S)-1-Carbamoyl-1,1-diphenylmethyl)pyrrolidin-1-yl)-3-oxanon-1-yl]-N-(2-hydroxyethyl)amino}-1-(4-methoxypyrid-3-ylmethyl)piperidine;

Example 87—4-{N-[7-(3-(S)-1-Carbamoyl-1,1-diphenylmethyl)pyrrolidin-1-yl)-4-oxahep-1-yl]-N-(2-hydroxyethyl)amino}-1-(4-methoxypyrid-3-ylmethyl)piperidine;

Example 88—4-{N-[8-(3-(S)-1-Carbamoyl-1,1-diphenylmethyl)pyrrolidin-1-yl)-4-oxaoct-1-yl]-N-(2-hydroxyethyl)amino}-1-(4-methoxypyrid-3-ylmethyl)piperidine;

Example 89—4-{N-[9-(3-(S)-1-Carbamoyl-1,1-diphenylmethyl)pyrrolidin-1-yl)-4-oxanon-1-yl]-N-(2-hydroxyethyl)amino}-1-(4-methoxypyrid-3-ylmethyl)piperidine;

Example 90—4-{N-[7-(3-(S)-1-Carbamoyl-1,1-diphenylmethyl)pyrrolidin-1-yl)-5-oxahept-1-yl]-N-(2-hydroxyethyl)amino}-1-(4-methoxypyrid-3-ylmethyl)piperidine;

Example 91—4-{N-[8-(3-(S)-1-Carbamoyl-1,1-diphenylmethyl)pyrrolidin-1-yl)-5-oxaoct-1-yl]-N-(2-hydroxyethyl)amino}-1-(4-methoxypyrid-3-ylmethyl)piperidine;

Example 92—4-{N-[9-(3-(S)-1-Carbamoyl-1,1-diphenylmethyl)pyrrolidin-1-yl)-5-oxanon-1-yl]-N-(2-hydroxyethyl)amino}-1-(4-methoxypyrid-3-ylmethyl)piperidine;

Example 93—4-{N-[8-(3-(S)-1-Carbamoyl-1,1-diphenylmethyl)pyrrolidin-1-yl)-6-oxaoct-1-yl]-N-(2-hydroxyethyl)amino}-1-(4-methoxypyrid-3-ylmethyl)piperidine;

Example 94—4-{N-[9-(3-(S)-1-Carbamoyl-1,1-diphenylmethyl)pyrrolidin-1-yl)-6-oxanon-1-yl]-N-(2-hydroxyethyl)amino}-1-(4-methoxypyrid-3-ylmethyl)piperidine;

Example 95—4-{N-[9-(3-(S)-1-Carbamoyl-1,1-diphenylmethyl)pyrrolidin-1-yl)-7-oxanon-1-yl]-N-(2-hydroxyethyl)amino}-1-(4-methoxypyrid-3-ylmethyl)piperidine;

Example 96—4-{N-[7-(3-(S)-1-Carbamoyl-1,1-diphenylmethyl)pyrrolidin-1-yl)hep-1-yl]-N-(isopropyl)amino}-1-(4-tert-butoxypyrid-3-ylmethyl)piperidine;

Example 97—4-{N-[7-(3-(S)-1-Carbamoyl-1,1-diphenylmethyl)pyrrolidin-1-yl)hep-1-yl]-N-(isopropyl)amino}-1-(4-hydroxypyrid-3-ylmethyl)piperidine;

Example 100—4-{N-[7-(3-(S)-1-Carbamoyl-1,1-diphenylmethyl)pyrrolidin-1-yl)hep-1-yl]-N-(isopropyl)amino}-1-(4-difluoromethoxypyrid-3-ylmethyl)piperidine;

Example 101—4-{N-[7-(3-(S)-1-Carbamoyl-1,1-diphenylmethyl)pyrrolidin-1-yl)hep-1-yl]-N-(isopropyl)amino}-1-(4-methoxy-2-trifluoromethoxypyrid-3-ylmethyl)piperidine;

Example 102—4-{N-[7-(3-(S)-1-Carbamoyl-1,1-diphenylmethyl)pyrrolidin-1-yl)hep-1-yl]-N-(isopropyl)amino}-1-(2-difluoromethoxy-4-methoxypyrid-3-ylmethyl)piperidine;

Example 103—4-{N-[7-(3-(S)-1-Carbamoyl-1,1-diphenylmethyl)pyrrolidin-1-yl)hep-1-yl]-N-(isopropyl)amino}-1-(2-methoxy-4-trifluoromethoxypyrid-3-ylmethyl)piperidine;

Example 104—4-{N-[7-(3-(S)-1-Carbamoyl-1,1-diphenylmethyl)pyrrolidin-1-yl)hep-1-yl]-N-(isopropyl)amino}-1-(4-difluoromethoxy-2-methoxypyrid-3-ylmethyl)piperidine;

Example 105—4-{N-[7-(3-(S)-1-Carbamoyl-1,1-diphenylmethyl)pyrrolidin-1-yl)hep-1-yl]-N-(isopropyl)amino}-1-{2,4-di(trifluoromethoxy)pyrid-3-ylmethyl}piperidine;

Example 106—4-{N-[7-(3-(S)-1-Carbamoyl-1,1-diphenylmethyl)pyrrolidin-1-yl)hep-1-yl]-N-(isopropyl)amino}-1-{2,4-di(difluoromethoxy)pyrid-3-ylmethyl}piperidine;

Example 107—4-{N-[7-(3-(S)-1-Carbamoyl-1,1-diphenylmethyl)pyrrolidin-1-yl)hep-1-yl]-N-(isopropyl)amino}-1-(2-ethoxy-4-trifluoromethoxypyrid-3-ylmethyl)piperidine;

Example 108—4-{N-[7-(3-(S)-1-Carbamoyl-1,1-diphenylmethyl)pyrrolidin-1-yl)hep-1-yl]-N-(isopropyl)amino}-1-(2-ethoxy-4-difluoromethoxypyrid-3-ylmethyl)piperidine;

Example 109—4-(N-[7-(3-(S)-1-Carbamoyl-1,1-diphenylmethyl)pyrrolidin-1-yl)hep-1-yl]-N-(isopropyl)amino}-1-(2,4-diethoxypyrid-3-ylmethyl)piperidine;

Example 110—4-{N-[7-(3-(S)-1-(N-Methylcarbamoyl)-1,1-diphenylmethyl)pyrrolidin-1-yl)hep-1-yl]-N-(isopropyl)amino}-1-(4-methoxypyrid-3-ylmethyl)piperidine;

Example 111—4-{N-[7-(3-(S)-1-(N,N-Dimethylcarbamoyl)-1,1-diphenylmethyl)pyrrolidin-1-yl)hep-1-yl]-N-(isopropyl)amino}-1-(4-hydroxypyrid-3-ylmethyl)piperidine;

Example 112—4-{N-[7-(3-(S)-1-(N,N-Diethylcarbamoyl)-1,1-diphenylmethyl)pyrrolidin-1-yl)hep-1-yl]-N-(isopropyl)amino}-1-(4-hydroxypyrid-3-ylmethyl)piperidine;

Example 113—4-{N-[7-(3-(S)-1-(Piperidin-1-ylcarbonyl)-1,1-diphenylmethyl)pyrrolidin-1-yl)hep-1-yl]-N-(isopropyl)amino}-1-(4-hydroxypyrid-3-ylmethyl)piperidine;

Example 114—4-{N-[7-(3-(S)-1-(Morpholin-4-ylcarbonyl)-1,1-diphenylmethyl)pyrrolidin-1-yl)hep-1-yl]-N-(isopropyl)amino}-1-(4-hydroxypyrid-3-ylmethyl)piperidine; and Example 116—4-{N-[7-(3-(R)-1-Carbamoyl-1,1-diphenylmethyl)pyrrolidin-1-yl)hep-1-yl]-N-(isopropyl)amino}-1-(4-methoxypyrid-3-ylmethyl)piperidine;

Example 117—4-{N-[7-(3-(R)-1-Carbamoyl-1,1-diphenylmethyl)pyrrolidin-1-yl)hep-1-yl]-N-(isopropyl)amino}-1-(4-ethoxypyrid-3-ylmethyl)piperidine.

Example 118

Radioligand Binding Assay

A. Membrane Preparation from Cells Expressing $hM_1$, $hM_2$, $hM_3$ and $hM_4$ Muscarinic Receptor Subtypes CHO (Chinese hamster ovary) cell lines stably expressing cloned human $hM_1$, $hM_2$, $hM_3$ and $hM_4$ muscarinic receptor subtypes, respectively, were grown to near confluency in medium consisting of HAM's F-12 supplemented with 10% FBS (Fetal Bovine Serum) and 250 µg/mL Geneticin. The cells were grown in a 5% $CO_2$, 37° C. incubator and lifted with dPBS+2 mM EDTA. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. Protein concentration of the membrane suspension was determined by the method of Lowry, O. et al., (1951) *Journal of Biochemistry:* 193, 265. Membranes were stored frozen in aliquots at −80° C.

Aliquots of prepared $hM_5$ receptor membranes were purchased directly from Perkin Elmer and stored at −80° C. until use.

B. Radioligand Binding Assay on Muscarinic Receptor Subtypes $hM_1$, $hM_2$, $hM_3$, $hM_4$ and $hM_5$ Radioligand binding assays were performed in 96-well microtiter plates in a total assay volume of 100 µL. Membranes containing each of the respective muscarinic subtypes were diluted in assay buffer to the following specific target protein concentrations (Lg/well): 10 µg for $hM_1$, 10-15 µg for $hM_2$, 10-20 µg for $hM_3$, 18-20 µg for $hM_4$, and 10-12 µg for $hM_5$. The membranes were briefly homogenized using a Polytron tissue disruptor (10 seconds) prior to assay plate addition. Saturation binding studies for determining $K_D$ values of the radioligand were performed using 1-[N-methyl-$^3$H]scopolamine methyl chloride ([$^3$H]NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H] NMS at 1 nM and eleven different test compound concentrations. The test compounds were initially dissolved to a concentration of 400 µM in dilution buffer and then serially diluted 5× with dilution buffer to final concentrations ranging from 10 pM to 100 µM. The addition order and volumes to the assay plates were as follows: 25 µL radioligand, 25 µL diluted test compound, and 50 µL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. Plates were air dried, and 50 µL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology,* 22(23):3099-108). $K_i$ values were converted to $pK_i$ values to determine the geometric mean and 95% confidence intervals. These summary statistics were then converted back to $K_i$ values for data reporting.

Test compounds having a lower $K_i$ value in this assay have a higher binding affinity for the muscarinic receptor. The compounds of this invention which were tested in this assay had a $K_i$ value for $hM_2$ ranging from about 200 nM to less than 1 nM; typically ranging from about 100 nM to less than 1 mM. Additionally, compounds of this invention which were tested in this assay had an $hM_3/hM_2$ ratio ranging from about 5 to greater than 50; typically ranging from about 20 to greater than 50. By way of example, the compound of Example 1 had a $K_i$ value for $hM_2$ of less than 1 nM and an $hM_3/hM_2$ ratio greater than 40.

Thus, compounds of this invention were found to bind potently to the $hM_2$ receptor subtype in this assay and to have a higher binding affinity for the $hM_2$ receptor subtype relative to the $hM_3$ receptor subtype.

Example 119

Muscarinic Receptor Functional Potency Assays

A. Blockade of Agonist-Mediated Inhibition of cAMP Accumulation

In this assay, the functional potency of a test compound was determined by measuring the ability of the test compound to block oxotremorine-inhibition of forskolin-mediated cAMP accumulation in CHO-K 1 cells expressing the $hM_2$ receptor.

cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

CHO-K1 cells stably expressing cloned human $M_2$ muscarinic receptors were grown to near confluency in a 5% $CO_2$, 37° C. incubator in medium consisting of HAM's F-12 supplemented with 10% FBS (Fetal Bovine Serum) and 250 µg/mL Geneticin. On the day of the assay, cells were rinsed once with dPBS and lifted with Trypsin. The detached cells were washed twice by centrifugation at 650×g for five minutes in 50 mLs dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of $1.6 \times 10^6$-$2.8 \times 10^6$ cells/mL.

The test compound was initially dissolved to a concentration of 400 µM in dilution buffer (dPBS supplemented with 1 mg/mL BSA (0.1%)), and then serially diluted with dilution buffer to final molar concentrations ranging from 1E-4 M to 1E-10 M. Oxotremorine was diluted in a similar manner.

To measure oxotremorine inhibition of adenylyl cyclase (AC) activity, 25 µL forskolin (25 µM final concentration diluted in dPBS), 25 µL diluted oxotremorine, and 50 µL cells were added to agonist assay wells. To measure the ability of a test compound to block oxotremorine-inhibited AC activity, 25 µL forskolin and oxotremorine (25 µM and 5 µM final concentrations, respectively, diluted in dPBS) 25 µL diluted test compound, and 50 µL cells were added to remaining assay wells.

Reactions were incubated for 10 minutes at 37° C. and stopped by addition of 100 µL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $EC_{50}$ of the oxotremorine concentration-response curve and the oxotremorine assay concentration as the $K_D$ and [L], respectively. The $K_i$ values were converted to $pK_i$ values to determine the geometric mean and 95% confidence intervals. These summary statistics were then converted back to $K_i$ values for data reporting.

Typically, compounds of this invention that were tested in this assay had a $K_i$ of less than about 100 nM for blockade of oxotremorine-inhibition of forskolin-mediated cAMP accumulation in CHO-K1 cells expressing the $hM_2$ receptor. For example, the compound of Example 1 had a $K_i$ of less than about 1 nM.

B. Blockade of Agonist-Mediated GTPγ[$^{35}$S] Binding

In this assay, the functional potency of a test compound was determined by measuring the ability of the test compound to block carbachol-stimulated GTPγ[$^{35}$S] binding in CHO-K1 cells expressing the $hM_2$ receptor.

CHO-K1 cells stably expressing the $hM_2$ muscarinic receptor were grown in medium consisting of Hams F-12 media supplemented with 10% Fetal Bovine Serum and 500 µg/ml of Geneticin (G-418). Cells were incubated in a 5% $CO_2$, humidified incubator at 37° C. Cells were grown to confluence and harvested with dPBS+2 mM EDTA and pelleted by centrifugation at 250×g for 10 minutes.

Cells from the centrifuged pellets were resuspended in homogenization buffer (10 mM HEPES, 10 mM EDTA, pH 7 at 4° C.). Cells were then homogenized using a Polytron PT-2100 tissue disrupter (Kinematica AG) for six, 3 second bursts. Crude membranes were pelleted at 40,000×g for 15 minutes at 4° C. Membranes were finally resuspended in assay buffer (10 mM HEPES, 100 mM NaCl, 10 mM $MgCl_2$, pH 7.4 at 37° C.) and frozen at −80° C.

At the time of use, membranes were thawed and then diluted in assay buffer with a final target tissue concentration of 7 µg protein per well. The membranes were briefly homogenized using a Polytron PT-2100 tissue disrupter and then added to the assay plates.

The $EC_{90}$ value (effective concentration for 90% maximal response) for stimulation of GTPγ[$^{35}$S] binding by the agonist carbachol was determined in each experiment as follows: 25 µL of a 5× carbachol working stock solution, 25 µL assay buffer containing GTPγ[$^{35}$S] and GDP, 25 µL membrane, and 25 µL assay buffer were transferred to the 96-well microtiter plates. The final concentration of GTPγ [$^{35}$S] was 0.07 nM and the final concentration of GDP was 3 µM. The assay plate was then incubated at 37° C. for 60 minutes prior to filtration.

To determine the ability of a test compound to inhibit carbachol-stimulated GTPγ[$^{35}$S] binding, the following was added to each well of 96 well plates: 25 µL of assay buffer with GTPγ[35] and GDP, 25 µL of diluted test compound (prepared as described above), and 25 µL CHO cell membranes expressing the $hM_2$ receptor. The plates were pre-incubated at 37° C. for 15 minutes. After the pre-incubation period, 25 µL of carbachol at the final concentration of its $EC_{90}$ value determined earlier in the day was added to each plate. The assay plates were then incubated at 37° C. for an additional 60 minutes.

Following the 60 minute carbachol incubation period, the assay plates were filtered over 0.5% bovine serum albumin-pretreated glass fiber GF/B filtermats using a PerkinElmer 96-well harvester. The plates were rinsed with ice-cold wash buffer for 3×3 seconds and then air or vacuum dried. Microscint-20 scintillation liquid (40 mL) was added to each well, and each plate was sealed and radioactivity determined on a TopCount (PerkinElmer) scintillation counter.

Test compound potency ($IC_{50}$) was determined using iterative curve fitting (GraphPad Prism 3.0 software; single site competition curve). The inhibition dissociation constant ($K_i$) of the test compound was determined with the Prism program considering the concentration of the agonist carbachol and the effective concentration for 50% response ($EC_{50}$) determined in the same experiment.

Typically, compounds of this invention that were tested in this assay had a $K_i$ of less than about 100 DM for blockade of carbachol-mediated GTPγ[$^{35}$S] binding. For example, the compound of Example 1 had a $K_i$ of less than about 1 nM.

Test compounds having a lower $K_i$ value in these assays are more effective antagonists for the $hM_2$ muscarinic receptor subtype. Thus, these assays demonstrate that compounds of this invention are potent functional antagonists of the human $M_2$ receptor subtype.

Example 120

In Vivo Rat Bladder Assay

Female Sprague-Dawley rats (Harlan, Indianapolis, Ind.) weighing 200 to 300 g were anesthetized with urethane (1.5 g/kg, s.c., Sigma, St. Louis, Mo.), with a supplement of 0.25 g/kg, s.c. urethane as needed. Urethane was administered at a concentration of 0.25 g/mL.

Rats were prepared for surgery by shaving the neck and abdomen and cleansing with ethanol wipes. First, an incision was made on the ventral surface. An intravenous catheter was placed by isolating and ligating the femoral vein. A small incision was made in the vein proximal to the ligation through which a catheter (micro-Renathane tubing, 0.30 mm ID×0.64 mm OD, Becton Dickinson, Sparks, Md.) filled with D5W was inserted and secured in place with 4.0 silk suture thread (Ethicon, Johnson and Johnson, Somerville, N.J.). Similarly, a catheter was inserted into the femoral artery for the measurement of cardiovascular parameters. A tracheotomy was performed by isolating the trachea and placing a small hole between two tracheal rings. PE 205 tubing (1.57 mm ID×2.08 mm OD, Becton Dickinson, Sparks, Md.) was inserted into the trachea toward the lungs. The neck incision was closed with 9 mm wound clips leaving the catheters and distal end of the trachea tube exposed.

Subsequently, a 3 cm midline sagital incision in the skin and muscle layers of the lower abdomen was made. The bladder and ureters were isolated and exposed by means of tissue forceps. The ureters were ligated and severed distal to the bladder. The bladder was cannulated with PE50 tubing (0.58 mm ID×0.965 mm OD, Becton Dickinson, Sparks, Md.) via the urethra. The cannula was attached to a micro infusion pump to allow infusion of saline into the bladder through a pressure transducer (Argon, Athen, Tex.). The cannula was secured in place using a purse string suture (4.0 silk suture). To ensure a tight seal, the cannula was tied in place around the external urethral orifice with 2.0 silk suture thread. After the bladder was placed back into the peritoneal cavity, the bladder was manually voided allowing the contents to flow out until the bladder was empty. The incision was closed with 9 mm wound clips.

After the surgical preparation, the bladder was filled with saline at a constant rate of 200 μL/min for 5 minutes or until bladder pressure averaged over 30 mm Hg. Subsequently, the bladder was filled with a maintenance infusion of 5 μL/min. When rhythmic volume-induced bladder contractions (VIBC's) were observed, the maintenance infusion was adjusted 2 to 5 μL/min. Only rats demonstrating rhythmic bladder contractions of similar peak height were used in the experiment. Animals not demonstrating this profile within 60 minutes were euthanized by $CO_2$ asphyxiation.

Once stable rhythmic VIBC's were observed for at least 30 minutes during the maintenance infusion, vehicle (D5W) was infused intravenously (1 mL/kg) and changes in VIBC amplitude ($VIBC_{Amp}$) were recorded for 15 minutes. Thereafter, an intravenous dose of the test compound was administered and changes in $VIBC_{Amp}$ were recorded for 15 minutes. Atropine (0.1 mg/kg) was then administered intravenously (1 mL/kg) as a positive control and $VIBC_{Amp}$ and data was recorded for an additional 15 minutes. At least four doses of each test compound at half log increments were tested in this model.

Alternatively, after the vehicle, increasing cumulative intravenous doses of the test compound were administered at 15 minute intervals (1 mL/kg) and changes in $VIBC_{Amp}$ were recorded for 15 minutes. At least 4 doses of test compound were administered at half log increments.

The average $VIBC_{Amp}$ during the 5-15 minute period after test compound and atropine was determined and subtracted from the average $VIBC_{Amp}$ during the 5-15 minute post-vehicle period to obtain the test compound or atropine-induced change in $VIBC_{Amp}$. The inhibitory effects of the test compound were normalized to the atropine response and the resulting dose-response curves were fitted with a four parameter logistic equation to obtain estimates of $ID_{50}$ (dose required to produce 50% of the maximal response).

Test compounds having a lower $ID_{50}$ value in this assay are more effective for reducing peak bladder contraction pressure. In this assay, the compound of Example 1 had an $ID_{50}$ value of less than or equal to about 0.1 mg/kg.

Example 121

In Vivo Rat Salivation Assay

Female Sprague-Dawley rats weighing 200 to 300 g were anesthetized with urethane (1.5 g/kg, s.c., Sigma, St. Louis, Mo.), with a supplement of 0.25 g/kg, s.c. urethane as needed. Urethane was administered at a concentration of 0.25 g/mL.

Rats were placed on a heated blanket on their dorsal side in an inclined position (20° angle) position (head down). A swab was placed in the rat's mouth. The test compound or vehicle was administered intravenously via the tail vein. After 5 min., oxotremorine (1.0 mg/kg) was administered subcutaneously. The swab was discarded and Replaced by a pre-weighed swab. Saliva was then collected for 10 min. and then the swab was removed and re-weighed to determine the output of saliva. Dose-response curves were fitted with a four parameter logistic equation to obtain estimates of $ID_{50}$ (dose required to produce 50% of the maximal response).

Test compounds having a higher $ID_{50}$ in this assay had less of an effect on salivation. In this assay, the compound of Example 1 had an $ID_{50}$ value of greater than or equal to about 0.9 mg/kg.

By comparing the $ID_{50}$ values determined in the rat bladder assay and rat salivation assay, the in vivo bladder/salivation selectivity ratio was calculated for the compounds tested. Surprisingly, compounds of this invention were found to be bladder selective. For example, in this assay, the compound of Example 1 had an $ID_{50}$ bladder/salivation selectivity ratio greater than 20. In contrast, the known muscarinic receptor antagonists oxybutynin and tolterodine had an $ID_{50}$ bladder/salivation selectivity ratio of about 1.4 and 4.8, respectively, in this assay.

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited herein are incorporated by reference herein in their entirety to the same extent as if they had been individually incorporated by reference.

What is claimed is:

1. A compound of formula I:

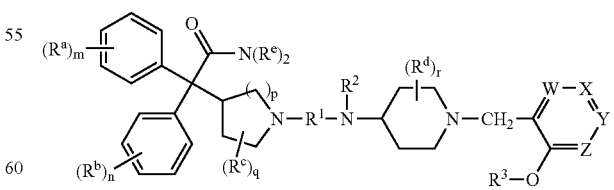

I wherein

W, X, Y and Z are independently selected from the group consisting of CH, $CR^4$, N and N→O; provided that at least one and no more than two of W, X, Y and Z are N or N→O;

$R^1$ is a group of formula (a):

$$—(CH_2)_a—(O)_b—(CH_2)_c— \qquad (a)$$

wherein each —CH$_2$— group in formula (a) and the —CH$_2$— group between the piperidine nitrogen atom and the ring containing W, X, Y and Z in formula I is optionally substituted with 1 or 2 substituents independently selected from the group consisting of $C_{1-2}$ alkyl and fluoro; wherein each alkyl group is optionally substituted with 1 to 3 fluoro substituents;

$R^2$ is selected from the group consisting of hydrogen, $C_{1-6}$ alkyl $C_{2-6}$ alkenyl, $C_{2-6}$ alkynyl, $C_{3-6}$ cycloalkyl, —CH$^2$—R$^5$ and —(CH$_2$)$_x$—R$^6$; wherein each alkyl, alkenyl, alkynyl and cycloalkyl group is optionally substituted with 1 to 5 fluoro substituents;

each $R^3$ is independently selected from the group consisting of hydrogen, $C_{1-6}$ alkyl, $C_{2-6}$ alkenyl, $C_{2-6}$ alkynyl, $C_{3-6}$ cycloalkyl, —CH$_2$—R$^7$ and —(CH$_2$)$_y$—R$^8$; wherein each alkyl, alkenyl, alkynyl and cycloalkyl group is optionally substituted with 1 to 5 fluoro substituents;

each $R^4$ is independently selected from the group consisting of $C_{1-6}$ alkyl $C_{2-6}$ alkenyl, $C_{2-4}$ alkynyl, $C_{3-6}$ cycloalkyl, —OR$^3$ and halo; or two adjacent $R^4$ groups are joined to form $C_{3-6}$ alkylene, —O—($C_{2-4}$ alkylene)-, —O—($C_{1-4}$ alkylene)-O—, —(O)C—CH=CH— or —CH=CH—C(O)—; or when Z is CR$^4$, —OR$^3$ and $R^4$ are joined to form —O—($C_{2-5}$ alkylene)- or —O—($C_{1-5}$ alkylene)-O—; wherein each alkyl, alkylene, alkenyl, alkynyl and cycloalkyl group is optionally substituted with 1 to 5 fluoro substituents;

each $R^5$ and $R^7$ is independently selected from the group consisting of $C_{3-5}$ cycloalkyl, $C_{6-10}$ aryl, —C(O)($C_{6-10}$ aryl), $C_{2-9}$ heteroaryl, —C(O)($C_{2-9}$ heteroaryl) and $C_{3-6}$ heterocyclic; wherein the cycloalkyl group is optionally substituted with 1 to 5 fluoro substituents; and the aryl, heteroaryl and heterocyclic groups are optionally substituted with 1 to 3 substituents independently selected from $R^k$ and the aryl and heteroaryl groups are optionally further substituted with a phenyl group, where the phenyl group is optionally substituted with 1 to 3 substituents independently selected from $R^k$;

each $R^6$ and $R^8$ is independently selected from the group consisting of —OH, —OR$^9$, —SR$^9$, —S(O)R$^9$, —S(O)$_2$ R$^9$, —C(O)R$^9$, $C_{3-5}$ cycloalkyl, $C_{6-10}$ aryl, $C_{2-9}$ heteroaryl and $C_{3-6}$ heterocyclic; wherein the cycloalkyl group is optionally substituted with 1 to 5 fluoro substituents; and the aryl, heteroaryl and heterocyclic groups are optionally substituted with 1 to 3 substituents independently selected from $R^k$;

each $R^9$ is independently selected from the group consisting of $C_{1-4}$ alkyl, $C_{3-5}$ cycloalkyl, $C_{6-10}$ aryl and $C_{2-9}$ heteroaryl; wherein the alkyl and cycloalkyl groups are optionally substituted with 1 to 5 fluoro substituents; and the aryl and heteroaryl groups are optionally substituted with 1 to 3 substituents independently selected from $R^k$;

each $R^a$ and $R^b$ is independently selected from the group consisting of $C_{1-4}$ alkyl, $C_{2-4}$ alkenyl, $C_{2-4}$ alkynyl, $C_{3-6}$ cycloalkyl, cyano, halo, —OR$^f$, —SR$^f$, —S(O)R$^f$, —S(O)$_2$R$_f$ and —NR$^g$R$^h$; or two adjacent $R^a$ groups or two adjacent $R^b$ groups are joined to form $C_{3-6}$ alkylene, —($C_{2-4}$ alkylene)-O— or —O—($C_{1-4}$ alkylene)-O—; wherein each alkyl, alkylene, alkenyl, alkynyl and cycloalkyl group is optionally substituted with 1 to 5 fluoro substituents;

each $R^c$ and $R^d$ is independently selected from the group consisting of $C_{1-4}$ alkyl and fluoro; wherein each alkyl group is optionally substituted with 1 to 5 fluoro substitutents;

each $R^e$ is independently selected from the group consisting of hydrogen, $C_{1-6}$ alkyl, $C_{2-6}$ alkenyl, $C_{2-4}$ alkynyl, $C_{3-6}$ cycloalkyl, $C_{6-10}$ aryl, $C_{2-9}$ heteroaryl, $C_{3-6}$ heterocyclic, —CH$_2$—R$^i$ and —CH$_2$CH$_2$—R$^j$; or both $R^e$ groups are joined together with the nitrogen atom to which they are attached to form $C_{3-6}$ heterocyclic; wherein each alkyl, alkenyl, alkynyl and cycloalkyl group is optionally substituted with 1 to 5 fluoro substitutents; and each aryl, heteroaryl and heterocyclic group is optionally substituted with 1 to 3 substituents independently selected from $R^k$;

each $R^f$ is independently selected from the group consisting hydrogen, $C_{1-4}$ alkyl, $C_{2-4}$ alkenyl, $C_{2-4}$ alkynyl and $C_{3-6}$ cycloalkyl; wherein each alkyl, alkenyl, alkynyl and cycloalkyl group is optionally substituted with 1 to 5 fluoro substitutents;

each $R^g$ and $R^h$ is independently selected from the group consisting of hydrogen, $C_{1-4}$ alkyl, $C_{2-4}$ alkenyl, $C_{2-4}$ alkynyl and $C_{3-6}$ cycloalkyl; or $R^g$ and $R^h$ are joined together with the nitrogen atom to which they are attached to form $C_{3-6}$ heterocyclic; wherein each alkyl, alkenyl, alkynyl and cycloalkyl group is optionally substituted with 1 to 5 fluoro substitutents, and the heterocyclic group is optionally substituted with 1 to 3 substitutents independently selected from $C_{1-4}$ alkyl and fluoro;

each $R^i$ is independently selected from the group consisting of $C_{3-6}$ cycloalkyl, $C_{6-10}$ aryl, $C_{2-9}$ heteroaryl and $C_{3-6}$ heterocyclic; wherein aryl, cycloalkyl, heteroaryl and heterocyclic group is optionally substituted with 1 to 3 substituents independently selected from $R^k$;

each $R^j$ is independently selected from the group consisting of $C_{3-6}$ cycloalkyl, $C_{6-10}$ aryl, $C_{2-9}$ heteroaryl, $C_{3-6}$ heterocyclic, —OH, —O($C_{1-6}$ alkyl), —O($C_{3-6}$ cycloalkyl), —O($C_{6-10}$ aryl), —O($C_{2-9}$ heteroaryl), —S($C_{1-6}$ alkyl), —S(O)($C_{1-6}$ alkyl), —S(O)$_2$($C_{1-6}$ alkyl), —S($C_{3-6}$ cycloalkyl), —S(O)($C_{3-6}$ cycloalkyl), —S(O)$_2$($C_{3-6}$ cycloalkyl), —S($C_{6-10}$ aryl), —S(O)($C_{6-10}$ aryl), —S(O)$_2$($C_{6-10}$ aryl), —S($C_{2-9}$ heteroaryl), —S(O)($C_{2-9}$ heteroaryl) and —S(O)$_2$($C_{2-9}$ heteroaryl); wherein each alkyl group is optionally substituted with 1 to 5 fluoro substituents; and each aryl, cycloalkyl, heteroaryl and heterocyclic group is optionally substituted with 1 to 3 substituents independently selected from $R^k$;

each $R^k$ is independently selected from the group consisting of $C_{1-4}$ alkyl, $C_{2-4}$ alkenyl, $C_{2-4}$ alkynyl, cyano, halo, —OR$^f$, —SR$^f$, —S(O)R$^f$, —S(O)$_2$R$^f$ and —NR$^g$R$^h$; or two adjacent $R^k$ groups are joined to form $C_{3-6}$ alkylene, —($C_{2-4}$ alkylene)-O— or —O—($C_{1-4}$ alkylene)-O—; wherein each alkyl, alkylene, alkenyl and alkynyl group is optionally substituted with 1 to 5 fluoro substitutents;

a is an integer from 2 to 7;

b is 0 or 1;

c is an integer from 2 to 7; provided that a+b+c equals 7, 8 or 9;

m is an integer from 0 to 3;

n is an integer from 0 to 3;

p is 1;

q is an integer from 0 to 4;

r is an integer from 0 to 4;

x is an integer from 2 to 4;
y is an integer from 2 to 4;
or a pharmaceutically-acceptable salt or stereoisomer thereof.

2. The compound according to claim 1, wherein $R^1$ is selected from the group consisting of —(CH$_2$)$_7$—, —(CH$_2$)$_8$—, —(CH$_2$)$_9$—, —(CH$_2$)$_2$—O—(CH$_2$)$_4$—, —(CH$_2$)$_2$—O—(CH$_2$)$_5$—, —(CH$_2$)$_2$—O—(CH$_2$)$_6$—, —(CH$_2$)$_3$—O—(CH$_2$)$_3$—, —(CH$_2$)$_3$—O—(CH$_2$)$_4$—, —(CH$_2$)$_3$—O—(CH$_2$)$_5$—, —(CH$_2$)$_4$—O—(CH$_2$)$_2$—, —(CH$_2$)$_4$—O—(CH$_2$)$_3$—, —(CH$_2$)$_4$—O—(CH$_2$)$_4$—, —(CH$_2$)$_5$—O—(CH$_2$)$_2$—, —(CH$_2$)$_5$—O—(CH$_2$)$_3$— and —(CH$_2$)$_6$—O—(CH$_2$)$_2$—.

3. The compound according to claim 2, wherein $R^1$ is —(CH$_2$)$_7$—, —(CH$_2$)$_8$—, —(CH$_2$)$_9$—, —(CH$_2$)$_3$—O—(CH$_2$)$_3$— or —(CH$_2$)$_4$—O—(CH$_2$)$_4$—.

4. The compound according to claim 3, wherein $R^1$ is —(CH$_2$)$_7$—.

5. The compound according to claim 1, wherein $R^2$ is $C_{1-4}$ alkyl; wherein the alkyl group is optionally substituted with 1 to 3 fluoro substituents.

6. The compound according to claim 5, wherein $R^2$ is selected from the group consisting of methyl, ethyl, n-propyl, isopropyl, n-butyl and isobutyl.

7. The compound according to claim 1, wherein $R^2$ is —CH$_2$—$R^5$.

8. The compound according to claim 7, wherein $R^2$ is selected from the group consisting of:
(a) —CH$_2$—(C$_{3-5}$ cycloalkyl); wherein the cycloalkyl group is optionally substituted with 1 to 3 fluoro substituents;
(b) —CH$_2$-(phenyl), wherein the phenyl group is optionally substituted with 1 to 3 substituents independently selected from $R^k$;
(c) —CH$_2$-(naphthyl); wherein the naphthyl group is optionally substituted with 1 to 3 substituents independently selected from $R^k$;
(d) —CH$_2$-(biphenyl), wherein each phenyl ring of the biphenyl group is optionally substituted with 1 to 3 substituents independently selected from $R^k$;
(e) —CH$_2$-(pyridyl); wherein the pyridyl group is optionally substituted with 1 to 3 substituents independently selected from $R^k$; and
(f) —CH$_2$C(O)-(phenyl), wherein the phenyl ring of the phenacyl group is optionally substituted with 1 to 3 substituents independently selected from $R^k$.

9. The compound according to claim 8, wherein $R^2$ is selected from the group consisting of cyclopropylmethyl, cyclobutylmethyl, cyclopentylmethyl, benzyl, 4-cyanobenzyl, 4-methylbenzyl, 4-trifluoromethoxybenzyl, 4-difluoromethoxybenzyl, 4-thiomethoxybenzyl, 4-methanesulfonylbenzyl, 4-tert-butylbenzyl, 4-phenylbenzyl, pyridyl-2-ylmethyl, pyrid-3-ylmethyl, napthth-2-ylmethyl, 3-cyanophenacyl, and 3,4-ethylenedioxyphenacyl.

10. The compound according to claim 1, wherein $R^2$ is —(CH$_2$)$_x$—$R^6$, wherein x is 2, 3 or 4.

11. The compound according to claim 10, wherein $R^2$ is selected from the group consisting of:
(a) —(CH$_2$)$_x$—OH;
(b) —(CH$_2$)$_x$—O(C$_{1-4}$ alkyl); wherein the alkyl group is optionally substituted with 1 to 3 fluoro substituents;
(c) —(CH$_2$)$_x$—S(C$_{1-4}$ alkyl), —(CH$_2$)$_x$—S(O)(C$_{1-4}$ alkyl), or —(CH$_2$)$_x$—S(O)$_2$(C$_{1-4}$ alkyl); wherein the alkyl group is optionally substituted with 1 to 3 fluoro substituents;

(d) —(CH$_2$)$_x$-(phenyl), wherein the phenyl group is optionally substituted with 1 to 3 substituents independently selected from $R^k$;
(e) —(CH$_2$)$_x$—(O-phenyl), wherein the phenyl group is optionally substituted with 1 to 3 substituents independently selected from $R^k$;
(f) —(CH$_2$)$_x$-(naphthyl), wherein the naphthyl group is optionally substituted with 1 to 3 substituents independently selected from $R^k$; and
(g) —(CH$_2$)$_x$-(indolyl), wherein the indolyl group is optionally substituted with 1 to 3 substituents independently selected from $R^k$.

12. The compound according to claim 11, wherein $R^2$ is selected from the group consisting of 2-hydroxyethyl, 2-methoxyethyl, 2-(methylthio)ethyl, 2-ethoxyethyl, 2-(ethylthio)ethyl, 2-(2,2,2-trifluoroethoxy)ethyl, 2-phenethyl, 2-(naphth-1-yl)ethyl, 2-(indol-3-yl)ethyl, 3-hydroxypropyl, 3-methoxypropyl, 3-ethoxypropyl, 3-phenylpropyl and 3-phenoxypropyl.

13. The compound according to claim 1, wherein $R^2$ is ethyl, n-propyl, isopropyl, cyclopropylmethyl or 2-hydroxyethyl.

14. The compound according to claim 1, wherein each $R^3$ is independently selected from the group consisting of hydrogen, $C_{1-4}$ alkyl, cyclopropylmethyl and 2-hydroxyethyl; wherein each alkyl group is optionally substituted with 1 to 5 fluoro substituents.

15. The compound according to claim 14, wherein each $R^3$ is independently selected from the group consisting of hydrogen, methyl, ethyl, n-propyl, isopropyl, difluoromethyl, trifluoromethyl, 2,2,2-trifluoroethyl, 1,3-difluoroprop-2-yl, 1,1,3,-trifluoroprop-2-yl, and 1,1,3,3-tetrafluoroprop-2-yl.

16. The compound according to claim 1, wherein $R^4$ is selected from the group consisting of $C_{1-4}$ alkyl, —OR$^3$ and halo; wherein the alkyl group is optionally substituted with 1 to 5 fluoro substituents.

17. The compound according to claim 16, wherein $R^4$ is methyl, —OR$^3$, fluoro or chloro.

18. The compound according to claim 1, wherein W, X, Y and Z are defined as follows:
(a) W is N; X is CH; Y is CH; and Z is CH;
(b) W is CH or CR$^4$; X is N; Y is CH and Z is CH;
(c) W is CH or CR$^4$; X is CH; Y is N; and Z is CH;
(d) W is CH or CR$^4$; X is CH; Y is CH; and Z is N; or
(e) W is CH; X is N; Y is CH and Z is CH.

19. The compound according to claim 18, wherein W is CH; X is N; Y is CH and Z is CH.

20. A compound of formula II:

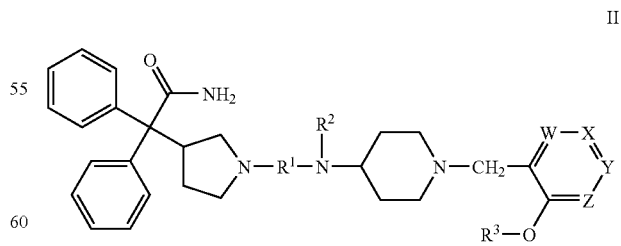

wherein
W, X, Y and Z are independently selected from the group consisting of CH, CR$^4$, N and N→O; provided that at least one and no more than two of W, X, Y and Z are N or N→O;

R¹ is a group of formula (a):

—(CH₂)ₐ—(O)ᵦ—(CH₂)ᵢ—  (a)

wherein each —CH₂— group in formula (a) and the —CH₂— group between the piperidine nitrogen atom and the ring containing W, X, Y and Z in formula II is optionally substituted with 1 or 2 substituents independently selected from the group consisting of $C_{1-2}$ allyl and fluoro; wherein each alkyl group is optionally substituted with 1 to 3 fluoro substitutents;

R² is selected from the group consisting of hydrogen, $C_{1-6}$ alkyl, $C_2$-alkenyl, $C_{2-6}$ alkynyl, $C_{3-6}$ cycloalkyl, —CH₂—R⁵ and —(CH₂)ₓ—R⁶; wherein each alkyl, alkenyl, alkynyl and cycloalkyl group is optionally substituted with 1 to 5 fluoro substitutents;

each R³ is independently selected from the group consisting of hydrogen, $C_{1-6}$ alkyl, $C_{2-6}$-alkenyl, $C_{2-6}$ alkynyl, $C_{3-6}$ cycloalkyl, —CH₂—R⁷ and —(CH₂)ᵧ—R⁸; wherein each alkyl, alkenyl, alkynyl and cycloalkyl group is optionally substituted with 1 to 5 fluoro substitutents;

each R⁴ is independently selected from the group consisting of $C_{1-6}$ alkyl, $C_{2-6}$ alkenyl, $C_{2-6}$ alkynyl, $C_{3-6}$ cycloalkyl, —OR³ and halo; or two adjacent R⁴ groups are joined to form $C_{3-6}$ alkylene, —O—($C_{2-4}$ alkylene)-, —O—($C_{1-4}$ alkylene)-O—, —(O)C—CH=CH— or —CH=CH—C(O)—; or when Z is CR⁴, —OR³ and R⁴ are joined to form —O—($C_{2-5}$ alkylene)- or —O—($C_{1-5}$ alkylene)-O—; wherein each alkyl, alkylene, alkenyl, alkynyl and cycloalkyl group is optionally substituted with 1 to 5 fluoro substitutents;

each R⁵ and R⁷ is independently selected from the group consisting of $C_{3-5}$ cycloalkyl, $C_{6-10}$ aryl, —C(O)($C_{6-10}$ aryl), $C_{2-9}$ heteroaryl, —C(O)($C_{2-9}$ heteroaryl) and $C_{3-6}$ heterocyclic; wherein the cycloalkyl group is optionally substituted with 1 to 5 fluoro substitutents; and the aryl, heteroaryl and heterocyclic groups are optionally substituted with 1 to 3 substituents independently selected from Rᵏ and the aryl and heteroaryl groups are optionally further substituted with a phenyl group, where the phenyl group is optionally substituted with 1 to 3 substituents independently selected from Rᵏ;

each R⁶ and R⁸ is independently selected from the group consisting of —OH, —OR⁹, —SR⁹, —S(O)R⁹, —S(O)₂ R⁹, —C(O)R⁹, $C_{3-5}$ cycloalkyl, $C_{6-10}$ aryl, $C_{2-9}$ heteroaryl and $C_{3-6}$ heterocyclic; wherein the cycloalkyl group is optionally substituted with 1 to 5 fluoro substitutents; and the aryl, heteroaryl and heterocyclic groups are optionally substituted with 1 to 3 substituents independently selected from Rᵏ;

each R⁹ is independently selected from the group consisting of $C_{1-4}$ alkyl, $C_{3-5}$ cycloalkyl, $C_{6-10}$ aryl and $C_{2-9}$ heteroaryl; wherein the alkyl and cycloalkyl groups are optionally substituted with 1 to 5 fluoro substitutents; and the aryl and heteroaryl groups are optionally substituted with 1 to 3 substituents independently selected from Rᵏ;

each Rᶠ is independently selected from the group consisting hydrogen, $C_{1-4}$ alkyl, $C_{2-4}$ alkenyl, $C_{2-4}$ alkyl and $C_{3-6}$ cycloalkyl; wherein each alkyl, alkenyl, alkynyl and cycloalkyl group is optionally substituted with 1 to 5 fluoro substitutents;

each Rᵍ and Rʰ is independently selected from the group consisting of hydrogen, $C_{1-4}$ alkyl, $C_{2-4}$ alkenyl, $C_{2-4}$ alkynyl and $C_{3-6}$ cycloalkyl; or Rᵍ and Rʰ are joined together with the nitrogen atom to which they are attached to form $C_{3-6}$ heterocyclic; wherein each alkyl, alkenyl, alkynyl and cycloalkyl group is optionally substituted with 1 to 5 fluoro substitutents, and the heterocyclic group is optionally substituted with 1 to 3 substitutents independently selected from $C_{1-4}$ alkyl and fluoro;

each Rᵏ is independently selected from the group consisting of $C_{1-4}$ alkyl, $C_{2-4}$ alkenyl, $C_{2-4}$ alkynyl, cyano, halo, —ORᶠ, —SRᶠ, —S(O)Rᶠ, —S(O)₂Rᶠ and —NRᵍRʰ; or two adjacent Rᵏ groups are joined to form $C_{3-6}$ alkylene, —($C_{2-4}$ alkylene)-O— or —O—($C_{1-4}$ alkylene)-O—; wherein each alkyl, alkylene, alkenyl and alkynyl group is optionally substituted with 1 to 5 fluoro substitutents;

a is an integer from 2 to 7;
b is 0 or 1;
c is an integer from 2 to 7; provided that a+b+c equals 7, 8 or 9;
x is an integer from 2 to 4;
y is an integer from 2 to 4;
or a pharmaceutically-acceptable salt or stereoisomer thereof.

21. The compound according to claim 20, wherein R¹ is —(CH₂)₇—, —(CH₂)₈—, —(CH₂)₉—, —(CH₂)₃—O—(CH₂)₃— or —(CH₂)₄—O—(CH₂)₄—.

22. The compound according to claim 21, wherein R² is $C_{1-4}$ alkyl; wherein the alkyl group is optionally substituted with 1 to 3 fluoro substitutents.

23. The compound according to claim 22, wherein each R³ is independently selected from the group consisting of hydrogen, $C_{1-4}$ alkyl, cyclopropylmethyl and 2-hydroxyethyl; wherein each alkyl group is optionally substituted with 1 to 5 fluoro substitutents.

24. The compound according to claim 23, wherein
R¹ is —(CH₂)₇—;
R² is selected from the group consisting of methyl, ethyl, n-propyl, isopropyl, n-butyl and isobutyl; and
each R³ is independently selected from the group consisting of hydrogen, methyl, ethyl, n-propyl, isopropyl, difluoromethyl, trifluoromethyl, 2,2,2-trifluoroethyl, 1,3-difluoroprop-2-yl, 1,1,3,-trifluoroprop-2-yl, and 1,1,3,3-tetrafluoroprop-2-yl.

25. A compound of formula III:

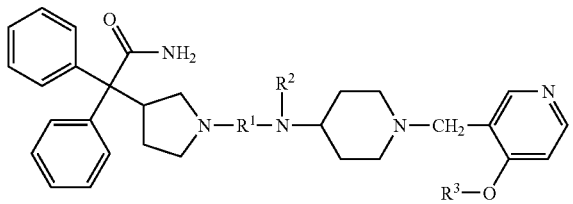

wherein
R¹ is a group of formula (a):

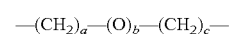

—(CH₂)ₐ—(O)ᵦ—(CH₂)ᵢ—  (a)

wherein each —CH₂— group in formula (a) and the —CH₂— group between the piperidine nitrogen atom and the pyridine ring in formula III is optionally substituted with 1 or 2 substituents independently selected from the group consisting of $C_{1-2}$ alkyl and fluoro; wherein each alkyl group is optionally substituted with 1 to 3 fluoro substitutents;

R² is selected from the group consisting of hydrogen, C₁₋₆ alkyl, C₂₋₆ alkenyl, C₂₋₆ alkynyl, C₃₋₆ cycloalkyl, —CH²—R⁵ and —(CH₂)ₓ—R⁶; wherein each alkyl, alkenyl, alkynyl and cycloalkyl group is optionally substituted with 1 to 5 fluoro substituents;

each R³ is independently selected from the group consisting of hydrogen, C₁₋₆ alkyl, C₂₋₆ alkenyl, C₂₋₆ alkynyl, C₃₋₆ cycloalkyl, —CH₂—R⁷ and —(CH₂)ᵧ—R⁸; wherein each alkyl, alkenyl, alkynyl and cycloalkyl group is optionally substituted with 1 to 5 fluoro substitutents;

each R⁵ and R⁷ is independently selected from the group consisting of C₃₋₅ cycloalkyl, C₆₋₁₀ aryl, —C(O)(C₆₋₁₀ aryl), C₂₋₉ heteroaryl, —C(O)(C₂₋₉ heteroaryl) and C₃₋₆ heterocyclic; wherein the cycloalkyl group is optionally substituted with 1 to 5 fluoro substituents; and the aryl, heteroaryl and heterocyclic groups are optionally substituted with 1 to 3 substituents independently selected from Rᵏ and the aryl and heteroaryl groups are optionally further substituted with a phenyl group, where the phenyl group is optionally substituted with 1 to 3 substituents independently selected from Rᵏ;

each R⁶ and R⁸ is independently selected from the group consisting of —OH, —OR⁹, —SR⁹, —S(O)R⁹, —S(O)₂ R⁹, —C(O)R⁹, C₃₋₅ cycloalkyl, C₆₋₁₀ aryl, C₂₋₉ heteroaryl and C₃₋₆ heterocyclic; wherein the cycloalkyl group is optionally substituted with 1 to 5 fluoro substituents; and the aryl, heteroaryl and heterocyclic groups are optionally substituted with 1 to 3 substituents independently selected from Rᵏ;

each R⁹ is independently selected from the group consisting of C₁₋₄ alkyl, C₃₋₅ cycloalkyl, C₆₋₁₀ aryl and C₂₋₉ heteroaryl; wherein the alkyl and cycloalkyl groups are optionally substituted with 1 to 5 fluoro substituents; and the aryl and heteroaryl groups are optionally substituted with 1 to 3 substituents independently selected from Rᵏ;

each Rᶠ is independently selected from the group consisting hydrogen, C₁₋₄ alkyl, C₂₋₄ alkenyl, C₂₋₄ alkynyl and C₃₋₆ cycloalkyl; wherein each alkyl, alkenyl, alkynyl and cycloalkyl group is optionally substituted with 1 to 5 fluoro substitutents;

each Rᵍ and Rʰ is independently selected from the group consisting of hydrogen, C₁₋₄ alkyl, C₂₋₄ alkenyl, C₂₋₄ alkynyl and C₃₋₆ cycloalkyl; or Rᵍ and Rʰ are joined together with the nitrogen atom to which they are attached to form C₃₋₆ heterocyclic; wherein each alkyl, alkenyl, alkynyl and cycloalkyl group is optionally substituted with 1 to 5 fluoro substituents, and the heterocyclic group is optionally substituted with 1 to 3 substitutents independently selected from C₁₋₄ alkyl and fluoro;

each Rᵏ is independently selected from the group consisting of C₁₋₄ alkyl, C₂₋₄ alkenyl, C₂₋₄ alkynyl, cyano, halo, —ORᶠ, —SRᶠ, —S(O)Rᶠ, —S(O)₂Rᶠ and —NRᵍRʰ; or two adjacent Rᵏ groups are joined to form C₃₋₆ alkylene, —(C₂₋₄ alkylene)-O— or —O—(C₁₋₄ alkylene)-O—; wherein each alkyl, alkylene, alkenyl and alkynyl group is optionally substituted with 1 to 5 fluoro substitutents;

a is an integer from 2 to 7;
b is 0 or 1;
c is an integer from 2 to 7; provided that a+b+c equals 7, 8 or 9;
x is an integer from 2 to 4;
y is an integer from 2 to 4;

or a pharmaceutically-acceptable salt or stereoisomer thereof.

26. The compound according to claim 25, wherein R¹ is —(CH₂)₇—, —(CH₂)₈—, —(CH₂)₉—, —(CH₂)₃—O—(CH₂)₃— or —(CH₂)₄—O—(CH₂)₄—.

27. The compound according to claim 26, wherein R² is C₁₋₄ alkyl; wherein the alkyl group is optionally substituted with 1 to 3 fluoro substituents.

28. The compound according to claim 27, wherein each R³ is independently selected from the group consisting of hydrogen, C₁₋₄ alkyl, cyclopropylmethyl and 2-hydroxyethyl; wherein each alkyl group is optionally substituted with 1 to 5 fluoro substituents.

29. The compound according to claim 28, wherein
R¹ is —(CH₂)₇—;
R² is selected from the group consisting of methyl, ethyl, n-propyl, isopropyl, n-butyl and isobutyl; and
R³ is selected from the group consisting of hydrogen, methyl, ethyl, n-propyl, isopropyl, difluoromethyl, trifluoromethyl, 2,2,2-trifluoroethyl, 1,3-difluoroprop-2-yl, 1,1,3,-trifluoroprop-2-yl, and 1,1,3,3-tetrafluoroprop-2-yl.

30. A compound selected from the group consisting of:
4-{N-[7-(3-(S)-1-carbamoyl-1,1-diphenylmethyl)pyrrolidin-1-yl)hept-1-yl]-N-(isopropyl)amino}-1-(4-methoxypyrid-3-ylmethyl)piperidine;
4-{N-[7-(3-(S)-1-carbamoyl-1,1-diphenylmethyl)pyrrolidin-1-yl)-4-oxahept-1-yl]-N-(isopropyl)amino}-1-(4-methoxypyrid-3-ylmethyl)piperidine;
4-{N-[7-(3-(S)-1-carbamoyl-1,1-diphenylmethyl)pyrrolidin-1-yl)-3-oxahept-1-yl]-N-(isopropyl)amino}-1-(4-methoxypyrid-3-ylmethyl)piperidine;
4-{N-[7-(3-(S)-1-carbamoyl-1,1-diphenylmethyl)pyrrolidin-1-yl)hept-1-yl]-N-(ethyl)amino}-1-(2-methoxypyrid-3-ylmethyl)piperidine;
4-{N-[7-(3-(S)-1-carbamoyl-1,1-diphenylmethyl)pyrrolidin-1-yl)hept-1-yl]-N-(ethyl)amino}-1-(3-methoxypyrid-2-ylmethyl)piperidine;
4-{N-[7-(3-(S)-1-carbamoyl-1,1-diphenylmethyl)pyrrolidin-1-yl)hept-1-yl]-N-(ethyl)amino}-1-(4-methoxypyrid-3-ylmethyl)piperidine;
4-{N-[7-(3-(S)-1-carbamoyl-1,1-diphenylmethyl)pyrrolidin-1-yl)-4-oxahept-1-yl]-N-(ethyl)amino}-1-(4-methoxypyrid-3-ylmethyl)piperidine;
4-{N-[8-(3-(S)-1-carbamoyl-1,1-diphenylmethyl)pyrrolidin-1-yl)oct-1-yl]-N-(ethyl)amino}-1-(4-methoxypyrid-3-ylmethyl)piperidine;
4-{N-[9-(3-(S)-1-carbamoyl-1,1-diphenylmethyl)pyrrolidin-1-yl)non-1-yl]-N-(ethyl)amino}-1-(4-methoxypyrid-3-ylmethyl)piperidine;
4-{N-[7-(3-(S)-1-carbamoyl-1,1-diphenylmethyl)pyrrolidin-1-yl)-3-oxahept-1-yl]-N-(ethyl)amino}-1-(4-methoxypyrid-3-ylmethyl)piperidine;
4-{N-[8-(3-(S)-1-carbamoyl-1,1-diphenylmethyl)pyrrolidin-1-yl)-3-oxaoct-1-yl]-N-(ethyl)amino}-1-(4-methoxypyrid-3-ylmethyl)piperidine;
4-{N-[9-(3-(S)-1-carbamoyl-1,1-diphenylmethyl)pyrrolidin-1-yl)-3-oxanon-1-yl]-N-(ethyl)amino}-1-(4-methoxypyrid-3-ylmethyl)piperidine;
4-{N-[8-(3-(S)-1-carbamoyl-1,1-diphenylmethyl)pyrrolidin-1-yl)-4-oxaoct-1-yl]-N-(ethyl)amino}-1-(4-methoxypyrid-3-ylmethyl)piperidine;
4-{N-[9-(3-(S)-1-carbamoyl-1,1-diphenylmethyl)pyrrolidin-1-yl)-4-oxanon-1-yl]-N-(ethyl)amino}-1-(4-methoxypyrid-3-ylmethyl)piperidine;

4-{N-[7-(3-(S)-1-carbamoyl-1,1-diphenylmethyl)pyrrolidin-1-yl)-5-oxahept-1-yl]-N-(ethyl)amino}-1-(4-methoxypyrid-3-ylmethyl)piperidine;

4-{N-[8-(3-(S)-1-carbamoyl-1,1-diphenylmethyl)pyrrolidin-1-yl)-5-oxaoct-1-yl]-N-(ethyl)amino}-1-(4-methoxypyrid-3-ylmethyl)piperidine;

4-{N-[9-(3-(S)-1-carbamoyl-1,1-diphenylmethyl)pyrrolidin-1-yl)-5-oxanon-1-yl]-N-(ethyl)amino}-1-(4-methoxypyrid-3-ylmethyl)piperidine;

4-{N-[8-(3-(S)-1-carbamoyl-1,1-diphenylmethyl)pyrrolidin-1-yl)-6-oxaoct-1-yl]-N-(ethyl)amino}-1-(4-methoxypyrid-3-ylmethyl)piperidine;

4-{N-[9-(3-(S)-1-carbamoyl-1,1-diphenylmethyl)pyrrolidin-1-yl)-6-oxanon-1-yl]-N-(ethyl)amino}-1-(4-methoxypyrid-3-ylmethyl)piperidine;

4-{N-[9-(3-(S)-1-carbamoyl-1,1-diphenylmethyl)pyrrolidin-1-yl)-7-oxanon-1-yl]-N-(ethyl)amino}-1-(4-methoxypyrid-3-ylmethyl)piperidine;

4-{N-[7-(3-(S)-1-carbamoyl-1,1-diphenylmethyl)pyrrolidin-1-yl)hep-1-yl]-N-(prop-1-yl)amino}-1-(4-methoxypyrid-3-ylmethyl)piperidine;

4-{N-[8-(3-(S)-1-carbamoyl-1,1-diphenylmethyl)pyrrolidin-1-yl)oct-1-yl]-N-(prop-1-yl)amino}-1-(4-methoxypyrid-3-ylmethyl)piperidine;

4-{N-[9-(3-(S)-1-carbamoyl-1,1-diphenylmethyl)pyrrolidin-1-yl)non-1-yl]-N-(prop-1-yl)amino}-1-(4-methoxypyrid-3-ylmethyl)piperidine;

4-{N-[7-(3-(S)-1-carbamoyl-1,1-diphenylmethyl)pyrrolidin-1-yl)-3-oxahept-1-yl]-N-(prop-1-yl)amino}-1-(4-methoxypyrid-3-ylmethyl)piperidine;

4-{N-[8-(3-(S)-1-carbamoyl-1,1-diphenylmethyl)pyrrolidin-1-yl)-3-oxaoct-1-yl]-N-(prop-1-yl)amino}-1-(4-methoxypyrid-3-ylmethyl)piperidine;

4-{N-[9-(3-(S)-1-carbamoyl-1,1-diphenylmethyl)pyrrolidin-1-yl)-3-oxanon-1-yl]-N-(prop-1-yl)amino}-1-(4-methoxypyrid-3-ylmethyl)piperidine;

4-{N-[7-(3-(S)-1-carbamoyl-1,1-diphenylmethyl)pyrrolidin-1-yl)-4-oxahept-1-yl]-N-(prop-1-yl)amino}-1-(4-methoxypyrid-3-ylmethyl)piperidine;

4-{N-[8-(3-(S)-1-carbamoyl-1,1-diphenylmethyl)pyrrolidin-1-yl)-4-oxaoct-1-yl]-N-(prop-1-yl)amino}-1-(4-methoxypyrid-3-ylmethyl)piperidine;

4-{N-[9-(3-(S)-1-carbamoyl-1,1-diphenylmethyl)pyrrolidin-1-yl)-4-oxanon-1-yl]-N-(prop-1-yl)amino}-1-(4-methoxypyrid-3-ylmethyl)piperidine;

4-{N-[7-(3-(S)-1-carbamoyl-1,1-diphenylmethyl)pyrrolidin-1-yl)-5-oxahept-1-yl]-N-(prop-1-yl)amino}-1-(4-methoxypyrid-3-ylmethyl)piperidine;

4-{N-[8-(3-(S)-1-carbamoyl-1,1-diphenylmethyl)pyrrolidin-1-yl)-5-oxaoct-1-yl]-N-(prop-1-yl)amino}-1-(4-methoxypyrid-3-ylmethyl)piperidine;

4-{N-[9-(3-(S)-1-carbamoyl-1,1-diphenylmethyl)pyrrolidin-1-yl)-5-oxanon-1-yl]-N-(prop-1-yl)amino}-1-(4-methoxypyrid-3-ylmethyl)piperidine;

4-{N-[8-(3-(S)-1-carbamoyl-1,1-diphenylmethyl)pyrrolidin-1-yl)-6-oxaoct-1-yl]-N-(prop-1-yl)amino}-1-(4-methoxypyrid-3-ylmethyl)piperidine;

4-{N-[9-(3-(S)-1-carbamoyl-1,1-diphenylmethyl)pyrrolidin-1-yl)-6-oxanon-1-yl]-N-(prop-1-yl)amino}-1-(4-methoxypyrid-3-ylmethyl)piperidine;

4-{N-[9-(3-(S)-1-carbamoyl-1,1-diphenylmethyl)pyrrolidin-1-yl)-7-oxanon-1-yl]-N-(prop-1-yl)amino}-1-(4-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-n-propoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-isopropoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-cyclopropyl-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-{4-(2-hydroxyethoxy)pyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-isobutoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2,4-dimethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino)}-1-(2-fluoro-4-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2-chloro-4-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2-methyl-4-methoxypyrid-3-ylmethyl)piperidine;

4-{N-[8-(3-(S)-1-carbamoyl-1,1-diphenylmethyl)pyrrolidin-1-yl)oct-1-yl]-N-(isopropyl)amino}-1-(4-methoxypyrid-3-ylmethyl)piperidine;

4-{N-[9-(3-(S)-1-carbamoyl-1,1-diphenylmethyl)pyrrolidin-1-yl)non-1-yl]-N-(isopropyl)amino}-1-(4-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(3-methoxypyrid-2-ylmethyl)piperidine;

4-{N-[8-(3-(S)-1-carbamoyl-1,1-diphenylmethyl)pyrrolidin-1-yl)oct-1-yl]-N-(isopropyl)amino}-1-(3-methoxypyrid-2-ylmethyl)piperidine;

4-{N-[9-(3-(S)-1-carbamoyl-1,1-diphenylmethyl)pyrrolidin-1-yl)non-1-yl]-N-(isopropyl)amino}-1-(3-methoxypyrid-2-ylmethyl)piperidine;

4-{N-[7-(3-(S)-1-carbamoyl-1,1-diphenylmethyl)pyrrolidin-1-yl)hep-1-yl]-N-(isopropyl)amino}-1-(3-methoxypyrid-4-ylmethyl)piperidine;

4-{N-[8-(3-(S)-1-carbamoyl-1,1-diphenylmethyl)pyrrolidin-1-yl)oct-1-yl]-N-(isopropyl)amino}-1-(3-methoxypyrid-4-ylmethyl)piperidine;

4-{N-[9-(3-(S)-1-carbamoyl-1,1-diphenylmethyl)pyrrolidin-1-yl)non-1-yl]-N-(isopropyl)amino}-1-(3-methoxypyrid-4-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2-methoxypyrid-3-ylmethyl)piperidine;

4-{N-[8-(3-(S)-1-carbamoyl-1,1-diphenylmethyl)pyrrolidin-1-yl)oct-1-yl]-N-(isopropyl)amino}-1-(2-methoxypyrid-3-ylmethyl)piperidine;

4-{N-[9-(3-(S)-1-carbamoyl-1,1-diphenylmethyl)pyrrolidin-1-yl)non-1-yl]-N-(isopropyl)amino}-1-(2-methoxypyrid-3-ylmethyl)piperidine;

4-{N-[7-(3-(S)-1-carbamoyl-1,1-diphenylmethyl)pyrrolidin-1-yl)-3-oxahept-1-yl]-N-(isopropyl)amino}-1-(4-methoxypyrid-3-ylmethyl)piperidine;

4-{N-[8-(3-(S)-1-carbamoyl-1,1-diphenylmethyl)pyrrolidin-1-yl)-3-oxaoct-1-yl]-N-(isopropyl)amino}-1-(4-methoxypyrid-3-ylmethyl)piperidine;

4-{N-[9-(3-(S)-1-carbamoyl-1,1-diphenylmethyl)pyrrolidin-1-yl)-3-oxanon-1-yl]-N-(isopropyl)amino}-1-(4-methoxypyrid-3-ylmethyl)piperidine;

4-{N-[7-(3-(S)-1-carbamoyl-1,1-diphenylmethyl)pyrrolidin-1-yl)-4-oxahep-1-yl]-N-(isopropyl)amino}-1-(4-methoxypyrid-3-ylmethyl)piperidine;

4-{N-[9-(3-(S)-1-carbamoyl-1,1-diphenylmethyl)pyrrolidin-1-yl)-4-oxanon-1-yl]-N-(isopropyl)amino}-1-(4-methoxypyrid-3-ylmethyl)piperidine;

4-{N-[8-(3-(S)-1-carbamoyl-1,1-diphenylmethyl)pyrrolidin-1-yl)-5-oxaoct-1-yl]-N-(isopropyl)amino}-1-(4-methoxypyrid-3-ylmethyl)piperidine;

4-{N-[9-(3-(S)-1-carbamoyl-1,1-diphenylmethyl)pyrrolidin-1-yl)-5-oxanon-1-yl]-N-(isopropyl)amino}-1-(4-methoxypyrid-3-ylmethyl)piperidine;

4-{N-[8-(3-(S)-1-carbamoyl-1,1-diphenylmethyl)pyrrolidin-1-yl)-6-oxaoct-1-yl]-N-(isopropyl)amino}-1-(4-methoxypyrid-3-ylmethyl)piperidine;

4-{N-[9-(3-(S)-1-carbamoyl-1,1-diphenylmethyl)pyrrolidin-1-yl)-6-oxanon-1-yl]-N-(isopropyl)amino}-1-(4-methoxypyrid-3-ylmethyl)piperidine;

4-{N-[9-(3-(S)-1-carbamoyl-1,1-diphenylmethyl)pyrrolidin-1-yl)-7-oxanon-1-yl]-N-(isopropyl)amino}-1-(4-methoxypyrid-3-ylmethyl)piperidine;

4-{N-[7-(3-(S)-1-carbamoyl-1,1-diphenylmethyl)pyrrolidin-1-yl)hep-1-yl]-N-(cyclopropylmethyl)amino}-1-(4-methoxypyrid-3-ylmethyl)piperidine;

4-{N-[8-(3-(S)-1-carbamoyl-1,1-diphenylmethyl)pyrrolidin-1-yl)oct-1-yl]-N-(cyclopropylmethyl)amino}-1-(4-methoxypyrid-3-ylmethyl)piperidine;

4-{N-[9-(3-(S)-1-carbamoyl-1,1-diphenylmethyl)pyrrolidin-1-yl)non-1-yl]-N-(cyclopropylmethyl)amino}-1-(4-methoxypyrid-3-ylmethyl)piperidine;

4-{N-[7-(3-(S)-1-carbamoyl-1,1-diphenylmethyl)pyrrolidin-1-yl)-3-oxahept-1-yl]-N-(cyclopropylmethyl)amino}-1-(4-methoxypyrid-3-ylmethyl)piperidine;

4-{N-[8-(3-(S)-1-carbamoyl-1,1-diphenylmethyl)pyrrolidin-1-yl)-3-oxaoct-1-yl]-N-(cyclopropylmethyl)amino}-1-(4-methoxypyrid-3-ylmethyl)piperidine;

4-{N-[9-(3-(S)-1-carbamoyl-1,1-diphenylmethyl)pyrrolidin-1-yl)-3-oxanon-1-yl]-N-(cyclopropylmethyl)amino}-1-(4-methoxypyrid-3-ylmethyl)piperidine;

4-{N-[7-(3-(S)-1-carbamoyl-1,1-diphenylmethyl)pyrrolidin-1-yl)-4-oxahep-1-yl]-N-(cyclopropylmethyl)amino}-1-(4-methoxypyrid-3-ylmethyl)piperidine;

4-{N-[8-(3-(S)-1-carbamoyl-1,1-diphenylmethyl)pyrrolidin-1-yl)-4-oxaoct-1-yl]-N-(cyclopropylmethyl)amino}-1-(4-methoxypyrid-3-ylmethyl)piperidine;

4-{N-[9-(3-(S)-1-carbamoyl-1,1-diphenylmethyl)pyrrolidin-1-yl)-4-oxanon-1-yl]-N-(cyclopropylmethyl)amino}-1-(4-methoxypyrid-3-ylmethyl)piperidine;

4-{N-[7-(3-(S)-1-carbamoyl-1,1-diphenylmethyl)pyrrolidin-1-yl)-5-oxahept-1-yl]-N-(cyclopropylmethyl)amino}-1-(4-methoxypyrid-3-ylmethyl)piperidine;

4-{N-[8-(3-(S)-1-carbamoyl-1,1-diphenylmethyl)pyrrolidin-1-yl)-5-oxaoct-1-yl]-N-(cyclopropylmethyl)amino}-1-(4-methoxypyrid-3-ylmethyl)piperidine;

4-{N-[9-(3-(S)-1-carbamoyl-1,1-diphenylmethyl)pyrrolidin-1-yl)-5-oxanon-1-yl]-N-(cyclopropylmethyl)amino}-1-(4-methoxypyrid-3-ylmethyl)piperidine;

4-{N-[8-(3-(S)-1-carbamoyl-1,1-diphenylmethyl)pyrrolidin-1-yl)-6-oxaoct-1-yl]-N-(cyclopropylmethyl)amino)}-1-(4-methoxypyrid-3-ylmethyl)piperidine;

4-{N-[9-(3-(S)-1-carbamoyl-1,1-diphenylmethyl)pyrrolidin-1-yl)-6-oxanon-1-yl]-N-(cyclopropylmethyl)amino}-1-(4-methoxypyrid-3-ylmethyl)piperidine;

4-{N-[9-(3-(S)-1-carbamoyl-1,1-diphenylmethyl)pyrrolidin-1-yl)-7-oxanon-1-yl]-N-(cyclopropylmethyl)amino}-1-(4-methoxypyrid-3-ylmethyl)piperidine;

4-{N-[7-(3-(S)-1-carbamoyl-1,1-diphenylmethyl)pyrrolidin-1-yl)hep-1-yl]-N-(2-hydroxyethyl)amino}-1-(4-methoxypyrid-3-ylmethyl)piperidine;

4-{N-[8-(3-(S)-1-carbamoyl-1,1-diphenylmethyl)pyrrolidin-1-yl)oct-1-yl]-N-(2-hydroxyethyl)amino}-1-(4-methoxypyrid-3-ylmethyl)piperidine;

4-{N-[9-(3-(S)-1-carbamoyl-1,1-diphenylmethyl)pyrrolidin-1-yl)non-1-yl]-N-(2-hydroxyethyl)amino}-1-(4-methoxypyrid-3-ylmethyl)piperidine;

4-{N-[7-(3-(S)-1-carbamoyl-1,1-diphenylmethyl)pyrrolidin-1-yl)-3-oxahept-1-yl]-N-(2-hydroxyethyl)amino}-1-(4-methoxypyrid-3-ylmethyl)piperidine;

4-{N-[8-(3-(S)-1-carbamoyl-1,1-diphenylmethyl)pyrrolidin-1-yl)-3-oxaoct-1-yl]-N-(2-hydroxyethyl)amino}-1-(4-methoxypyrid-3-ylmethyl)piperidine;

4-{N-[9-(3-(S)-1-carbamoyl-1,1-diphenylmethyl)pyrrolidin-1-yl)-3-oxanon-1-yl]-N-(2-hydroxyethyl)amino}-1-(4-methoxypyrid-3-ylmethyl)piperidine;

4-{N-[7-(3-(S)-1-carbamoyl-1,1-diphenylmethyl)pyrrolidin-1-yl)-4-oxahep-1-yl]-N-(2-hydroxyethyl)amino}-1-(4-methoxypyrid-3-ylmethyl)piperidine;

4-{N-[8-(3-(S)-1-carbamoyl-1,1-diphenylmethyl)pyrrolidin-1-yl)-4-oxaoct-1-yl]-N-(2-hydroxyethyl)amino}-1-(4-methoxypyrid-3-ylmethyl)piperidine;

4-{N-[9-(3-(S)-1-carbamoyl-1,1-diphenylmethyl)pyrrolidin-1-yl)-4-oxanon-1-yl]-N-(2-hydroxyethyl)amino}-1-(4-methoxypyrid-3-ylmethyl)piperidine;

4-{N-[7-(3-(S)-1-carbamoyl-1,1-diphenylmethyl)pyrrolidin-1-yl)-5-oxahept-1-yl]-N-(2-hydroxyethyl)amino}-1-(4-methoxypyrid-3-ylmethyl)piperidine;

4-{N-[8-(3-(S)-1-carbamoyl-1,1-diphenylmethyl)pyrrolidin-1-yl)-5-oxaoct-1-yl]-N-(2-hydroxyethyl)amino}-1-(4-methoxypyrid-3-ylmethyl)piperidine;

4-{N-[9-(3-(S)-1-carbamoyl-1,1-diphenylmethyl)pyrrolidin-1-yl)-5-oxanon-1-yl]-N-(2-hydroxyethyl)amino}-1-(4-methoxypyrid-3-ylmethyl)piperidine;

4-{N-[8-(3-(S)-1-carbamoyl-1,1-diphenylmethyl)pyrrolidin-1-yl)-6-oxaoct-1-yl]-N-(2-hydroxyethyl)amino}-1-(4-methoxypyrid-3-ylmethyl)piperidine;

4-{N-[9-(3-(S)-1-carbamoyl-1,1-diphenylmethyl)pyrrolidin-1-yl)-6-oxanon-1-yl]-N-(2-hydroxyethyl)amino}-1-(4-methoxypyrid-3-ylmethyl)piperidine;

4-{N-[9-(3-(S)-1-carbamoyl-1,1-diphenylmethyl)pyrrolidin-1-yl)-7-oxanon-1-yl]-N-(2-hydroxyethyl)amino}-1-(4-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-tert-butoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-hydroxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-ethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-trifluoromethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-difluoromethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-methoxy-2-trifluoromethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2-difluoromethoxy-4-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2-methoxy-4-trifluoromethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(4-difluoromethoxy-2-methoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-{2,4-di(trifluoromethoxy)pyrid-3-ylmethyl}piperidine;

4-{N-[7-(3-(S)-1-carbamoyl-1,1-diphenylmethyl)pyrrolidin-1-yl)hep-1-yl]-N-(isopropyl)amino}-1-{2,4-di(difluoromethoxy)pyrid-3-ylmethyl}piperidine;

4-{N-[7-(3-(S)-1-carbamoyl-1,1-diphenylmethyl)pyrrolidin-1-yl)hep-1-yl]-N-(isopropyl)amino}-1-(2-ethoxy-4-trifluoromethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2-ethoxy-4-difluoromethoxypyrid-3-ylmethyl)piperidine;

4-{N-[7-(3-(S)-1-carbamoyl-1,1-diphenylmethyl)pyrrolidin-1-yl)hep-1-yl]-N-(isopropyl)amino}-1-(2,4-diethoxypyrid-3-ylmethyl)piperidine;

4-{N-[7-(3-(S)-1-(N-methylcarbamoyl)-1,1-diphenylmethyl)pyrrolidin-1-yl)hep-1-yl]-N-(isopropyl)amino}-1-(4-methoxypyrid-3-ylmethyl)piperidine;

4-{N-[7-(3-(S)-1-(N,N-dimethylcarbamoyl)-1,1-diphenylmethyl)pyrrolidin-1-yl)hep-1-yl]-N-(isopropyl)amino}-1-(4-hydroxypyrid-3-ylmethyl)piperidine;

4-{N-[7-(3-(S)-1-(N,N-diethylcarbamoyl)-1,1-diphenylmethyl)pyrrolidin-1-yl)hep-1-yl]-N-(isopropyl)amino}-1-(4-hydroxypyrid-3-ylmethyl)piperidine;

4-{N-[7-(3-(S)-1-(piperidin-1-ylcarbonyl)-1,1-diphenylmethyl)pyrrolidin-1-yl)hep-1-yl]-N-(isopropyl)amino}-1-(4-hydroxypyrid-3-ylmethyl)piperidine;

4-{N-[7-(3-(S)-1-(morpholin-4-ylcarbonyl)-1,1-diphenylmethyl)pyrrolidin-1-yl)hep-1-yl]-N-(isopropyl)amino}-1-(4-hydroxypyrid-3-ylmethyl)piperidine; and 4-{N-[7-(3-(S)-1-Carbamoyl-1,1-diphenylmethyl)pyrrolidin-1-yl)hep-1-yl]-N-(isopropyl)amino}-1-[4-(2-fluoroethoxy)pyrid-3-ylmethyl]piperidine;

4-{N-[7-(3-(R)-1-Carbamoyl-1,1-diphenylmethyl)pyrrolidin-1-yl)hep-1-yl]-N-(isopropyl)amino}-1-(4-methoxypyrid-3-ylmethyl)piperidine; and 4-{N-[7-(3-(R)-1-Carbamoyl-1,1-diphenylmethyl)pyrrolidin-1-yl)hep-1-yl]-N-(isopropyl)amino}-1-(4-ethoxypyrid-3-ylmethyl)piperidine;

or a pharmaceutically-acceptable salt or stereoisomer thereof.

31. 4-{N-[7-(3-(S)-1-Carbamoyl-1,1-diphenylmethyl)pyrrolidin-1-yl)hept-1-yl]-N-(isopropyl)amino}-1-(4-methoxypyrid-3-ylmethyl)piperidine; or a pharmaceutically-acceptable salt thereof.

32. 4-{N-[7-(3-(S)-1-Carbamoyl-1,1-diphenylmethyl)pyrrolidin-1-yl)hept-1-yl]-N-(isopropyl)amino}-1-(4-ethoxypyrid-3-ylmethyl)piperidine; or a pharmaceutically-acceptable salt thereof.

33. 4-{N-[7-(3-(S)-1-Carbamoyl-1,1-diphenylmethyl)pyrrolidin-1-yl)hept-1-yl]-N-(isopropyl)amino}-1-(4-isopropoxypyrid-3-ylmethyl)piperidine; or a pharmaceutically-acceptable salt thereof.

34. A pharmaceutical composition comprising a pharmaceutically-acceptable carrier and a therapeutically effective amount of a compound of any one of claims 1-33.

35. A process for preparing a compound of formula I:

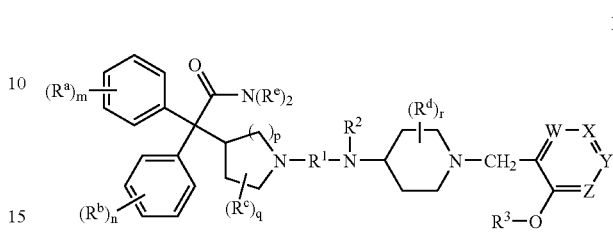

wherein $R^1$, $R^2$, $R^3$, $R^a$, $R^b$, $R^c$, $R^d$, m, n, p, q, r, W, X, Y and Z are as defined in claim 1; or a pharmaceutically-acceptable salt or stereoisomer thereof;

the process comprising reacting a compound of formula Va:

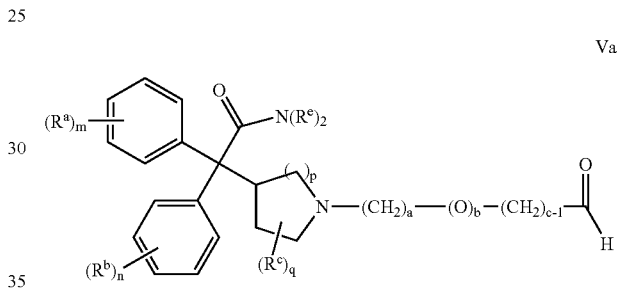

or a salt or stereoisomer or protected derivative thereof; with a compound of formula VIII:

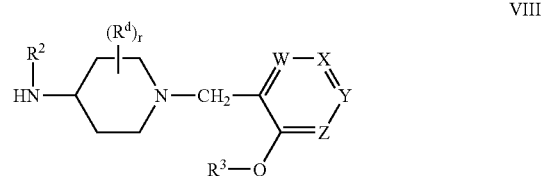

or a salt or protected derivative thereof; and a reducing agent to provide a compound of formula I, or a pharmaceutically-acceptable salt or stereoisomer thereof.

36. The process of claim 35, wherein the process further comprises the step of forming a pharmaceutically-acceptable salt of the compound of formula I.

* * * * *

UNITED STATES PATENT AND TRADEMARK OFFICE
CERTIFICATE OF CORRECTION

PATENT NO. : 7,285,564 B2
APPLICATION NO. : 10/696464
DATED : October 23, 2007
INVENTOR(S) : Mathai Mammen et al.

It is certified that error appears in the above-identified patent and that said Letters Patent is hereby corrected as shown below:

Column 77
at line 13, "$-CH^2-R^5$" should read "$-CH_2-R^5$"

at lines 21, 31 and 67, "substitutents" should read "substituents"

at line 23, "$C_{2-4}$ alkynyl" should read "$C_{2-6}$ alkynyl"

Column 78
at lines 4, 13, 20, 27, 29, 46 and 57, "substitutents" should read "substituents"

at line 6, "$C_{2-4}$ alkynyl" should read "$C_{2-6}$ alkynyl"

Column 80
at line 1, "$-(CH^2)_x$-phenyl" should read "$-(CH_2)_x$-phenyl"

Column 81
at line 12, "$C_2$-alkenyl" should read "$C_{2-6}$ alkenyl"

at lines 21, 31 and 62, "substitutents" should read "substituents"

at line 59, "$C_{2-4}$ alkyl" should read "$C_{2-4}$ alkynyl"

Column 82
at lines 2, 4 and 13, "substitutents" should read "substituents"

UNITED STATES PATENT AND TRADEMARK OFFICE
CERTIFICATE OF CORRECTION

PATENT NO. : 7,285,564 B2
APPLICATION NO. : 10/696464
DATED : October 23, 2007
INVENTOR(S) : Mathai Mammen et al.

It is certified that error appears in the above-identified patent and that said Letters Patent is hereby corrected as shown below:

Column 83
at line 3, "-CH$^2$-R$^5$" should read "-CH$_2$-R$^5$"

at lines 11, 42, 49, 51 and 61, "substitutents" should read "substituents"

Signed and Sealed this

Seventeenth Day of March, 2009

JOHN DOLL
*Acting Director of the United States Patent and Trademark Office*